United States Patent
Yates et al.

(10) Patent No.: US 9,566,255 B2
(45) Date of Patent: *Feb. 14, 2017

(54) METHOD FOR REGULATING RETINAL ENDOTHELIAL CELL VIABILITY

(71) Applicant: The University of Tennessee Research Foundation, Memphis, TN (US)

(72) Inventors: Charles Ryan Yates, Collierville, TN (US); Jena Steinle Smith, Olive Branch, MS (US); Duane Douglas Miller, Collierville, TN (US); Jordan J. Toutounchian, Memphis, TN (US)

(73) Assignee: The University of Tennessee Research Foundation, Memphis, TN (US)

(*) Notice: Subject to any disclaimer, the term of this patent is extended or adjusted under 35 U.S.C. 154(b) by 127 days.

This patent is subject to a terminal disclaimer.

(21) Appl. No.: 14/074,457

(22) Filed: Nov. 7, 2013

(65) Prior Publication Data

US 2014/0094518 A1   Apr. 3, 2014

Related U.S. Application Data

(63) Continuation-in-part of application No. 13/320,540, filed on Jun. 6, 2012.

(60) Provisional application No. 61/723,733, filed on Nov. 7, 2012, provisional application No. 61/807,303, filed on Apr. 1, 2013.

(51) Int. Cl.
| | |
|---|---|
| *A61K 31/16* | (2006.01) |
| *A61K 31/015* | (2006.01) |
| *A61K 31/191* | (2006.01) |
| *A61K 31/164* | (2006.01) |
| *A61K 31/4453* | (2006.01) |

(52) U.S. Cl.
CPC .......... *A61K 31/191* (2013.01); *A61K 31/164* (2013.01); *A61K 31/4453* (2013.01)

(58) Field of Classification Search
CPC . A61K 31/191; A61K 31/164; A61K 31/4453
See application file for complete search history.

(56) References Cited

U.S. PATENT DOCUMENTS

| | | |
|---|---|---|
| 2010/0055137 A1 | 3/2010 | Larm et al. |
| 2011/0159121 A1 | 6/2011 | McDaniel |
| 2012/0128657 A1 | 5/2012 | Bewley |

FOREIGN PATENT DOCUMENTS

WO   WO2010/132504   11/2010

OTHER PUBLICATIONS

Zamber et al. (West J Med. Nov. 1992; 157(5), 530-533).*
Leal et al. High glucose and oxidative/nitrosative stress conditions induce apoptosis in retinal endothelial cells by a caspase-independent pathway, Experimental Eye Research, (2009) pp. 1-9. p. 1, title, abstract, col. 1, para 1.
Robbins et al. Cultivation Conditions and Selenium Fertilization Alter the Phenolic Profile. Glucosinolate, and Sulforaphane Content of Broccoli, Journal of Medicinal Food 8 (2) 2005, 204-214. p. 207, Figure 1C; p. 208, Col1, para 2 and para 4; col. 2, para 1, Table 1.
International Search Report for PCT/US13/68983.
Written Opinion for PCT/US13/68983.
Abramson, D.H., I.J. Dunkel, S.E. Brodie, J.W. Kim, and Y.P. Gobin. 2008. A phase I/II study of direct intraarterial (ophthalmic artery) chemotherapy with melphalan for intraocular retinoblastoma initial results. Ophthalmology. 115:1398-1404, 1404 e1391.
Aiello, L.P., E.A. Pierce, E.D. Foley, H. Takagi, H. Chen, L. Riddle, N. Ferrara, G.L. King, and L.E. Smith. 1995. Suppression of retinal neovascularization in vivo by inhibition of vascular endothelial growth factor (VEGF) using soluble VEGF-receptor chimeric proteins. Proceedings of the National Academy of Sciences of the United States of America. 92:10457-10461.
Akesson, C., H. Lindgren, R.W. Pero, T. Leanderson, and F. Ivars. 2005. Quinic acid is a biologically active component of the *Uncaria tomentosa* extract C-Med 100. International immunopharmacology. 5:219-229.
Alessi, D.R., M. Andjelkovic, B. Caudwell, P. Cron, N. Morrice, P. Cohen, and B.A. Hemmings. 1996. Mechanism of activation of protein kinase B by insulin and IGF-1. The EMBO journal. 15:6541-6551.
Alon, R., R.C. Fuhlbrigge, E.B. Finger, and T.A. Springer. 1996. Interactions through L-selectin between leukocytes and adherent leukocytes nucleate rolling adhesions on selectins and VCAM-1 in shear flow. The Journal of cell biology. 135:849-865.
Ammar, H.O., H.A. Salama, M. Ghorab, and A.A. Mahmoud. 2009. Nanoemulsion as a potential ophthalmic delivery system for dorzolamide hydrochloride. AAPS PharmSciTech. 10:808-819.
Arnold, T.D., G.M. Ferrero, H. Qiu, I.T. Phan, R.J. Akhurst, E.J. Huang, and L.F. Reichardt. 2012. Defective retinal vascular endothelial cell development as a consequence of impaired integrin alphaVbeta8-mediated activation of transforming growth factor-beta. The Journal of neuroscience : the official journal of the Society for Neuroscience. 32:1197-1206.
Avery, R.B., M. Diener-West, S.M. Reynolds, H.E. Grossniklaus, W.R. Green, and D.M. Albert. 2008. Histopathologic characteristics of choroidal melanoma in eyes enucleated after iodine 125 brachytherapy in the collaborative ocular melanoma study. Archives of ophthalmology. 126:207-212.
Bassoli, B.K., P. Cassolla, G.R. Borba-Murad, J. Constantin, C.L. Salgueiro-Pagadigorria, R.B. Bazotte, R.S. da Silva, and H.M. de Souza. 2008. Chlorogenic acid reduces the plasma glucose peak in the oral glucose tolerance test: effects on hepatic glucose release and glycaemia. Cell biochemistry and function. 26:320-328.
Bianciotto, C., C.L. Shields, C. Pirondini, A. Mashayekhi, M. Furuta, and J.A. Shields. 2010. Proliferative radiation retinopathy after plaque radiotherapy for uveal melanoma. Ophthalmology. 117:1005-1012.

(Continued)

*Primary Examiner* — Zohreh Fay
(74) *Attorney, Agent, or Firm* — Lihua Zheng

(57) ABSTRACT

Here provided is a method for regulating retinal endothelial cell viability in a mammal by administering to the mammal a therapeutically effective amount of a quinic acid analog. The method may be applied to prevent, treat or cure pathological conditions of retinal endothelial cells associated with radiation retinopathy, diabetic retinopathy and chemotherapy for retinoblastoma.

16 Claims, 46 Drawing Sheets

(56) References Cited

OTHER PUBLICATIONS

Brown, G.C., J.A. Shields, G. Sanborn, J.J. Augsburger, P.J. Savino, and N.J. Schatz. 1982. Radiation retinopathy. Ophthalmology. 89:1494-1501.
Burns, A.R., R.A. Bowden, Y. Abe, D.C. Walker, S.I. Simon, M.L. Entman, and C.W. Smith. 1999. P-selectin mediates neutrophil adhesion to endothelial cell borders. Journal of leukocyte biology. 65:299-306.
Cai, Y., Q. Luo, M. Sun, and H. Corke. 2004. Antioxidant activity and phenolic compounds of 112 traditional Chinese medicinal plants associated with anticancer. Life sciences. 74:2157-2184.
Carpenter, C.L., B.C. Duckworth, K.R. Auger, B. Cohen, B.S. Schaffhausen, and L.C. Cantley. 1990. Purification and characterization of phosphoinositide 3-kinase from rat liver. The Journal of biological chemistry. 265:19704-19711.
Chang, W.C., C.H. Chen, M.F. Lee, T. Chang, and Y.M. Yu. 2010. Chlorogenic acid attenuates adhesion molecules upregulation in IL-1beta-treated endothelial cells. European journal of nutrition. 49:267-275.
Connor, K.M., N.M. Krah, R.J. Dennison, C.M. Aderman, J. Chen, K.I. Guerin, P. Sapieha, A. Stahl, K.L. Willett, and L.E. Smith. 2009. Quantification of oxygen-induced retinopathy in the mouse: a model of vessel loss, vessel regrowth and pathological angiogenesis. Nature protocols. 4:1565-1573.
Conti, S.M., and P.J. Kertes. 2006. The use of intravitreal corticosteroids, evidence-based and otherwise. Current opinion in ophthalmology. 17:235-244.
Costa, G.N., J. Vindeirinho, C. Cavadas, A.F. Ambrósio, and P.F. Santos. 2012. Contribution of TNF receptor 1 to retinal neural cell death induced by elevated glucose. Molecular and Cellular Neuroscience. 50:113-123.
Diener-West, M., J.D. Earle, S.L. Fine, B.S. Hawkins, C.S. Moy, S.M. Reynolds, A.P. Schachat, and B.R. Straatsma. 2001. The COMS randomized trial of iodine 125 brachytherapy for choroidal melanoma, III: initial mortality findings. COMS Report No. 18. Archives of ophthalmology. 119:969-982.
Ditta, L.C., A.F. Choudhri, B.C. Tse, M.M. Landers, B.G. Haik, J.J. Steinle, J.S. Williams, and M.W. Wilson. 2012. Validating a Non-Human Primate Model of Super-Selective Intra-Ophthalmic Artery Chemotherapy: Comparing Ophthalmic Artery Diameters. Investigative ophthalmology & visual science.
Egger, E., A. Schalenbourg, L. Zografos, L. Bercher, T. Boehringer, L. Chamot, and G. Goitein. 2001. Maximizing local tumor control and survival after proton beam radiotherapy of uveal melanoma. International journal of radiation oncology, biology, physics. 51:138-147.
El-Remessy, A.B., M. Bartoli, D.H. Platt, D. Fulton, and R.B. Caldwell. 2005. Oxidative stress inactivates VEGF survival signaling in retinal endothelial cells via PI 3-kinase tyrosine nitration. Journal of cell science. 118:243-252.
Engerman, R.L. 1989. Pathogenesis of diabetic retinopathy. Diabetes. 38:1203-1206.
Espinoza-Fonseca, L.M. 2005. Targeting MDM2 by the small molecule RITA: towards the development of new multi-target drugs against cancer. Theoretical biology & medical modelling. 2:38.
Finger, P.T., K.J. Chin, and G. Duvall. 2009. Palladium-103 ophthalmic plaque radiation therapy for choroidal melanoma: 400 treated patients. Ophthalmology. 116:790-796, 796 e791.
Frangos, J.A., L.V. McIntire, and S.G. Eskin. 1988. Shear stress induced stimulation of mammalian cell metabolism. Biotechnol Bioeng. 32:1053-1060.
Gaber, M.W., O.M. Sabek, K. Fukatsu, H.G. Wilcox, M.F. Kiani, and T.E. Merchant. 2003. Differences in ICAM-1 and TNF-alpha expression between large single fraction and fractionated irradiation in mouse brain. International journal of radiation biology. 79:359-366.
Geraldes, P., J. Hiraoka-Yamamoto, M. Matsumoto, A. Clermont, M. Leitges, A. Marette, L.P. Aiello, T.S. Kern, and G.L. King. 2009. Activation of PKC-delta and SHP-1 by hyperglycemia causes vascular cell apoptosis and diabetic retinopathy. Nature medicine. 15:1298-1306.
Gillies, M.C., F.K. Sutter, J.M. Simpson, J. Larsson, H. Ali, and M. Zhu. 2006. Intravitreal triamcinolone for refractory diabetic macular edema: two-year results of a double-masked, placebo-controlled, randomized clinical trial. Ophthalmology. 113:1533-1538.
Giuliari, G.P., A. Sadaka, D.M. Hinkle, and E.R. Simpson. 2011. Current treatments for radiation retinopathy. Acta Oncologica. 50:6-13.
Gobin, Y.P., I.J. Dunkel, B.P. Marr, S.E. Brodie, and D.H. Abramson. 2011. Intra-arterial Chemotherapy for the Management of Retinoblastoma: Four-Year Experience. Archives of ophthalmology. 129:732-737.
Googe, J., A.J. Brucker, N. M. Bressler, H. Qin, L.P. Aiello, A. Antoszyk, R.W. Beck, S.B. Bressler, F.L. Ferris, 3rd, A.R. Glassman, D. Marcus, and C.R. Stockdale. 2011. Randomized trial evaluating short-term effects of intravitreal ranibizumab or triamcinolone acetonide on macular edema after focal/grid laser for diabetic macular edema in eyes also receiving panretinal photocoagulation. Retina. 31:1009-1027.
Gunduz, K., C.L. Shields, J.A. Shields, J. Cater, J.E. Freire, and L.W. Brady. 1999. Radiation complications and tumor control after plaque radiotherapy of choroidal melanoma with macular involvement. American journal of ophthalmology. 127:579-589.
Haas, A., O. Pinter, G. Papaefthymiou, M. Weger, A. Berghold, O. Schrottner, K. Mullner, G. Pend, and G. Langmann. 2002. Incidence of radiation retinopathy after high-dosage single-fraction gamma knife radiosurgery for choroidal melanoma. Ophthalmology. 109:909-913.
Ho, F.M., S.H. Liu, C.S. Liau, P.J. Huang, and S.Y. Lin-Shiau. 2000. High glucose-induced apoptosis in human endothelial cells is mediated by sequential activations of c-Jun NH(2)-terminal kinase and caspase-3. Circulation. 101:2618-2624.
Jampol, L.M., C.S. Moy, T.G. Murray, S.M. Reynolds, D.M. Albert, A.P. Schachat, K.R. Diddie, R.E. Engstrom, Jr., P.T. Finger, K.R. Hovland, L. Joffe, K.R. Olsen, and C.G. Wells. 2002. The COMS randomized trial of iodine 125 brachytherapy for choroidal melanoma: IV. Local treatment failure and enucleation in the first 5 years after brachytherapy. COMS report No. 19. Ophthalmology. 109:2197-2206.
Jiang, Y., Q. Zhang, C. Soderland, and J.J. Steinle. 2012. TNFalpha and SOCS3 regulate IRS-1 to increase retinal endothelial cell apoptosis. Cellular signalling. 24:1086-1092.
Johnston, K.L., M.N. Clifford, and L.M. Morgan. 2003. Coffee acutely modifies gastrointestinal hormone secretion and glucose tolerance in humans: glycemic effects of chlorogenic acid and caffeine. The American journal of clinical nutrition. 78:728-733.
Kinashi, T. 2005. Intracellular signalling controlling integrin activation in lymphocytes. Nature reviews. Immunology. 5:546-559.
Krema, H., S. Somani, A. Sahgal, W. Xu, M. Heydarian, D. Payne, H. McGowan, H. Michaels, E.R. Simpson, and N. Laperriere. 2009. Stereotactic radiotherapy for treatment of juxtapapillary choroidal melanoma: 3-year follow-up. The British journal of ophthalmology. 93:1172-1176.
Lawrence, M.B., L.V. McIntire, and S.G. Eskin. 1987. Effect of flow on polymorphonuclear leukocyte/endothelial cell adhesion. Blood. 70:1284-1290.
Ley, K., C. Laudanna, M.I. Cybulsky, and S. Nourshargh. 2007. Getting to the site of inflammation: the leukocyte adhesion cascade updated. Nature reviews. Immunology. 7:678-689.
Marshall, S.M., and A. Flyvbjerg. 2006. Prevention and early detection of vascular complications of diabetes. BMJ. 333:475-480.
McCarty, O.J., S.A. Mousa, P.F. Bray, and K. Konstantopoulos. 2000. Immobilized platelets support human colon carcinoma cell tethering, rolling, and firm adhesion under dynamic flow conditions. Blood. 96:1789-1797.
Miyamoto, K., S. Khosrof, S.E. Bursell, R. Rohan, T. Murata, A.C. Clermont, L.P. Aiello, Y. Ogura, and A.P. Adamis. 1999. Prevention of leukostasis and vascular leakage in streptozotocin-induced diabetic retinopathy via intercellular adhesion molecule-1 inhibition. Proceedings of the National Academy of Sciences of the United States of America. 96:10836-10841.

(56) References Cited

OTHER PUBLICATIONS

Munier, F.L., M. Beck-Popovic, A. Balmer, M.C. Gaillard, E. Bovey, and S. Binaghi. 2011. Occurrence of sectoral choroidal occlusive vasculopathy and retinal arteriolar embolization after superselective ophthalmic artery chemotherapy for advanced intraocular retinoblastoma. Retina. 31:566-573.
Olthof, M.R., P.C. Holtman, and M.B. Katan. 2001. Chlorogenic acid and caffeic acid are absorbed in humans. The Journal of nutrition. 131:66-71.
Parks, D.J., L.V. Lafrance, R.R. Calvo, K.L. Milkiewicz, V. Gupta, J. Lattanze, K. Ramachandren, T.E. Carver, E.C. Petrella, M.D. Cummings, D. Maguire, B.L. Grasberger, and T. Lu. 2005. 1,4-Benzodiazepine-2,5-diones as small molecule antagonists of the HDM2-p53 interaction: discovery and SAR. Bioorganic & medicinal chemistry letters. 15:765-770.
Pham, C.T., R. Blanc, L. Lumbroso-Le Rouic, S. Pistocchi, B. Bartolini, and M. Piotin. 2012. Access to the ophthalmic artery by retrograde approach through the posterior communicating artery for intra-arterial chemotherapy of retinoblastoma. Neuroradiology. 54:845-848.
Phillpotts, B.A., R.J. Sanders, J.A. Shields, J.D. Griffiths, J.A. Augsburger, and C.L. Shields. 1995. Uveal melanomas in black patients: a case series and comparative review. Journal of the National Medical Association. 87:709-714.
Ramagiri, S., F. Ma, H. Kosanam, X. Wang, R. Patil, D.D. Miller, E. Geisert, and C.R. Yates. 2009. Fast and sensitive liquid chromatography/electrospray mass spectrometry method to study ocular penetration of EDL-155, a novel antitumor agent for retinoblastoma in rats. Journal of mass spectrometry : JMS. 44:786-793.
Shafiq-un-Nabi, S., F. Shakeel, S. Talegaonkar, J. Ali, S. Baboota, A. Ahuja, R.K. Khar, and M. Ali. 2007. Formulation development and optimization using nanoemulsion technique: a technical note. AAPS PharmSciTech. 8:Article 28.
Sheng, Y., C. Akesson, K. Holmgren, C. Bryngelsson, V. Giamapa, and R.W. Pero. 2005. An active ingredient of Cat's Claw water extracts identification and efficacy of quinic acid. Journal of ethnopharmacology. 96:577-584.
Shields, C.L., C.G. Bianciotto, P. Jabbour, G.C. Griffin, A. Ramasubramanian, R. Rosenwasser, and J.A. Shields. 2011. Intra-arterial Chemotherapy for Retinoblastoma: Report No. 2, Treatment Complications. Archives of ophthalmology.
Shimura, M., K. Yasuda, T. Nakazawa, T. Kano, S. Ohta, and M. Tamai. 2003. Quantifying alterations of macular thickness before and after panretinal photocoagulation in patients with severe diabetic retinopathy and good vision. Ophthalmology. 110:2386-2394.
Smith, L.E., E. Wesolowski, A. McLellan, S.K. Kostyk, R. D'Amato, R. Sullivan, and P.A. D'Amore. 1994. Oxygen-induced retinopathy in the mouse. Investigative ophthalmology & visual science. 35:101-111.
Springer, T.A. 1995. Traffic signals on endothelium for lymphocyte recirculation and leukocyte emigration. Annual review of physiology. 57:827-872.
Stahl, A., K.M. Connor, P. Sapieha, J. Chen, R.J. Dennison, N. M. Krah, M.R. Seaward, K.L. Willett, C.M. Aderman, K.I. Guerin, J. Hua, C. Lofqvist, A. Hellstrom, and L.E. Smith. 2010. The mouse retina as an angiogenesis model. Investigative ophthalmology & visual science. 51:2813-2826.
Steinle, J.J., Q. Zhang, K.E. Thompson, J. Toutounchian, C.R. Yates, C. Soderland, F. Wang, C. Stewart, B.G. Haik, J.S. Williams, J.S. Jackson, T.D. Mandrell, D.A. Johnson, and M.W. Wilson. 2012a. Intra-ophthalmic artery chemotherapy triggers vascular toxicity through endothelial cell inflammation and leukostasis. Investigative ophthalmology & visual science.
Vanhaesebroeck, B., S.J. Leevers, K. Ahmadi, J. Timms, R. Katso, P.C. Driscoll, R. Woscholski, P.J. Parker, and M.D. Waterfield. 2001. Synthesis and function of 3-phosphorylated inositol lipids. Annual review of biochemistry. 70:535-602.
Vassilev, L.T., B.T. Vu, B. Graves, D. Carvajal, F. Podlaski, Z. Filipovic, N. Kong, U. Kammlott, C. Lukacs, C. Klein, N. Fotouhi, and E.A. Liu. 2004. In vivo activation of the p53 pathway by small-molecule antagonists of MDM2. Science. 303:844-848.
Viebahn, M., M.E. Barricks, and M.D. Osterloh. 1991. Synergism between diabetic and radiation retinopathy: case report and review. The British journal of ophthalmology. 75:629-632.
Wagers, A.J., C.M. Waters, L.M. Stoolman, and G.S. Kansas. 1998a. Interleukin 12 and interleukin 4 control T cell adhesion to endothelial selectins through opposite effects on alpha1, 3-fucosyltransferase VII gene expression. The Journal of experimental medicine. 188:2225-2231.
Waisbourd, M., M. Goldstein, and A. Loewenstein. 2011. Treatment of diabetic retinopathy with anti-VEGF drugs. Acta ophthalmologica. 89:203-207.
Wilson, M.W., J.S. Jackson, B.X. Phillips, J. Buchanan, S. Frase, F. Wang, J.J. Steinle, C.F. Stewart, T.D. Mandrell, B.G. Haik, and J.S. Williams. 2011. Real-time ophthalmoscopic findings of superselective intraophthalmic artery chemotherapy in a nonhuman primate model. Archives of ophthalmology. 129:1458-1465.
Witt, T.C. 2003. Stereotactic radiosurgery for pituitary tumors. Neurosurgical focus. 14:e10.
Yamane, T., A. Kaneko, and M. Mohri. 2004. The technique of ophthalmic arterial infusion therapy for patients with intraocular retinoblastoma. Int J Clin Oncol. 9:69-73.
Yu, Y.M., Z.H. Wang, C.H. Liu, and C.S. Chen. 2007. Ellagic acid inhibits IL-1beta-induced cell adhesion molecule expression in human umbilical vein endothelial cells. The British journal of nutrition. 97:692-698.
Yuan, H., M.W. Gaber, T. McColgan, M.D. Naimark, M.F. Kiani, and T.E. Merchant. 2003. Radiation-induced permeability and leukocyte adhesion in the rat blood-brain barrier: modulation with anti-ICAM-1 antibodies. Brain research. 969:59-69.
Zamber, R.W., and J.L. Kinyoun. 1992. Radiation retinopathy. The Western journal of medicine. 157:530-533.
Zeng, K., K.E. Thompson, C.S. Presley, D.D. Miller, and C.R. Yates. 2011. Preclinical pharmacokinetics of the radiomitigator KZ-41 in rats. Xenobiotica; the fate of foreign compounds in biological systems. 41:1006-1012.
Zeng, K., K.E. Thompson, C.R. Yates, and D.D. Miller. 2009. Synthesis and biological evaluation of quinic acid derivatives as anti-inflammatory agents. Bioorganic & medicinal chemistry letters. 19:5458-5460.
Zhang, Q., C. Soderland, and J.J. Steinle. 2013. Regulation of retinal endothelial cell apoptosis through activation of the IGFBP-3 receptor. Apoptosis : an international journal on programmed cell death. 18:361-368.
Zhang, X., G. Barile, S. Chang, A. Hays, S. Pachydaki, W. Schiff, and J. Sparrow. 2005. Apoptosis and cell proliferation in proliferative retinal disorders: PCNA, Ki-67, caspase-3, and PARP expression. Current eye research. 30:395-403.
Zhong, H., and H.A. Carlson. 2005. Computational studies and peptidomimetic design for the human p53-MDM2 complex. Proteins. 58:222-234.

* cited by examiner

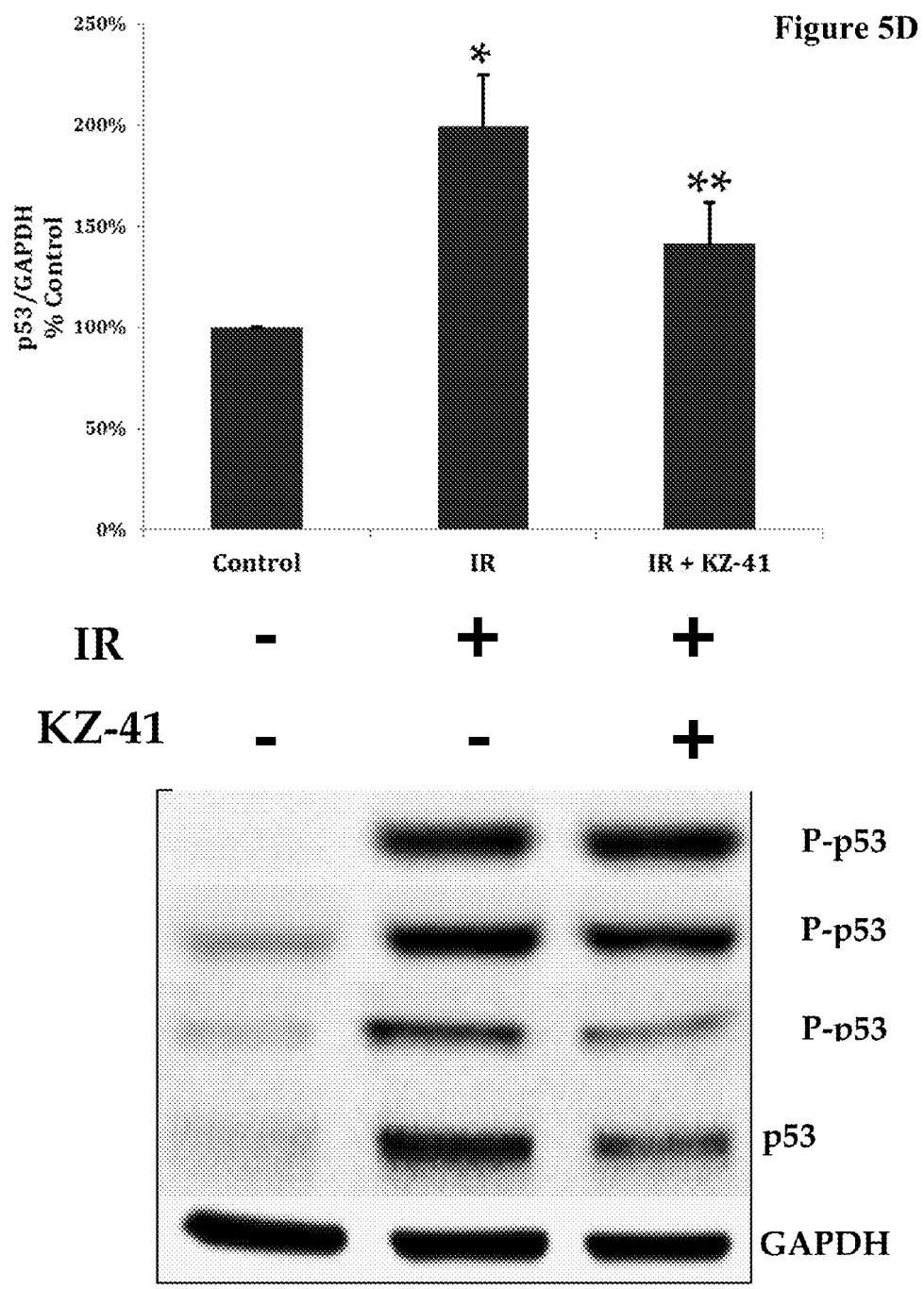

Capryol 90      (7.5%   v/v)
Triacetin       (7.5%   v/v)
Tween-20        (17.5%  v/v)
Transcutol P    (17.5%  v/v)

| Ophthalmic Nanoemulsion Characterization | |
|---|---|
| Viscosity (mPa s) | 17.03 ± 1.8e⁻⁵ |
| pH | 6.52 ± 0.04 |
| Particle Size Day 0 (nm) | 61.3 ± 2 |
| Particle Size Day 7 (nm) | 59.3 ± 11 |
| Particle Size post 3x freeze-thaw (nm) | 58.7 ± 0.3 |

| KZ-41 concentration after Ocular administration Mean ± SD | | |
|---|---|---|
| Time (h) | Eye (mg/g) | Plasma (ng/mL) |
| 0.08 | 71.60 ± 7.69 | BLOQ |
| 0.25 | 130.1 ± 4.60 | BLOQ |
| 0.5 | 57.70 ± 13.4 | 4180 ± 979.2 |
| 1 | 32.80 ± 7.26 | 4767 ± 885.6 |
| 4 | 13.50 ± 2.34 | 292.5 ± 45.55 |
| 8 | BLOQ | 203.3 ± 79.01 |
| 24 | BLOQ | 21.57 ± 2.30 |

Avascular Area

Neovascular Area

METHOD FOR REGULATING RETINAL ENDOTHELIAL CELL VIABILITY

CROSS-REFERENCE TO RELATED APPLICATIONS

This application claims the benefit of priority of earlier-filed U.S. Provisional Patent Application Nos. 61/723,733 filed on Nov. 7, 2012 and 61/807,303 filed Apr. 1, 2013, and is a continuation-in-part of U.S. patent application Ser. No. 13/320,540 filed on Jun. 6, 2012, the disclosure of which applications are incorporated herein by reference.

GOVERNMENTAL SUPPORT

Certain aspects of the invention, namely, the study on radiation retinopathy in Example 1, were supported by NIH/NIAID grant R33AI080534-01. The U.S. government may have certain rights in the invention.

FIELD OF INVENTION

The present invention relates to a new use of quinic acid analogs in regulating retinal endothelial cell (REC) viability. More specifically, the invention relates to methods to prevent, treat or cure diabetes-, radiation-, or chemotherapy-induced pathological conditions in RECs.

BACKGROUND

Retinal neovascularization (RNV) represents the leading cause of blindness in humans and can be triggered by a variety of ocular insults, e.g., high glucose, radiation, and chemotherapy. RNV may be caused by REC death due to an exuberant pro-inflammatory response triggered by damages to the posterior vascularized portion of the eye (Brown et al., 1982; Viebahn et al., 1991; Zamber and Kinyoun, 1992). Because new vessels formed under hypoxia are fragile and leaky, RNV often leads to macular edema, retinal detachment and blindness. For example, as shown in FIG. 1, irradiation of the eye can trigger leukocyte adhesion, accumulation, and blockage of retinal vasculature, which may result in hypoxia, abnormal retinal neovascularization and ultimately loss of vision.

Treatments for RNV include glucocorticoids, anti-vascular endothelial growth factor (VEGF) monoclonal antibodies, and surgical intervention (panretinal photocoagulation [PRP]) (Aiello et al., 1995; Googe et al., 2011). These treatments are often not effective and also limited by side effects such as ocular hypertension, glaucoma, cataracts, retinal detachment, and endophthalmitis (Conti and Kertes, 2006; Gillies et al., 2006; Waisbourd et al., 2011).

We have discovered a new class of quinic acid analogs (QAAs) that are are resistant to bacterial degradation (Zeng et al., 2011; Zeng et al., 2009). We have previously demonstrated that the QAAs, e.g., KZ-41 (1,3,4,5-tetrahydroxy-1-cyclohexanecarboxylic acid), can exert a significant pro-survival effect in a whole murine model of high dose radiation injury. See U.S. Patent Application Publication No. 2012/0283331. Here we disclose another surprising discovery that QAAs can regulate REC viability due to radiation, chemotherapy or high glucose, and therefore prevent, treat or cure RNV-caused blindness.

SUMMARY OF THE INVENTION

The invention relates to a method for regulating REC viability in a mammal by administering to the mammal a therapeutically effective amount of a quinic acid analogs (QAAs) having a structure as in Formula I.

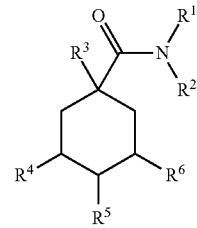

In Formula I, the ring may be singly, doubly, or completely saturated; $R^1$ and $R^2$ are each independently H, straight or branched alkyl, aryl, benzyl, arylalkyl, or heterocyclic amine; $R^3$ may be present or absent and, if present, may be H, hydroxyl, ether, alkoxy, or aryloxy; and $R^4$, $R^5$, and $R^6$ are each independently H, hydroxyl, or alkoxy.

In some embodiments, $R^1$ and $R^2$ of Formula I form a piperidine ring with nitrogen (N). In other embodiments, when one of $R^1$ or $R^2$ of Formula I is hydrogen, the other of $R^1$ or $R^2$ is alkyl. In one instance of QAA, the alkyl is $-C_3H_7$ and each of $R^3$-$R^6$ is hydroxyl.

In some embodiments, the method may be used to prevent, treat or cure radiation retinopathy due to exposure of the mammal's RECs to radiation. For example, the radiation such as (gamma) γ radiation may be used to treat an intraocular tumor.

In other embodiments, the method may be used to prevent, treat or cure eye complications caused by chemotherapy in treating retinoblastoma. The chemotherapy may be super-selective intra-ophthalmic artery chemotherapy. In one instance, the chemotherapy may employ the substance melphalan.

In still other embodiments, the method may be used to prevent, treat or cure diabetic retinopathy. Diabetic retinopathy may be due to long time exposure of the mammal's RECs to high glucose levels. In some instances, the mammal may be a human.

In still other embodiments, the method may be used to regulate REC viability for purposes of promoting or maintaining REC viability. In other embodiments, the purpose is to reduce REC death. In further embodiments, the purpose is to prevent or reduce retinal neovascularization.

In some embodiments, the method is used in combination with one or more existing treatment methods for radiation retinopathy, diabetic retinopathy, or mitigating side effects on RECs in treating retinoblastoma. In some instances, the quinic acid analog used in the method is formulated in nanoemulsion and may be delivered as an eye-drop.

BRIEF DESCRIPTION OF THE DRAWINGS

In FIG. 2A, the x-axis shows three groups of experiments: control group referring to human RECs without irradiation or KZ-41 treatment; IR group referring to human RECs treated with irradiation; and IR+KZ-41 group referring to human RECs treated with both irradiation and KZ-41. The y-axis shows the percentage of mean fluorescence values for each group.

FIG. 2B shows a graph depicting the results of monocyte adhesion assays in the upper panel and images of cells in plates in the lower panel. In upper panel graph, the x-axis shows three groups of experiments: control group referring to human RECs without irradiation or KZ-41 treatment; irradiation group referring to human RECs treated with irradiation; and IR+KZ-41 group referring to human RECs treated with both irradiation and KZ-41. The y-axis shows number of monocyte cells per field for each group. The images in the lower panel shows the monocyte cells adhered to the human RECs in each of the three groups: A for the Control group; B for irradiation group; and C for the IR+KZ-41 group.

FIG. 3A shows images taken with confocal microscopy of flow-chamber slides. In FIG. 3A, the top panel (A, D and G), the middle panel (B, E and H), and the lower panel (C, F and I) represent overlay images of DAPI, P-Selectin and ICAM-1, respectively. The columns A-C, D-F, G-I represent the three treatment groups: control group referring to human RECs without irradiation or KZ-41 treatment; IR group referring to human RECs treated with irradiation; and IR+KZ-41 group referring to human RECs treated with both irradiation and KZ-41, respectively. FIG. 3B shows an image depicting the immunoblotting of ICAM-1 extracted human RECs from the same three treatment groups as in FIG. 3A (lower panel) and a graph depicting the quantity of ICAM-1 in the immunoblottings (upper panel). In the graph, the x-axis shows the three treatment groups. The y-axis shows the percentage of the amount of IAM-1 over the amount of the control group.

In FIG. 4A, the lower panel shows images of immunoblotting following high-dose irradiation (30 Gy) of human RECs at different time points. The upper panel shows a graph depicting the quantities of phosphorylated $p38^{MAPK}$ at different time points. The x-axis has each of the time point. The y-axis is the percentage of the quantitative ratio of phosphorylated $p38^{MAPK}$ over total $p38^{MAPK}$ at each time point in comparison to the quantitative ratio phosphorylated $p38^{MAPK}$ over total $p38^{MAPK}$ at time point zero. In FIG. 4B, the lower panel shows images of immunoblotting in three groups of human RECs: control group referring to human RECs without irradiation or KZ-41 treatment; irradiation group referring to human RECs treated with irradiation (30 Gy) for 4 hours; and IR+KZ-41 group referring to human RECs treated with both irradiation (30 Gy) for 4 hours and KZ-41, respectively. The upper panel shows a graph depicting the quantities of phosphorylated P38 in the three groups of human RECs. The x-axis shows each of the three treatment groups. The y-axis shows the percentage of the quantitative ratio of phosphorylated P38 over total P38 in each group in comparison to the quantitative ratio phosphorylated $p38^{MAPK}$ over total $p38^{MAPK}$ in the control group. In both FIGS. 4A and 4B, $P-p38^{MAPK}$ refers to phosphorylated $p38^{MAPK}$ protein; Total $p38^{MAPK}$ refers to both phosphorylated and unphosphorylated $p38^{MAPK}$ protein; and α-Tubulin refers to the normalization control protein α-Tubulin.

FIGS. 5A, 5B, 5C, 5D, and 5E show images and graphs depicting the results of assays of p53 protein and/or phosphorylated p53. FIGS. 5A, 5B and 5C show graphs depicting the expression of p53 with phosphorylated serine at positions 15, 33, 37, respectively. The x-axis shows the three treatment groups: control group referring to human RECs without irradiation or KZ-41 treatment; IR group referring to human RECs treated with irradiation; and IR+KZ-41 group referring to human RECs treated with both irradiation and KZ-41, respectively. The x-axis shows the percentage of the quantitative ratio of phosphorylated p53 over total p53 in each group in comparison to the quantitative ratio of phosphorylated p53 over total p53 in the control group. NS means the difference is not significant. The symbol * means the difference is significantly different. The ratio of the amount of phosphorylation p53 to the amount of total p53 in KZ-41-treated RECs shows no significant reduction (P>0.05). FIG. 5D shows the graph depicting the total p53 protein in the three groups of human RECs (upper panel) and an image of the immunoblotting depicting the expression of the three phosphorylated p53, total p53 and the GAPDH control protein, in the three groups of human RECs (lower panel). In the upper panel graph, the x-axis shows the three groups of human RECs. The y-axis shows the percentage of the quantitative ratio of total p53 over GAPDH in each group normalized to the quantitative ratio of total p53 over GAPDH in the control group. When total p53 protein was normalized to GAPDH, there was a significant reduction in KZ-41 treated RECs (**P<0.05). FIG. 5E shows a graph depicting the total p53 protein in four groups of human RECs (upper panel) and an image of the immunoblotting depicting the expression of total p53 and the GAPDH control protein, in the four groups of human RECs (lower panel). In the upper panel graph, the x-axis shows the four groups of human RECs (from left to right): the first group referring to human RECs without NSC652287 (RITA), KZ-41, and SB 202190 ($p38^{MAPK}$ inhibitor) treatments; the second group referring to human RECs treated with NSC652287 (RITA) only; the third group referring to human RECs treated with both NSC652287 (RITA) and KZ-41; the fourth group referring to human RECs treated with both NSC652287 (RITA) and SB 202190. The y-axis shows the percentage of the quantitative ratio of total p53 over GAPDH in each group normalized to the quantitative ratio of total p53 over GAPDH in the first group.

FIG. 6A shows the graph depicting the amount of cleaved caspase-3 in the three groups of cells by Sandwich ELISA. FIG. 6B shows images of in-cell Western results in the three groups of cells. FIG. 6C shows the graph depicting the cleaved caspase-3 protein amounts detected in the in-cell Western as shown in FIG. 6B. In both FIG. 6A and FIG. 6C, the x-axis shows the three groups of cells and the y-axis shows the percentage of the amount of cleaved caspase-3 in each group over the amount of cleaved caspase-3 in the control group.

FIG. 7A shows a graph depicting the amount of VEGF protein in the human REC culture medium in two groups: control group referring to cells without irradiation treatment and the IR-24 h group referring to cells treated with irradiation ($^{137}$Cs 30 Gy, for 24 hours). The x-axis shows the two groups. The y-axis shows the amount of VEGF in the medium (pg/mL). The symbol * in FIG. 7A means P<0.001. FIG. 7B shows an image of Western blotting (upper panel and a graph depicting the results of the above Western blotting (lower panel) in four groups of human RECs: control referring to cells without irradiation, KZ-41 or SB202190 treatments; IR-24 h group referring to cells treated with irradiation ($^{137}$Cs 30 Gy, for 24 hours); IR+KZ-41 referring to cells treated with irradiation ($^{137}$Cs 30 Gy, for 24 hours) and KZ-41; and IR+SB202190 referring to cells treated with irradiation ($^{137}$Cs 30 Gy, for 24 hours) and SB202190. In the upper panel Western blotting image, p(Y118) refers to phosphorylated paxillin (Y118); paxillin refers to total paxillin including both phosphorylated and unphosphorylated paxillin; and GAPDH refers to the control protein GAPDH. In the lower panel graph, the x-axis shows the four groups of human RECs and the y-axis shows the percentage of the amount of ratio of phosphorylated paxillin to total paxillin in each group in comparison to the ratio of phosphorylated paxillin to total paxillin in the control group. In FIG. 7B, the symbol * means $P<0.01$ and the symbol # means $P<0.05$. FIG. 7C shows a graph depicting the results of REC proliferation assays in three treatment groups: vehicle control referring to cells without any irradiation or KZ-41 treatment; irradiation referring to cells with irradiation treatment; and IR+KZ-41 (10 μM) referring to cells treated with irradiation and KZ-41 with a concentration of 10 μM. In FIG. 7C, the symbol * means $P<0.05$ and the symbol ** means $P<0.05$.

FIG. 8A shows the nanoemulsion composition consisting of Capryol 90 (7.5% v/v), Triacetin (7.5% v/v), Tween-20 (17.5% v/v) and Transcutol P (17.5% v/v) generated via homogenization and water titration methods (left panel) and an image of the solution contained in a tube (right panel). FIG. 8B shows a graph depicting the size of the nanoemulsion particles at day zero. After 60 days at room temperature, the average particle size had increased to 75 nm as shown in FIG. 8C.

FIG. 9 shows a graph depicting the concentration vs. time profile of KZ-41 in both ocular tissue and plasma. The ocular and plasma pharmacokinetic data are listed in the bottom tables. The time points are 0.08 hour, 0.25 hour, 0.50 hour, 1 hour, 4 hour, 8 hour and 24 hour. SD means standard deviation. BLOQ means below the limit of quantification.

FIG. 10A shows images of avascular areas in the four groups of mice (upper panel) and a chart depicting the percentage of avascular areas over total retinal vasculature in the four groups of mice (lower panel). FIG. 10B shows images of neovascular areas in the four groups of mice (upper panel) and the percentage of neovascular areas over total retinal vasculature in the four groups of mice (lower panel). In each group, 5 mice were tested. The percentage data represent mean values (±standard deviations).

FIG. 12A shows a Western Blotting image depicting the expression of phosphorylated Akt protein, total Akt protein, and control GAPDH protein in RECs cultured in high glucose at different times and a graph depicting the ratio of phosphorylated Akt protein versus total Akt protein at different time points. At each time point, three independent samples were assayed. FIG. 12B shows a Western Blotting image depicting the expression of phosphorylated Akt protein and total Akt protein in six groups of REC cells as described in FIG. 11. In each group, 3 cell cultures were performed and assayed. The symbol * means $P<0.05$ versus NG. The symbol # means $P<0.05$ versus HG. All data are presented as mean values±standard deviation.

FIG. 13A shows an image of Western Blotting depicting the expression of phosphorylated Akt, total Akt and control GAPDH protein in REC cells cultured in high glucose (25 mM, HG) pretreated with or without LY294002 (10 μM) for 3 h, then treated with or without KZ-41 (10 μM) for 2 hr. FIG. 13B shows a Western Blotting image depicting the expression of phosphorylated p85, total p85 and control GAPDH in RECs cultured in normal (5 mM) or high glucose (25 mM) and then treated with or without KZ-41 (10 μM) for 2 hours (upper panel), and a graph depicting the results in the Western Blotting image (lower panel). The x-axis shows the four groups of RECs. The y-axis shows the ratio of phosphorylated p85 to total p85 in each group. The symbol * means $P<0.05$ versus NG. The symbol # means $P<0.05$ versus HG. In each group, 3 cell cultures were performed and assayed. All data are represented as mean values±standard deviations.

DETAILED DESCRIPTION OF THE INVENTION

Figure 1:
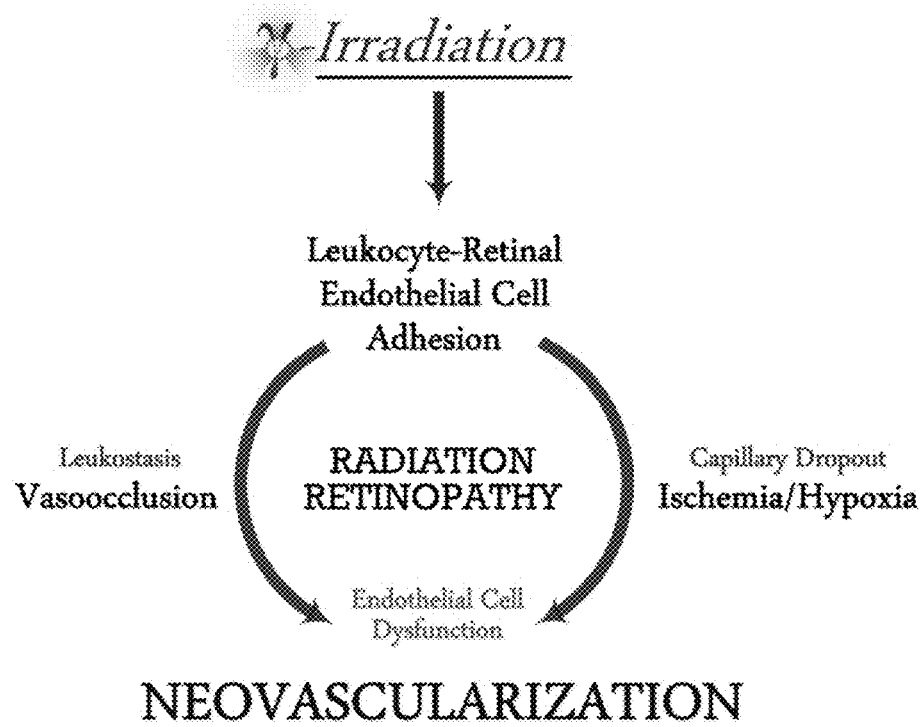
FIG. 1 shows a model where irradiation of the eye triggers leukocyte adhesion, blockage, and nutrient/oxygen deprivation of retinal vasculature. Resultant hypoxia leads to dysfunctional retinal neovascularization and vision loss.

The present invention is partly based on the surprising discovery that a new class of quinic acid analogs (QAAs) can regulate REC viability. The QAAs therefore can be used to therapeutically prevent, treat, or cure pathological conditions associated with RECs of various etiologies, including but not limited to, radiation, chemotherapy or diabetes. One such pathological condition, for example, is retinal neovascularization-caused blindness. The QAAs have been previously described in U.S. Pat. No. 8,115,031 and U.S. Patent Application Publication No. 2012/0283331, both of which are incorporated herein by reference in their entireties.

As such, in one aspect, the present invention is directed to a method for regulating REC viability in a mammal by administering to the mammal a therapeutically effective amount of a QAA compound having a structure as in Formula I.

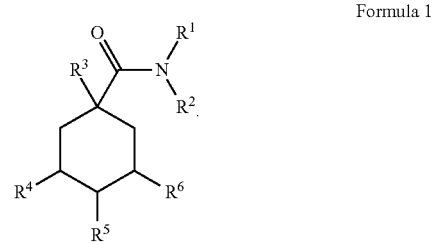

Formula 1

In Formula I, the ring may be singly, doubly, or completely saturated; $R^1$ and $R^2$ are each independently H, straight or branched alkyl, aryl, benzyl, arylalkyl, or heterocyclic amine; $R^3$ may be present or absent and, if present, may be H, hydroxyl, ether, alkoxy, or aryloxy; and $R^4$, $R^5$, and $R^6$ are each independently H, hydroxyl, or alkoxy.

In some embodiments, $R^1$ and $R^2$ in Formula I of the QAA compound form a piperidine ring with Nitrogen (N). In other embodiments, when one of $R^1$ or $R^2$ of Formula I of the QAA compound is hydrogen, the other of $R^1$ or $R^2$ is alkyl. In one instance of the latter embodiments, the compound is a QAA herein named "KZ-41" where the alkyl is —$C_3H_7$ and each of $R^3$-$R^6$ is hydroxyl.

In other embodiments, $R^3$-$R^6$ in Formula I may be an antioxidant with an ester bond in between the antioxidant and the ring. In some instances, only one of $R^3$-$R^6$ is an antioxidant. In other instances, any two of $R^3$-$R^6$ are antioxidants. In still other instances, any three of $R^3$-$R^6$ are antioxidants. In still other instances, all $R^3$-$R^6$ are antioxidants. Antioxidants may a naturally occurring antioxidant, including, but not limited to, caffeic acid, ferulic acid, and sinapic acid. In one embodiment, the antioxidant is a caffeic acid which is connected through an ester bond to the ring at anyone of the positions $R^3$-$R^6$.

QAAs may be synthesized by methods as previously described in U.S. Pat. No. 8,115,031. Alternatively, QAAs may be isolated from a variety of plant extracts, such as Cat's Claw extract. Methods of isolation are known in the art (Akesson et al., 2005; Sheng et al., 2005).

In some embodiments, the mammal may be any mammal that needs treatment for pathological conditions associated with retinal endothelial cells. In some preferred embodiments, the mammal is a human and the method of administering QAAs is used to promote viability of RECs in anticipation of or post-ocular insults.

In some embodiments, QAAs may be administered in a pharmaceutical composition containing the compound in combination with other chemical components such as physiologically suitable carriers and excipients in order to facilitate administration of QAAs to a target site. Such pharmaceutical compositions can be prepared by methods and contain excipients which are well known in the art. Such methods and ingredients may be found in Remington's Pharmaceutical Sciences (Alfonso Gennaro et al., eds., Lippincott, Williams & Wilkins, Baltimore, Md., 20th ed., 2000).

For example, a pharmaceutically acceptable carrier may be a carrier, an adjuvant or a diluent that does not cause significant irritation to an organism and does not abrogate the biological activity and properties of the administered compound. An excipient may be an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Proper formulation of QAA is dependent upon the route of administration chosen. For example, as described in Example 1, QAA may be formulated in nanoemulsion so that QAA may be delivered to the retinal cells topically as an eye-drop.

Suitable routes of systematic administration of QAA may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections. Alternately, one may administer QAA in a local rather than systemic manner, for example, via injection of the pharmaceutical composition directly into a tissue region of a patient, for example, the eye.

A therapeutically effective amount is an amount of QAA necessary to achieve the desired endpoint. One desired endpoint, for example, is to prevent the occurrence of REC death following radiation therapy of ocular tumor, chemotherapy of retinoblastoma, or exposure of eye to high glucose. Additional desired endpoints may, for example, include decreased expression of proteins such as cleaved caspase-3 and ICAM-1 that are associated with apoptosis of RECs. Still additional desired endpoints may for example, include phenotypes such as decreased avascular area or neovascular areas, or decreased apoptosis of RECs.

Assessment of a therapeutically effective amount is well within the skill of one in the medical and pharmaceutical arts, given the disclosure herein. For example, the U.S. Department of Health and Human Services Food and Drug Administration Center for Drug Evaluation and Research (CDER) has established guidance for estimating dosages (*Guidance for Industry: Estimating the Maximum Safe Starting Dose in Initial Clinical Trials for Therapeutics in Adult Healthy Volunteers*, July 2005).

Therapeutically effective doses may be achieved via administration of a single dose, but may also be achieved via administration of more than one dose, such as an initial dose in combination with one or more additional doses which may be provided within a specific timeframe, for example, such as within about 12 to about 72 hours after the initial dose.

QAA may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

In one embodiment, QAA is used to prevent, treat or cure radiation retinopathy. Radiation retinopathy (RR) is a chronic degenerative disease that leads to significant visual impairment (Giuliari et al., 2011). RR results from exposure of the eye to various directed radiotherapy interventions (e.g., external beam, plaque brachytherapy, and gamma knife) (Egger et al., 2001; Finger et al., 2009; Haas et al., 2002; Krema et al., 2009; Witt, 2003). Radiotherapy is increasingly used to treat intraocular tumors since it provides equivalent or enhanced survival compared to enucleation (eye removal) (Diener-West et al., 2001; Jampol et al., 2002; Phillpotts et al., 1995). The incidence of proliferative (i.e., neovascular) RR was recently reported as 7% at ten and fifteen years in 3,841 eyes treated with plaque radiotherapy for uveal melanoma while overall estimates of RR incidence are as high as 20% (Bianciotto et al., 2010; Gunduz et al., 1999). Patients that consequently undergo secondary enucleations, in spite of successful radiotherapy, do so because of extensive retinal vascular damage. Severe pain and/or vision loss associated with lesions, inflammation, thrombosis, and neovascularization were present in a majority of these cases (Avery et al., 2008).

Radiation-induced damage to the vascularized posterior retinal segments of the eye triggers an exuberant pro-inflammatory response resulting in leukocyte adhesion/stasis, vessel occlusion, retinal endothelial cell (REC) death, and subsequent hypoxia (Cai et al., 2004; Johnston et al., 2003; Olthof et al., 2001). The ischemic state within the retina trigger growth-factor mediated neovascularization, secondary to the initial radiation injury. Hallmark vision-threatening cytopathological features of retinal inflammation are vascular leakage and capillary non-perfusion, contributed in large part to the accumulation of immune cells in the damaged areas (Miyamoto et al., 1999). Thus, this breakdown and compensatory neovascularization within the highly vascularized retina leads to blindness. The term "radiation" means "ionizing radiation." examples of ionizing radiation including, but not being limited to, gamma-radiation sources and x-rays.

In another embodiment, QAA is used to prevent, treat or cure side effects caused by chemotherapy of retinoblastoma. Retinoblastoma is the most common primary intraocular malignancy in children. With treatment, greater than 90% of patients in developed countries live. However, to improve the quality of life of these cancer survivors, newer treatments using localized chemotherapy have been developed in hopes of better salvaging eyes and vision. Selective ophthalmic artery chemotherapy was first developed by Kaneko in the 1980's using a balloon occlusion of the carotid artery to selectively deliver chemotherapy to the ophthalmic artery (Pham et al., 2012; Yamane et al., 2004). Subsequently, Abramson modified Kaneko's approach by directly delivering melphalan, a nitrogen mustard, into the ophthalmic artery under manual control without balloon occlusion, a technique termed super-selective intra-ophthalmic artery chemotherapy (SSIOAC) (Abramson et al., 2008; Gobin et al., 2011). While SSIOAC may be more effective than systemic chemotherapy for specific cases, recent data indicates that a number of significant side effects to the retinal and choroidal vasculature can occur following SSIOAC with melphalan (Munier et al., 2011; Shields et al., 2011; Wilson et al., 2011). For example, melphalan SSIOAC administered to non-human primates (NHPs), in the same manner as given to children, produced retinal vascular inflammation, manifested as increased leukocyte adhesion, and occlusion. (Steinle et al., 2012). As such, in some embodiments, QAA is administered to prevent, treat, or cure the side effects caused by chemotherapy of retinoblastoma. These side effects include retinal vascular inflammation, which can lead to choroidal vasculature, neovasculature, retinal endothelial cell death and eventually blindness. For instance, as shown in Example 3, KZ-41 may be administered to protect retinal endothelial cells against melphalan-induced damage without affecting the apoptosis of melphalan-treated human retinoblastoma cells.

In some embodiments, QAA administrations may start prior to radiation therapy or chemotherapy, and continue during radiation therapy or chemotherapy, and then after radiation therapy or chemotherapy until the risk of radiation therapy or chemotherapy-induced damage is minimal. In other embodiments, QAA administrations may start in conjunction with radiation therapy or chemotherapy, and then continue after radiation therapy or chemotherapy. In still other embodiments, QAA administrations may start after radiation therapy or chemotherapy. Depending whether pathological conditions have occurred when QAA is administered, QAA is used to prevent, treat or cure the pathological conditions caused by radiation therapy or chemotherapy.

In yet another embodiment, QAA is used to prevent, treat or cure diabetic retinopathy. Diabetic retinopathy (DR), one of the most frequently occurring microvascular complications of diabetes, is a leading cause of visual loss in patients aged 20-74 years (Bassoli et al., 2008; Marshall and Flyvbjerg, 2006). Numerous investigations have suggested that the pathogenesis of diabetic retinopathy includes glucose-mediated anatomic changes in retinal vessels (Engerman, 1989). Blood retinal barrier issued vascular leakage and pre-retinal neovascularization are key clinical features of DR. Hyperglycemia triggers caspase-dependent apoptosis in retinal endothelial cells, which is followed by a compensatory angiogenic response to replace lost cells (Geraldes et al., 2009). The cycle of accelerated REC death and renewal is thought to contribute to vascular architectural changes and, upon exhaustion of the replicative life. Laser photocoagulation to reduce neovascularization and macular edema has been the mainstay of treatment for proliferative diabetic retinopathy (PDR) more than 25 years. However, it is a destructive therapy, with adverse side effects such as loss of peripheral visual filed and night vision as well as exacerbation of macular edema and subsequent reduction of central vision (Shimura et al., 2003). Therefore, it is imperative to develop new identification, treatment options to treat retinopathy in the earliest stages.

As such, in some embodiments, QAA is administered to prevent, treat or cure the vascular complications and subsequent visual loss caused by exposure to high glucose. In some instances, QAA administrations may start before any symptoms of diabetic retinopathy occur so that the occurrence of diabetic retinopathy may be postponed, delayed, or prevented. In other instances, QAA administrations may start after symptoms of diabetic retinopathy occur so that diabetic retinopathy may be prohibited from further exacerbation or the exacerbation may be delayed or postponed.

The common pathological conditions caused by radiation therapy, high glucose exposure or chemotherapy include retinal endothelial cell death ("REC death") which in turn results in retinal neovascularization in the retina. As such in some embodiments, QAA is administered to regulate the viability of retinal endothelial cells so that REC death caused by various ocular insults may be prevented or reduced. In other embodiments, QAA is administered to regulate the viability of retinal endothelial cells so that retinal neovascularization caused by various ocular insults may be prevented or reduced.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It should be understood that this invention is not limited to the particular methodologies, protocols and reagents, described herein, which may vary. The terminology used herein is for the purpose of describing particular embodiments only, and is not intended to limit the scope of the present invention.

Examples of the disclosed subject matter are set forth below. Other features, objects, and advantages of the disclosed subject matter will be apparent from the detailed description, figures, examples and claims. Methods and materials substantially similar or equivalent to those described herein can be used in the practice or testing of the presently disclosed subject matter. Exemplary methods and materials are now described as follows.

Example 1

KZ-41 could Regulate Retinal Endothelial Cell Viability in Connection with Radiation Retinopathy In this Example 1, we demonstrated that KZ-41 could be used to regulate retinal endothelial cell viability in both in vitro and in vivo models of RR. We discovered that KZ-41 functioned by modulating these inflammatory elements in primary RECs acutely exposed to ionizing radiation (IR). The attenuation of inflammatory responses triggered by high-dose irradiation by KZ-41 suggested that KZ-41 treatment can be used as a pre-exposure prophylactic measure to limit and/or prevent pathological precursors of RR (i.e., retinal vascular inflammation).

The materials and methods we used in this example are as follows.

Reagents/Antibodies.

KZ-41 was synthesized in Dr. Duane Miller's laboratory and verified to be >96% pure by nuclear magnetic resonance spectroscopy (Zeng et al., 2009). Calcein-AM was obtained from BD Biosciences (San Jose, Calif.). Conjugated ICAM-1 (sc-107 PCPC5) and P-selectin (sc-19672 FTIC) antibodies for confocal microscopy were purchased from Santa Cruz Biotechnology (Santa Cruz, Calif.). DAPI nuclear stain was obtained from Pierce (Rockford, Ill.). Phosphorylated (Thr180/Tyr182) p38MAPK primary antibodies were purchased from R&D Systems (Minneapolis, Minn.). Phosphorylated (Ser-15, -33, -37) and total p53, p38MAPK, unconjugated ICAM-1, phosphorylated (Tyr118) and total paxillin, and GAPDH primary antibodies were acquired from Cell Signaling (Danvers, Mass.). Alpha-Tubulin primary antibody and secondary antibodies, IRDye 800CW goat anti-rabbit and IRDye 680LT goat anti-mouse were purchased from LI-COR Biotechnology (Lincoln, Nebr.). SB202190 and NSC652287, inhibitors of p38$^{MAPK}$ and p53-MDM2, respectively were purchased from Tocris Bioscience (Bristol, UK).

Cell-Culture.

Primary human retinal microvascular endothelial cells (REC, Lot 181) were provided by Cell Systems Corporation (CSC, Kirkland, Wash.). Cells were grown on gelatin-coated surfaces in M131 medium containing microvascular growth supplements (MVGS) (Invitrogen; Carlsbad, Calif.), gentamycin (10 mg/mL), and amphotericin B (0.25 mg/mL). Only primary cells within passage 6 were used. For immunoassays, RECs were plated into six-well plates and cultured for two days. RECs were pretreated with KZ-41 (10 µM) for 12 hours and then exposed to gamma (γ)-rays (30 Gy) using a Shepherd Mark I, model 68, 137Cs irradiator (J.L. Shepherd & Associates, San Fernando, Calif.) at a dose rate of approximately 3 Gy/min. To investigate cell signaling through p38$^{MAPK}$, SB202190 was added to culture medium 30 minutes prior to IR. U937 (human monocytic-like) cells (ATCC, Manassas, Va.) were cultured in RPMI 1640 (Invitrogen) supplemented with 10% fetal bovine serum, penicillin (5000 IU) and streptomycin (5 mg/mL). Cells to passage 10 were used for adhesion experiments.

Static Cell Adhesion.

Cellular adhesion under static conditions was assessed using a microplate assay as previously described (Chang et al., 2010; Yu et al., 2007). Briefly, human primary RECs (105 cells/well) were seeded to 96-well plates and cultured to a confluent monolayer. RECs were treated with either KZ-41 (10 µM) or vehicle (0.9% normal saline), irradiated at 30 Gy and incubated for 24 hours at 37° C. Calcein-AM loaded U937 cells were added to REC-containing wells and allowed to adhere for 30 minutes. Non-adherent cells were removed from wells by gentle washes and adhesion was quantified using a fluorescence microplate reader (excitation/emission wavelengths of 485/535 ηm). Data represent mean fluorescence±standard deviation (SD) normalized to background fluorescence.

Parallel-Plate Flow Chamber.

Cell adhesion under physiological fluid-shear was investigated using a parallel-plate flow chamber and continuous flow-loop (Cytodyne Inc., La Jolla, Calif.) at a shear stress of 2 dyne/cm2 (Lawrence et al., 1987; Steinle et al., 2012; Wagers et al., 1998). Shear stress within the chamber was determined using a constant fluid flow-rate calibrated by adjusting the height of the hydrostatic inlet and outlet ports of the fluid reservoir (Frangos et al., 1988; Wagers et al., 1998). The flow rate for the required shear stress was calculated using the following equation: SS=6Qµ/bh2, where SS=shear stress (dyne/cm2), Q=flow rate (cm3/s), µ=fluid viscosity (dyne*s/cm2), b=chamber width (cm), h=chamber height (cm). RECs were seeded onto gelatin-coated microscope slides (75×38 mm; Corning Inc., Corning, N.Y.) and grown to confluence. KZ-41 (10 µM) or vehicle-treated RECs were irradiated at 30 Gy and incubated for 24 hours. Slides were then placed into the chamber and U937 (human monocytic) cells (2.5×10$^6$ cells/mL) were perfused over the REC monolayer. Interacting monocytes were monitored over two hours using at least eight different fields of view and digitally recorded for off-line analysis. Phase contrast images of U937 cells adhering to human REC monolayers were obtained using a Nikon Diaphot 300 phase-contrast microscope (Nikon, Melville, N.Y.) equipped with a Dage-MTI series 68 camera (Dage-MTI, Michigan City, Ind.). High-resolution video and images were analyzed using Adobe Premier Pro CS5.5 (Adobe Systems, Inc., San Jose, Calif.). Firm adhesion was defined as interacting monocytes remaining stationary at each 30-minute increment (Alon et al., 1996; McCarty et al., 2000). After two hours, RECs were removed from the flow chamber and fixed in 4% formaldehyde for 15 minutes at room temperature and washed three times with ice-cold phosphate-buffered saline (PBS). Data from three separate experiments represent mean adherent cells/field of view over 30 minute increments±SD.

Confocal Microscopy.

Non-specific blocking of proteins on cellular surface was done using 10% bovine serum albumin (BSA) containing blocking buffer for at least one hour at room temperature. Human anti-ICAM-1 and anti-P-selectin antibodies conjugated to PerCp-Cy5.5, FITC respectively were diluted in PBS (1:50) and incubated with the slide for one hour at room temperature with gentle rocking Slides were then washed twice with cold PBS and incubated with DAPI nuclear stain for 10 minutes. Cells were again washed and mounting medium along with cover slips were added to slides and sealed prior to imaging. A Zeiss LSM 710 system with Zen 2010 v.6.0 software (Carl Zeiss Microscopy, LLC, Thornwood, N.Y.) was used in acquisition and analysis of RECs. Adobe Photoshop CS5 (V. 12.1; Adobe Systems, Inc.) was used to measure relative intensities of confocal images. All images were normalized to cell number. Data represent mean intensity signals±SD.

Immunoblot (Western) Analysis.

Irradiated RECs with or without treatments of either KZ-41 and/or inhibitors of p38$^{MAPK}$ were carried out at 30 Gy. For ICAM-1 protein level analysis, REC lysates were collected 24 hours after IR. For phosphorylation status of MAPK and p53 stress pathways, REC lysates were collected 4 hours following exposure to IR. Unirradiated RECs were taken out of the incubator during irradiations for environmental controls. Cellular proteins were analyzed by Western blot after SDS-PAGE using human specific primary antibodies. REC lysates were collected in RIPA lysis buffer (50 mM Tris.HCl, pH 7.4, 150 mM NaCl, 2 mM EDTA, 1% Nonidet P-40, 0.1% SDS) with protease/phosphatase inhibitor (1×) cocktail (Roche; Indianapolis, Ind.). Lysates were kept on ice and centrifuged at 10,000 g for 10 minutes and total protein was measured using BCA assay (Pierce, Rockford, Ill.). Protein samples were mixed with 4×LDS loading buffer with 2.5% 2-mercaptoethanol (Sigma), heated to 70° C. for 10 minutes, and loaded on NuPAGE 4-12% Bis-Tris gel (Invitrogen). Immunoblotting was performed with nitrocellulose membranes (Bio-Rad) at 170-mA start and 110-mA end at 25 V for 2 h in NuPAGE transfer buffer (Invitrogen) containing 20% methanol. Membranes were blocked using Odyssey blocking buffer (LICOR) for 1 h at room temperature with gentle rocking Membranes were then incubated at 4° C. with specific primary antibodies (1:1000) overnight. Cellular protein was normalized using GAPDH (Cell Signaling) or α-Tubulin (LI-COR) [1:20,000]. Secondary antibodies (IRDye 800CW goat anti-rabbit and IRDye 680LT goat anti-mouse) (LI-COR) [1:10,000] were incubated in the dark at room temperature for 45 minutes. Dual-channel infrared scan and quantitation of immunoblots were conducted using the Odyssey® Sa infrared imaging system with Image Studio (Ver. 3.1.4) (LI-COR).

Cleaved Caspase-3.

In-Cell Western blotting (ICW) was used to quantitatively measure the presence of cleaved caspase-3 protein within intact cells. Briefly, RECs were seeded into a 96 well plate and cultured for one day. Cells were irradiated at 30 Gy and returned to incubator for 24 hours. Cells were then fixed with 4% paraformaldehyde for 15 minutes with gentle shaking and washed five times with PBS containing 0.1% Triton X-100 solution. Odyssey blocking buffer was added to each well and incubated at room temperature for one hour. Cleaved caspase-3 primary antibody (Cell Signaling) was diluted in blocking buffer (1:50) and incubated at 4° C. overnight with gentle shaking Wells were then washed with 0.1% Tween-20 in PBS solution five times. IRDye 800CW goat anti-rabbit secondary antibody (1:1000) was added along with DRAQ5 (Biostatus, Leicestershire, UK) counterstain for cell-number normalization. Cells were washed five more times with washing buffer and plates were imaged using the Odyssey Sa imaging system (LI-COR). Data represent background-normalized mean fluorescence intensity±SD (n=12/group). The Pathscan Cleaved Caspase-3 sandwich ELISA kit (Cell Signaling) was performed to evaluate endogenous caspase-3 activation 24 hours post-irradiation. Briefly, cells were irradiated at 30 Gy and incubated for 24 hours in the presence or absence of KZ-41. Lysates of equivalent total protein were used for ELISA analysis. Assay was performed based on manufacturer's protocol. Data represent mean O.D.±SD.

VEGF-ELISA and REC Proliferation Assay.

ELISA assays were used to measure changes in protein levels of VEGF (Quantikine, Minneapolis, Minn.) Briefly, confluent RECs were irradiated at 30 Gy and incubated at 37° C. for 24 hours; Medium was collected and analyzed according to manufacturer's instructions. For all ELISA analyses, equal protein amounts were loaded into each well, allowing for comparisons using optical density (OD).

To evaluate KZ-41 modulation of irradiation-induced retinal endothelial cell proliferation 50,000 cells with or without KZ-41 (10 μM) were plated into each well of a 96-well dish, irradiated at 30 Gy and incubated for 24 hours. Following treatment with KZ-41 or vehicle, cellular proliferation was determined using tetrazolium salt WST-1 and a microplate reader (UQuant Reader; BioTek, Winooski, Vt.) according to the assay manufacturer's instructions (Cell Proliferation Assay Kit, WST dye, ELISA based; Millipore, Billierca, Mass.) at 450 nm. The absorbance at 450 nm (recorded in Mean OD±SD) is directly correlated with cellular proliferation.

Nanoemulsion Formulation/Characterization and Ocular Pharmacokinetics.

Ocular nanoemulsion (NE) used for drug delivery was comprised of Capryol 90 (7.5% v/v), Triacetin (7.5% v/v), Tween-20 (17.5% v/v) and Transcutol P (17.5% v/v) (Gattefossé Pharmaceuticals, Saint-Priest, France) generated via homogenization and water titration methods, as previously described (Ammar et al., 2009; Shafiq-un-Nabi et al., 2007). Characterization of the NE was done using an AR G2 Rheometer (TA Instruments, New Castle, Del.), Malvern Zetasizer (Malvern Instruments Ltd, Malvern Worcestershire, UK), and Fisher Accumet Excel pH meter (Thermo Fisher Scientific, Waltham, Mass.). KZ-41 loaded NE was delivered to the eye for ocular PK studies at 100 mg/kg dose using standard pipetting techniques.

Male C57BL/6J (The Jackson Laboratory, Bar Harbor, Me.) mice weighing ~25 g were used for ocular administration of KZ-41 in NE. Animals (n=3) were sacrificed using cardiac puncture methods at specified time points between 5 minutes and 24 hours. Whole blood was separated via centrifugation, and plasma was collected. Eyes were enucleated, irrigated with normal saline and homogenized to obtain compound from ocular chambers. Drug concentrations in both plasma and in the eye were stored at −80° C. until analysis. KZ-41 plasma and ocular samples were processed and drug concentrations were determined using LC-MS/MS, as previously described (Ramagiri et al., 2009; Zeng et al., 2011). KZ-41 plasma and ocular drug concentration-time data was analyzed using noncompartmental methods in WinNonlin 6.0 (Pharsight, Mountain View, Calif.).

Animals and Experimental Design of Oxygen-Induced Retinopathy (OIR) Murine Model.

C57BL/6J mice were used in these experiments. All animal experimentation was performed under the guidelines of the Association for Research in Vision and Ophthalmology for the humane use of animals in vision research, and in accordance with our established institutional guidelines. Mouse pups were divided into four separate groups: 1) Untreated mice under ambient normal oxygen (normoxia) conditions (negative-control); 2) Untreated mice exposed to hyperoxia conditions (positive-control); 3) Nanoemulsion vehicle treated hyperoxia-exposed mice (vehicle-control); and 4) Hyperoxia-exposed mice treated with KZ-41-loaded nanoemulsion (compound-treated). A minimum number of 5 animals were used for each experimental group.

Retinal neovascularization (RNV) was induced using a mouse model of oxygen-induced retinopathy (OIR). Briefly, C57BL6/J mouse pups were exposed to 75% oxygen at post-natal day 7 (P7) for 5 days and then returned to normal oxygen (P12). OIR mice received daily ocular administration of either KZ-41 (100 mg/kg), vehicle (ocular nanoemulsion) or left untreated from P12 to P17. Normoxia (negative controls) mice were not manipulated during the study period. Retinas from all pups were removed, dissected, mounted and stained to investigate retinal angiogenesis as previously described (Arnold et al., 2012; Connor et al., 2009). For retinal whole mounts, enucleated eyes underwent weak fixation (for ease of hyaloid vasculature removal) in 4% paraformaldehyde (PFA) in PBS for 1 h on ice and washed three times. Retinas were then isolated and mounted onto microscope slides. Whole retinas were incubated overnight at 4° C. with isolectin B4-594 (Alexa Fluor 594; Molecular Probes, Eugene, Oreg.). Isolectin-stained retinas were then washed three times in 1×PBS, sealed on slides using Prolong Gold (Invitrogen) and imaged.

Images were acquired using a Nikon Eclipse 80i confocal microscope and analyzed with Nikon-NIS elements software (Nikon). Quantification of avascular area (AV) and neovascularization (NV) in retinal whole mounts were performed in Adobe Photoshop (Adobe Systems, Inc.) as previously described (Arnold et al., 2012; Connor et al., 2009; Stahl et al., 2010). Briefly, the AV area was determined by the absence of isolectin staining surrounding the optic disc. The area devoid of vascularization was characterized as a percentage of total retinal area (% AV). Quantification of NV was determined after threshold limits are set within software parameters. This technique ensured the quantification of only clusters and tufts of NV while excluding the normal vascularized retina (less intense staining) Photoshop analysis tools were used to manually outline NV formations and data was recorded as a percentage of total retinal area (% NV) (Arnold et al., 2012; Connor et al., 2009).

Statistical Analyses.

All data represented herein were performed in replicates of 3 or more and presented as the mean±standard deviation (SD), unless otherwise indicated. Analysis of variance (ANOVA) with Scheffe's post-hoc test was used to compare mean values. Statistical significance was set at $P<0.05$.

Figure 2A:
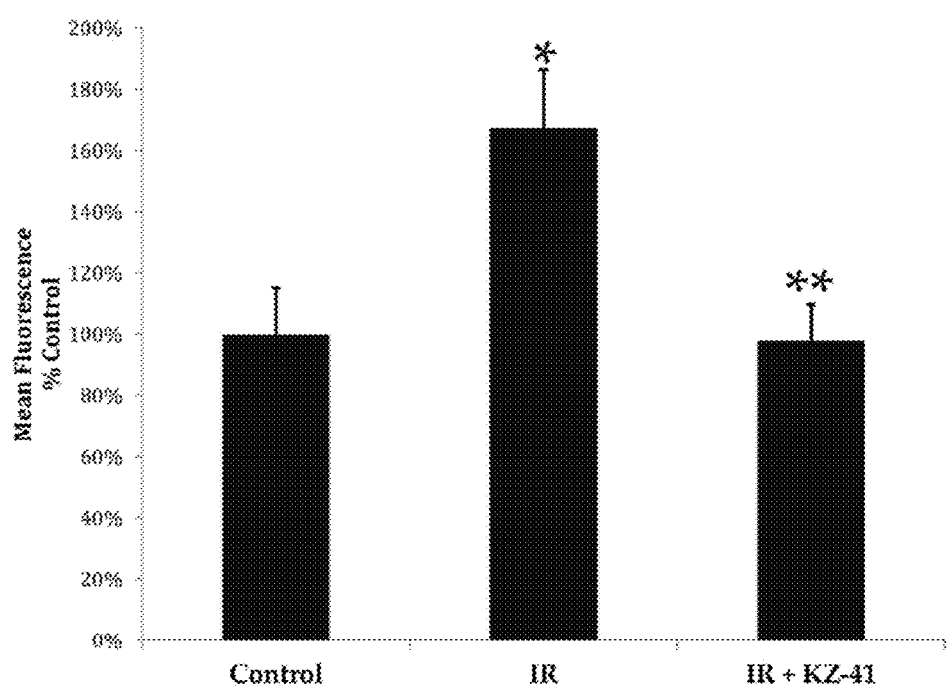
FIGS. 2A and 2B show graphs and images depicting the results of human REC adhesion assays.

We demonstrated herein that irradiation-induced monocyte adhesion to retinal endothelial cells in both static and fluid environments could be attenuated with the treatment of KZ-41. Here, we investigated the acute effects of a single total dose of approximately 30 Gy (~3 Gy/min) delivered in vitro. The rapid induction of ICAM-1 in a variety of endothelial cells is one of major inflammatory indicators of exposure to high-dose radiation (Gaber et al., 2003; Yuan et al., 2003). Using a fluorescent based static-adhesion assay we determined that in response to irradiation, primary human RECs could elicit an inflammatory response via monocyte adhesion. As shown in FIG. 2A, adhesion of U937 monocytic cells was enhanced two-fold in RECs 24 hours post irradiation ($P<0.005$) and RECs treated with KZ-41 immediately prior to radiation experienced a substantial decrease in the number of adhering cells ($P<0.005$).

Figure 2B:
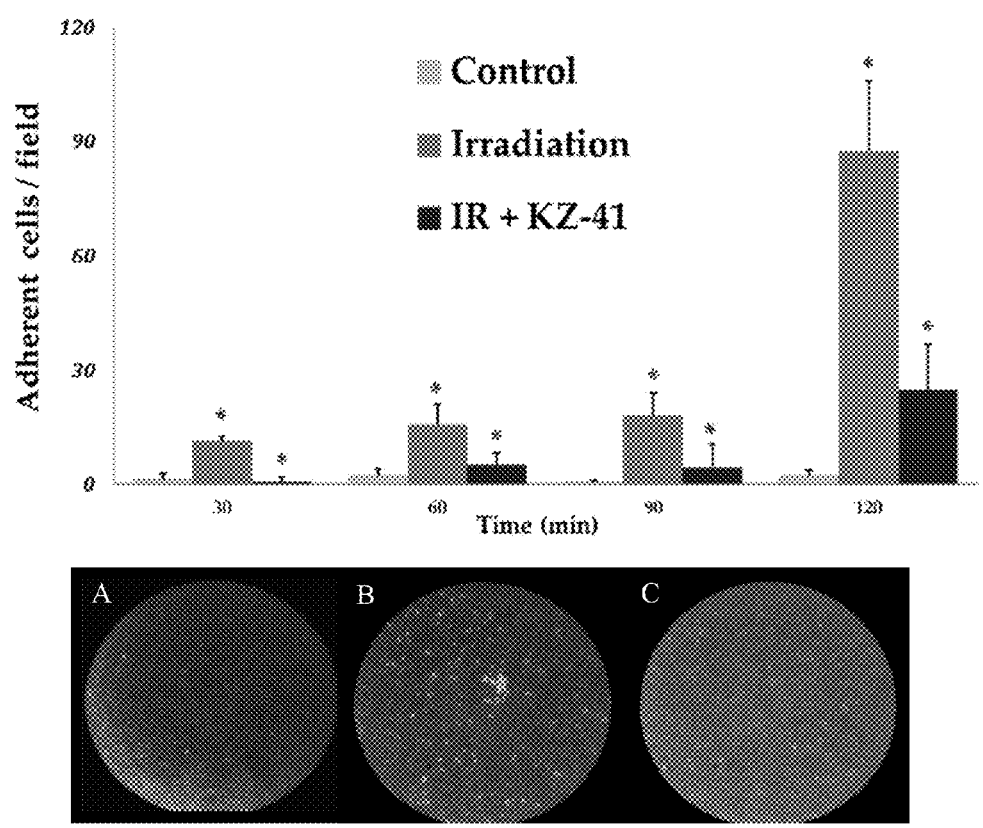

In blood flow, tethering and rolling are initiated by selectins (e.g., L-, P- and E-selectin) which are rapidly presented to the cell surface in response to inflammatory stimuli [37]. Consequently, selectins and other immunoglobin superfamily of cellular adhesion molecules (CAMs; e.g., ICAM, VCAM, PECAM, etc.) are able to perform similar adhesive functions in static environments where the lack of sheer stress promotes adhesive-like interactions (Burns et al., 1999). Therefore, we used a parallel-plate flow chamber and adapted continuous flow-loop (Cytodyne) to establish a perpetual fluid environment of circulating monocytes allowing for the observation and quantification of the three characteristic events: tethering, rolling and firm adhesion (Kinashi, 2005; Ley et al., 2007; Springer, 1995). Twenty-four hours after single dose of 30 Gy, RECs were placed in the flow chamber and interacting U937 monocytic cells were observed and quantified via phase-contrast microscopy. As shown in FIG. 2B (lower panel A-C referring to Control, IR, IR+KZ-41, respectively), upon digital video analysis, rolling, tethering and firm adhesion of monocytes across REC monolayer was significantly enhanced following radiation compared to unirradiated RECs (FIG. 2B, upper panel; 2±2 (A) vs. 87±18 (B) adhered cells; $P<0.05$). In contrast, treatment with KZ-41 in irradiated RECs significantly reduced U937 adherence (25±12 (C) vs. 87±18 (B) adhered cells; *$P<0.05$). Interestingly, rolling activity of monocytes was unaffected with treatment of KZ-41 (observational data not shown).

Figure 3A:
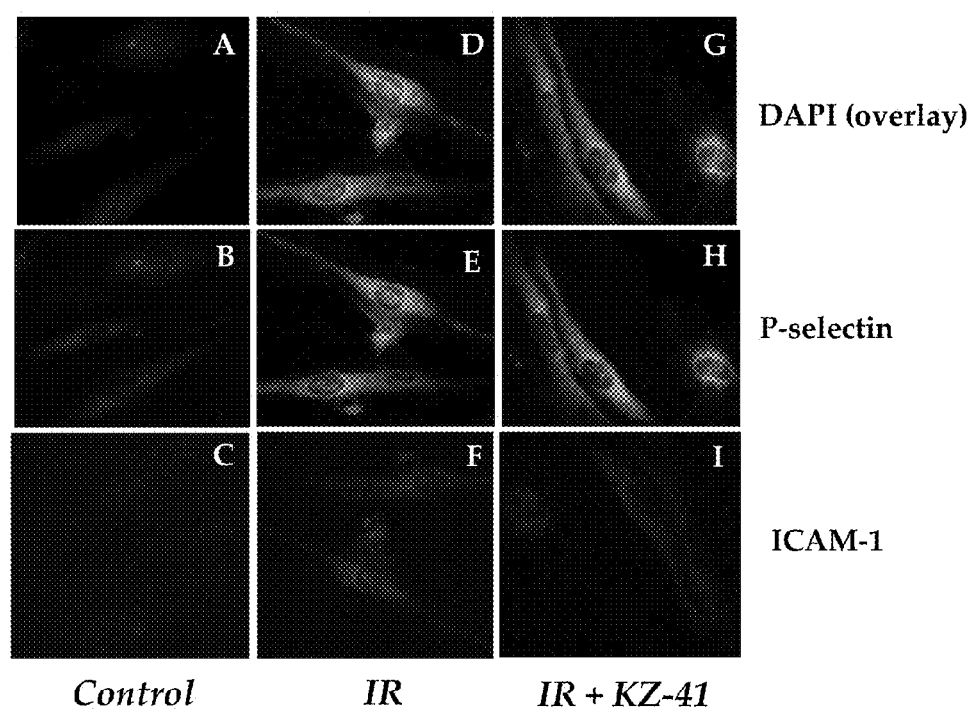
FIGS. 3A and 3B show images and graphs depicting the results of assaying ICAM-1 expression upon KZ-41 treatment.

We demonstrated herein that irradiation-induced ICAM-1 levels could be reduced by KZ-41 treatment. For confirmation that the surface-induction of selectins (specifically P-selectin) was unchanged by treatment of KZ-41 after radiation, we performed confocal microscopy on the same RECs placed in the flow chamber experiments (FIG. 3A). In unirradiated RECs, the level of P-selectin was almost undetectable in stark contrast to very prominent signals shown in irradiated RECs. Both in vitro and in vivo models of radiation-induced vascular injury have established ICAM-1 upregulation as an important pathological indicator of inflammation (Gaber et al., 2003). We examined ICAM-1 expression on the same flow-chamber slides. Within 24 h following irradiation, ICAM-1 levels in irradiated RECs (IR) were increased over unirradiated RECs (control) ($P<0.05$). This increased level (IR) was significantly reduced in KZ-41 treated RECs (IR+KZ-41) ($P<0.05$).

Figure 3B:
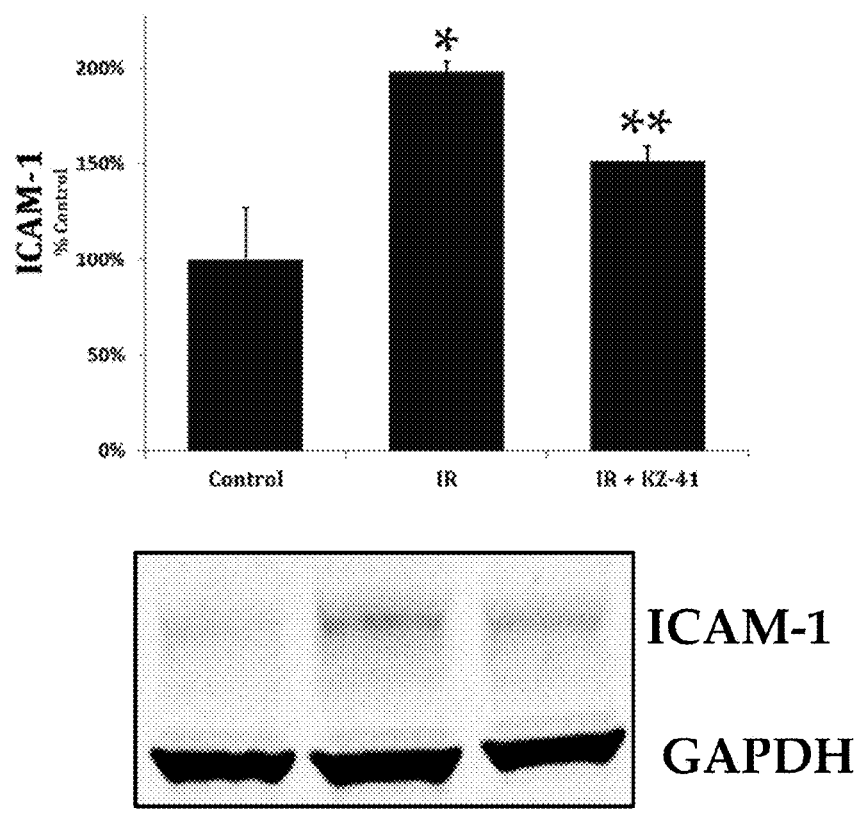

To rule out the possibility that KZ-41 treatment lead to a disruption in rate and/or extent of protein trafficking to cellular surface, we collected cellular lysates of RECs irradiated, with or without treatment of KZ-41 and probed for total ICAM-1 protein by immunoblotting. The total amount of protein that accumulated in the 24 hours following exposure to radiation both on the cell surface and in the cytosolic fraction ($P<0.05$ vs. unirradiated RECs) was reduced with treatment of KZ-41 ($P<0.05$) (FIG. 3B).

Figure 4A:
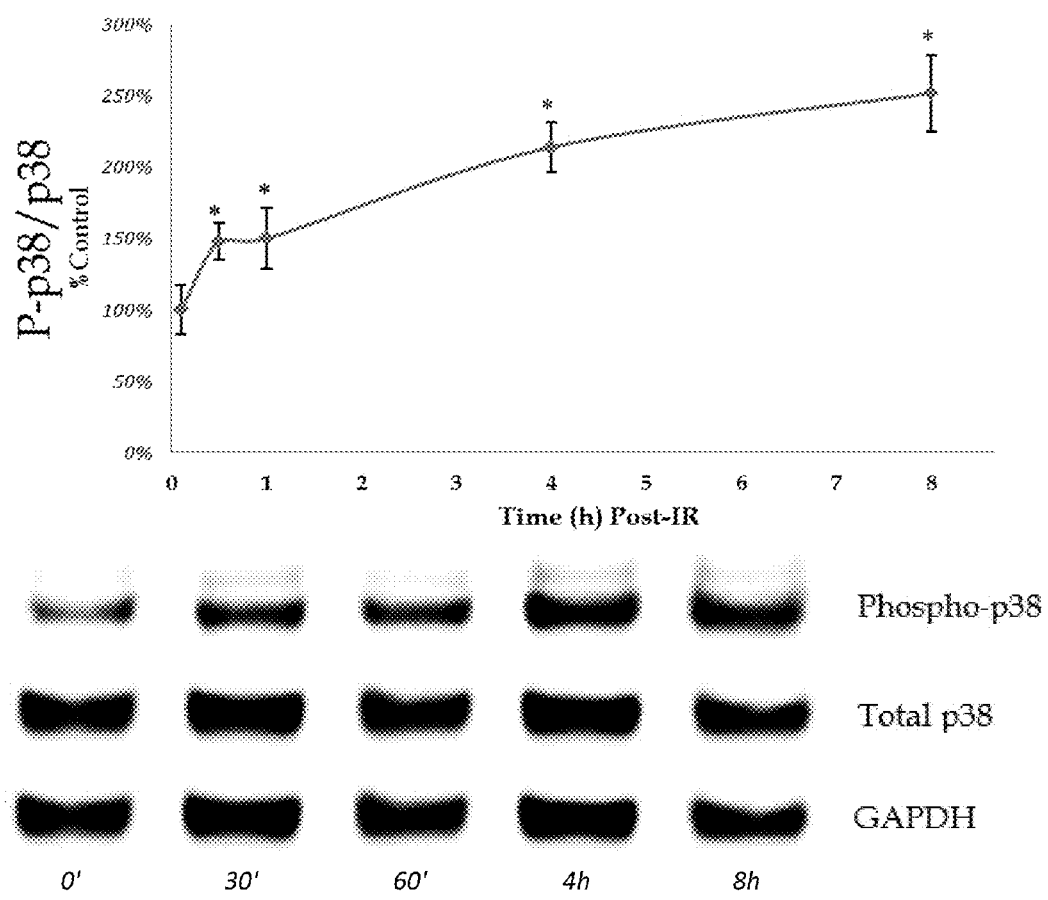
FIGS. 4A and 4B show images and graphs depicting the results of $p38^{MAPK}$ assays in human RECs.
Figure 4B:
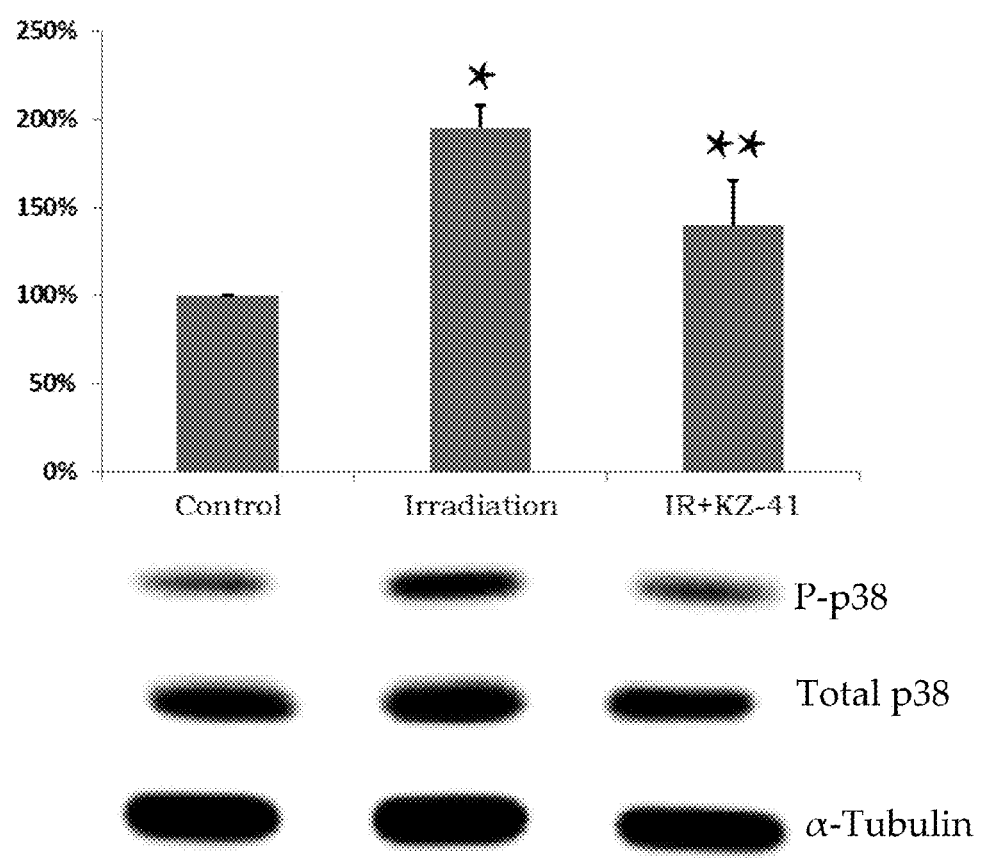

We further demonstrated herein that KZ-41 regulated the ICAM-1 expression levels through a $p38^{MAPK}$-dependent mechanism. We first performed a time-course experiment to examine the $p38^{MAPK}$ phosphorylation status post irradiation. As shown in FIG. 4A, relative to total p38 levels, phospho-p38 reached a transient plateau over four to eight hours post-IR. We then collected and analyzed treated cells 4 hours following irradiation. As shown in FIG. 4B, irradiated RECs that were treated with KZ-41 prior to radiation exposure (IR+KZ-41) had about 30% reduction in phosphorylated $p38^{MAPK}$ (irradiation) ($P<0.05$).

Figure 5A:
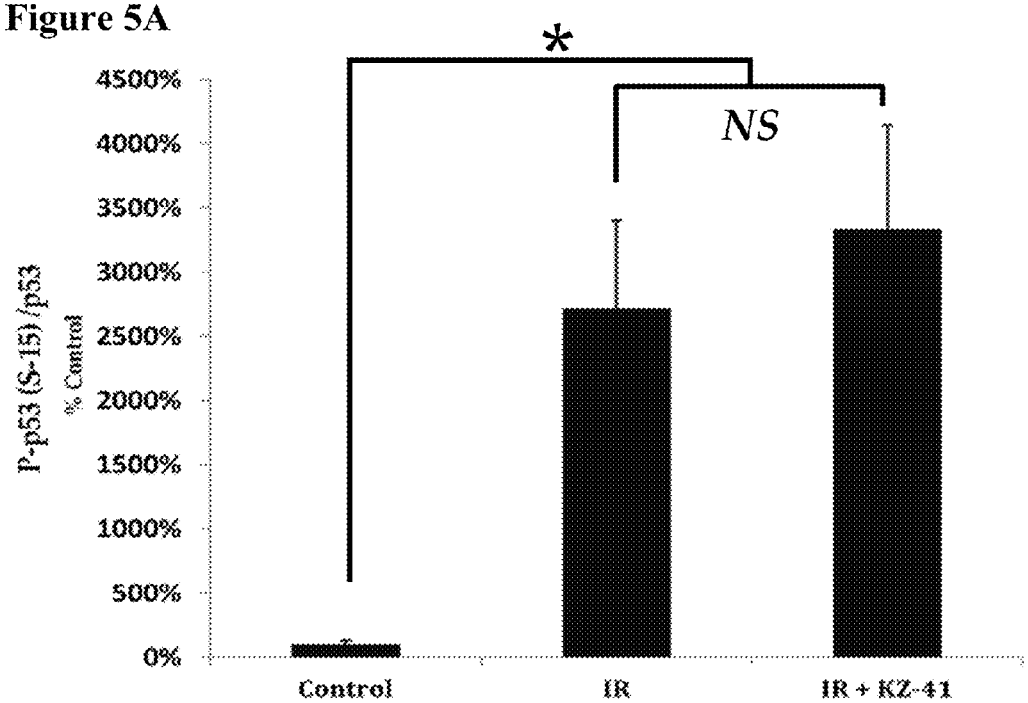
Figure 5B:
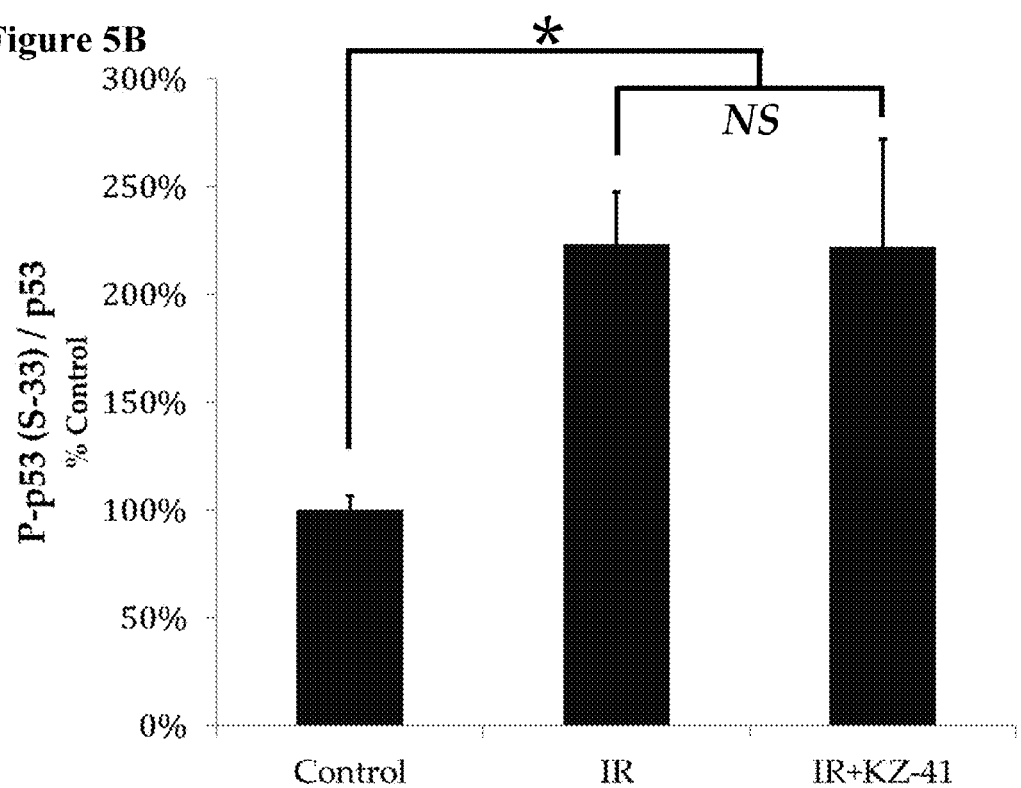
Figure 5C:
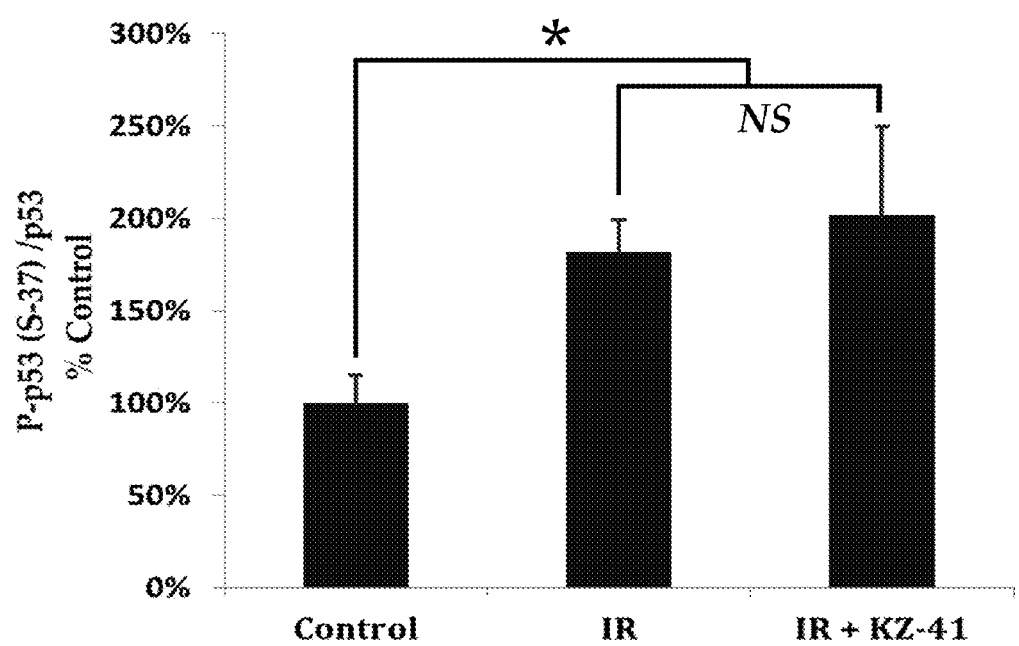
Figure 5E:
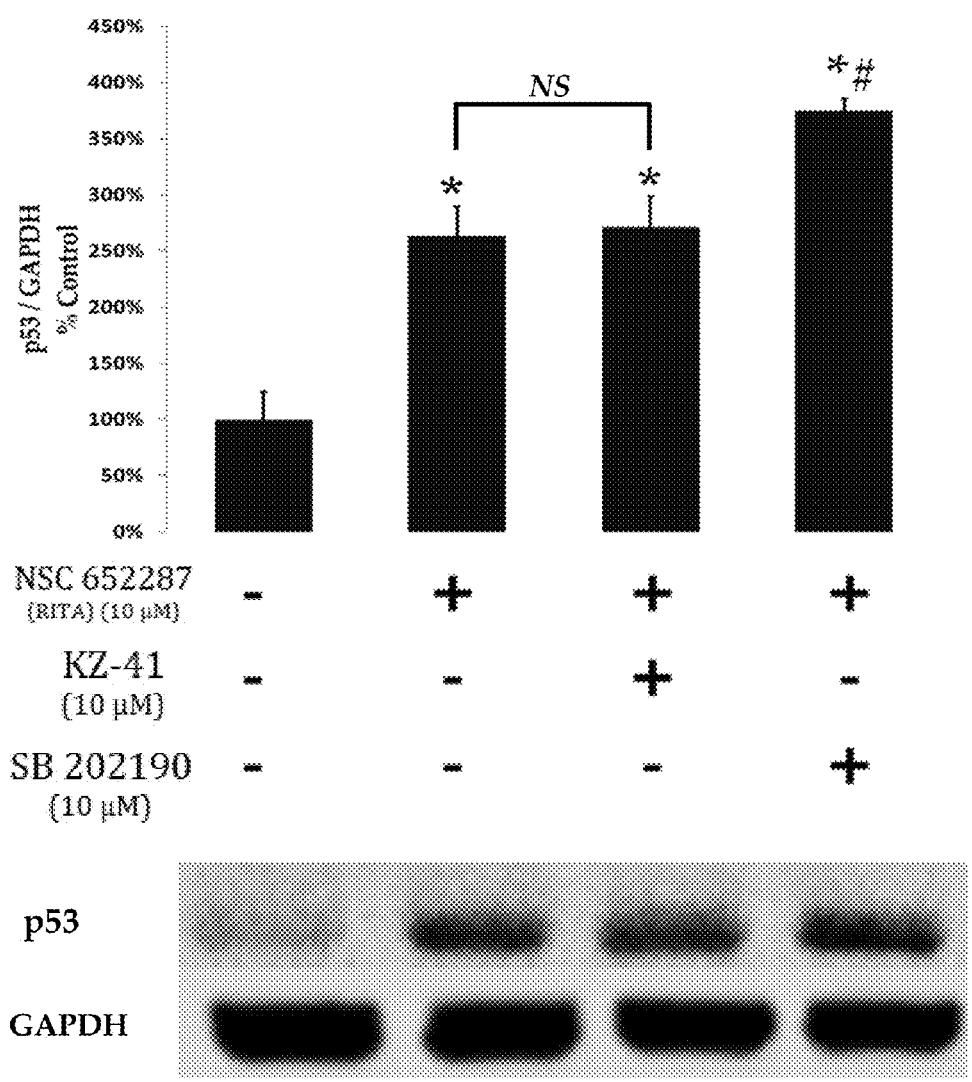

We further demonstrated herein that KZ-41 could increase the stability of p53 although KZ-41 did not cause a significant reduction in phosphorylation of p53 when normalized to total p53 protein. As shown in FIGS. 5A, 5B and 5C, after exposure to radiation, RECs treated with KZ-41 did not show any significant reduction in phosphorylation of p53 when normalized to total p53 protein ($P>0.05$). However, when total p53 was normalized to housekeeping protein, GAPDH, we saw a significant reduction in total p53 protein amount (FIG. 5D, *$P<0.005$, **$P<0.05$). KZ-41 could enhance the stability of p53 protein through the MDM2-mediated ubiquination pathway. RECs were treated with a p53-MDM2 inhibitor, NCS622875 (RITA, 10 µM) that effectively blocks the interaction between MDM2-p53 at the transactivation domain-binding cleft, consequently promoting p53 accumulation (Espinoza-Fonseca, 2005; Parks et al., 2005; Vassilev et al., 2004; Zhong and Carlson, 2005). When compared to untreated RECs, RITA treatment for four hours significantly enhanced p53 accumulation (*P<0.05). In contrast, concomitant treatment with KZ-41 or SB202190 did not significantly alter this occurrence (FIG. 5E, P>0.05).

Figure 6A:
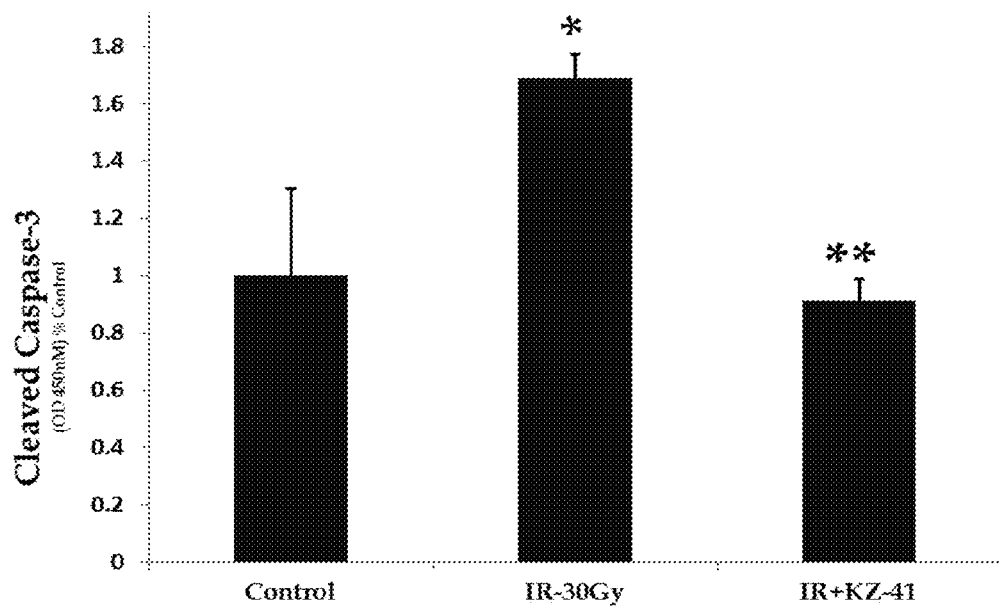
FIGS. 6A, 6B and 6C show graphs and images depicting the results of assays of cleaved caspase-3 in three groups of human RECs: control group referring to human RECs without irradiation or KZ-41 treatment; IR group referring to human RECs treated with irradiation (30 Gy) for 24 hours; and IR+KZ-41 group referring to human RECs treated with both irradiation (30 Gy) for 24 hours and KZ-41, respectively.
Figure 6B:
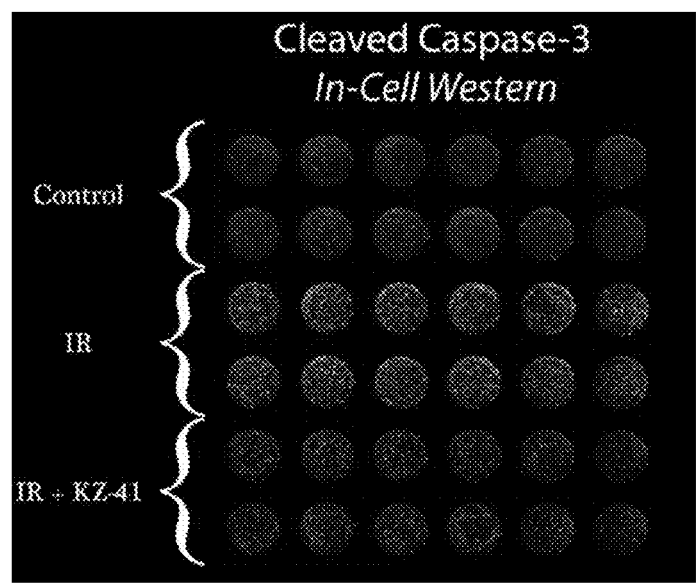
Figure 6C:
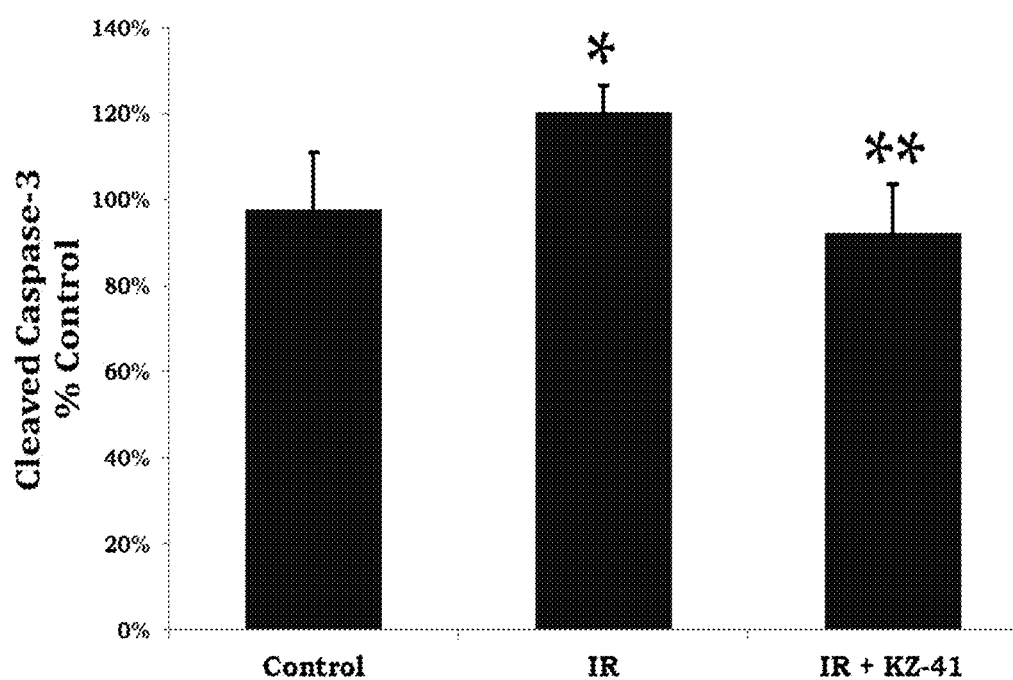

We further demonstrated that KZ-41 could prevent the irradiation-induced p38-p53-dependent apoptotic signaling pathway. We used two methods of analysis to detect the presence of cleaved caspase-3 in RECs following irradiation: sandwich ELISA (FIG. 6A) and In-Cell Western (ICW) (FIG. 6B). Results in both assays showed a significant increase in cleaved caspase-3 24 hours after radiation (*P<0.05 ELISA and ICW). With KZ-41 treatment, this level was significantly reduced (P<0.005, P<0.05; ELISA, ICW, respectively).

Figure 7A:
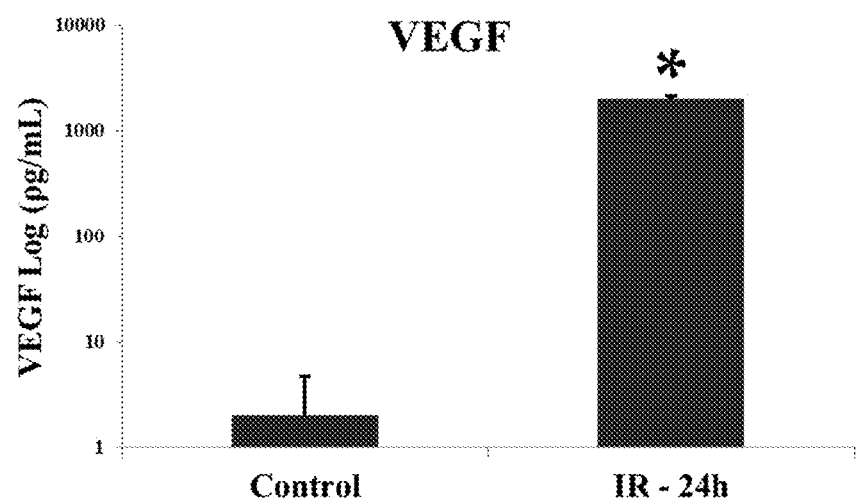
FIGS. 7A, 7B and 7C show graphs and images depicting the proliferative and migratory phenotype of human RECs in different treatment groups.
Figure 7B:
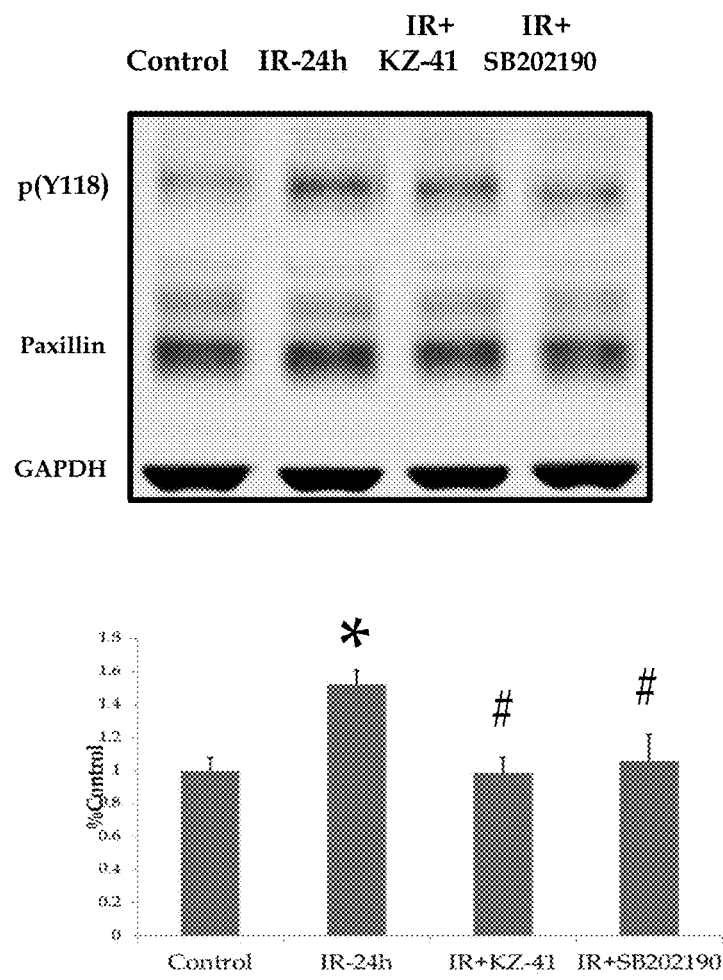
Figure 7C:
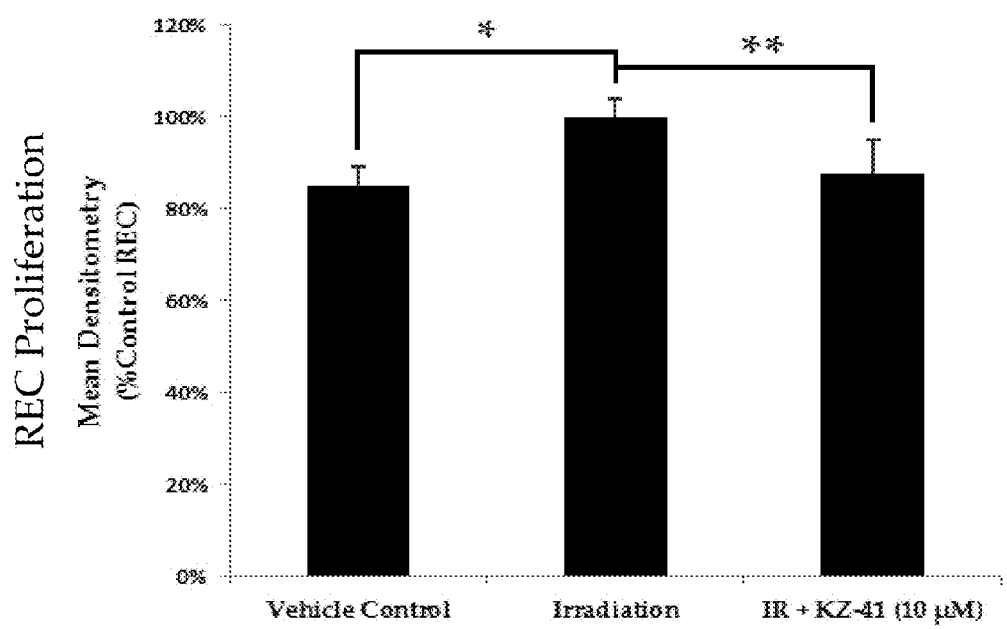

We further demonstrated that KZ-41 could reduce the irradiation-induced migratory potential of RECs by mitigating p38-dependent phosphorylation of focal adhesion scaffold protein paxillin. We examined if irradiated RECs showed enhanced VEGF secretion, promoting a pro-survival/pro-proliferative phenotype in the surviving fraction of cells. As a result shown in FIG. 7A, 24 hours post-irradiation, we detected significant increases in VEGF in culture media (*P<0.001). In addition, we examined the phosphorylation of paxillin in irradiated RECs and found a substantial increase of tyrosine phosphorylation of paxillin (Y118) 24 hours following irradiation (FIG. 7B; P<0.05). Further, we evaluated the effect of KZ-41 and SB202190 on paxillin phosphorylation in irradiated RECs and found that both KZ-41 and SB202190 significantly reduced phosphorylation of paxillin at Y118 (FIG. 7B; #P<0.05). Still further, we examined the effect of KZ-41 on the pathological REC pro-migratory/proliferative response that was triggered by radiation-induced VEGF expression and subsequent paxillin-phosphorylation and found that KZ-41 could significantly reduce the proliferative phenotype to almost normal levels in irradiated RECs (FIG. 7C, *P<0.05, **P<0.05).

Figure 8A:
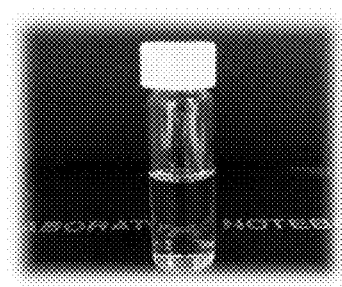
FIGS. 8A, 8B and 8C depict composition and characteristics of ocular nanoemulsion used for KZ-41 delivery.
Figure 8B:
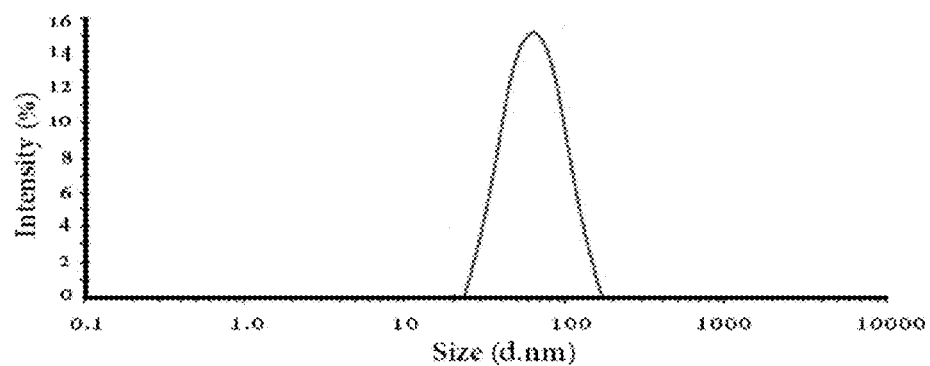
Figures 8C, 8D:
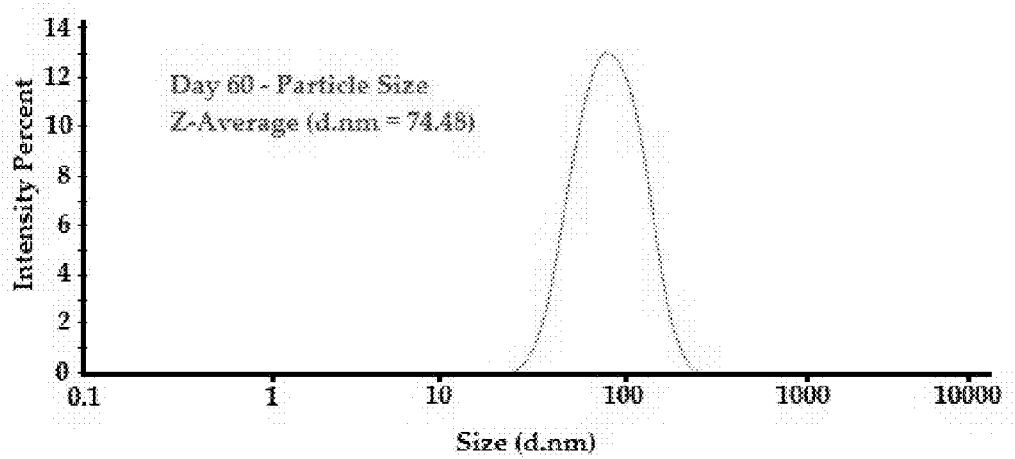
FIG. 8D shows a table depicting physicochemical properties of the nanoemulsion preparation: a viscosity of 17 mPa·s, average particle size of 60 nm at day zero, day 7 or after 3 cycles of freeze-thaw, and pH of 6.5.
Figure 9:
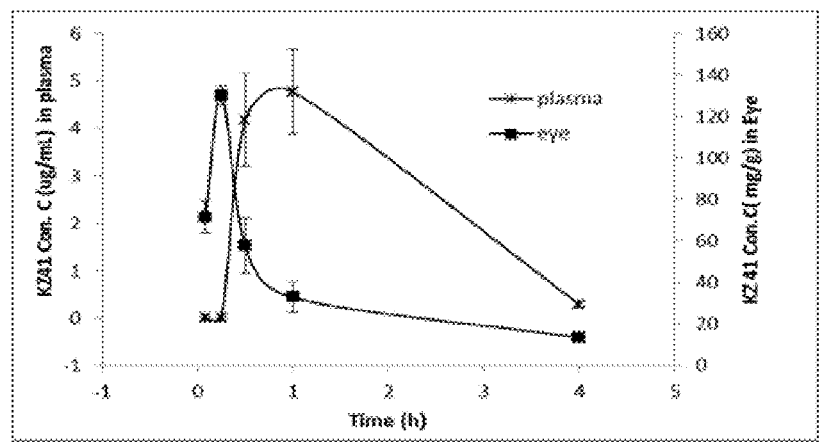
FIG. 9 shows graphs and tables depicting results of ocular pharmacokinetic analysis after 100 mg/kg KZ-41 was administered by the ophthalmic nanoemulsion method in mice.
Figure 10A:
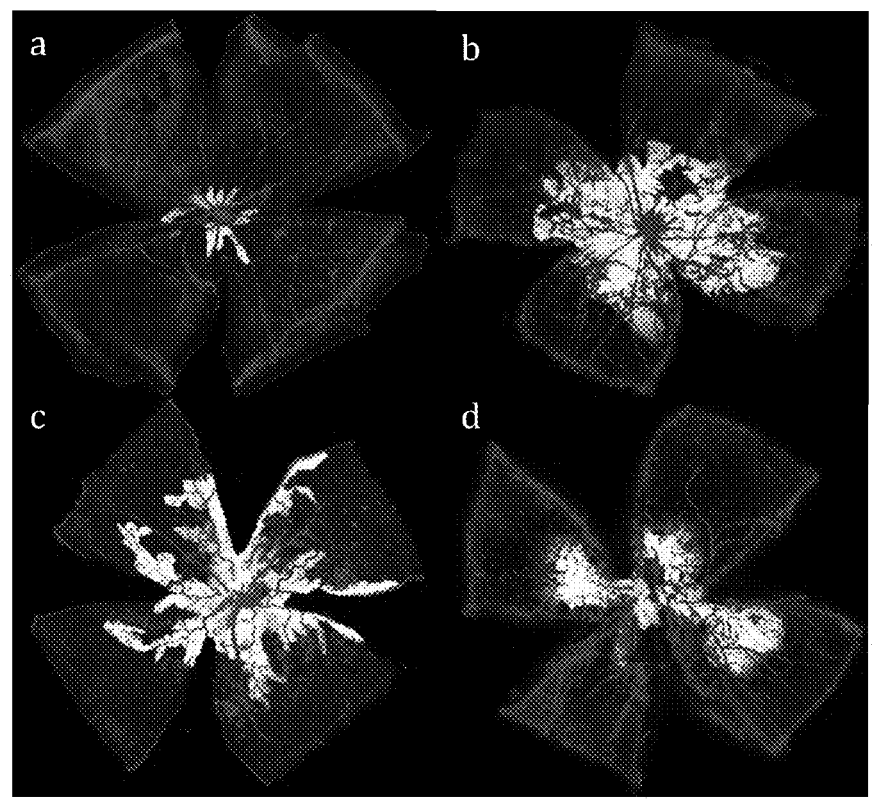
FIGS. 10A and 10B show images and graphs depicting vascularization in four different treatment groups (A, B, C and D): normoxia referring to mice without treatments; OIR referring to mice treated with ocular irradiation; OIR+V referring to mice treated with ocular irradiation and vehicle ocular nanoemulsion without KZ-41; and OIR+KZ-41 referring to mice treated with ocular irradiation and ocular nanoemulsion with KZ-41, respectively.
Figure 10A:
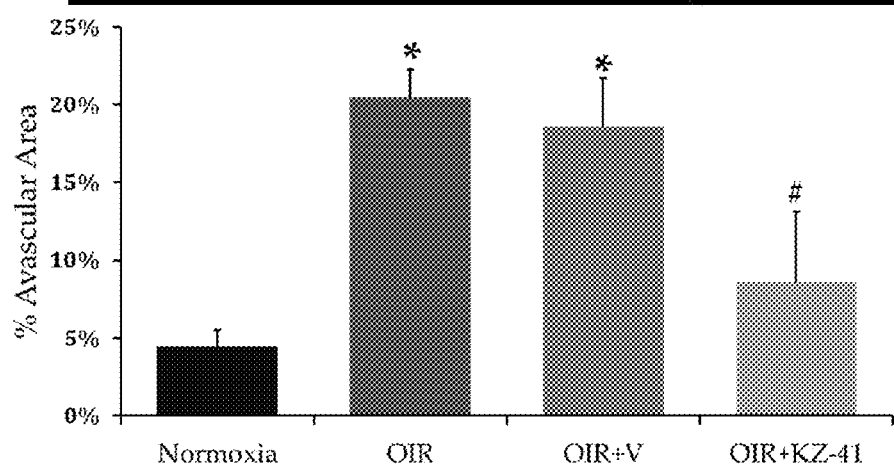
Figure 10B:
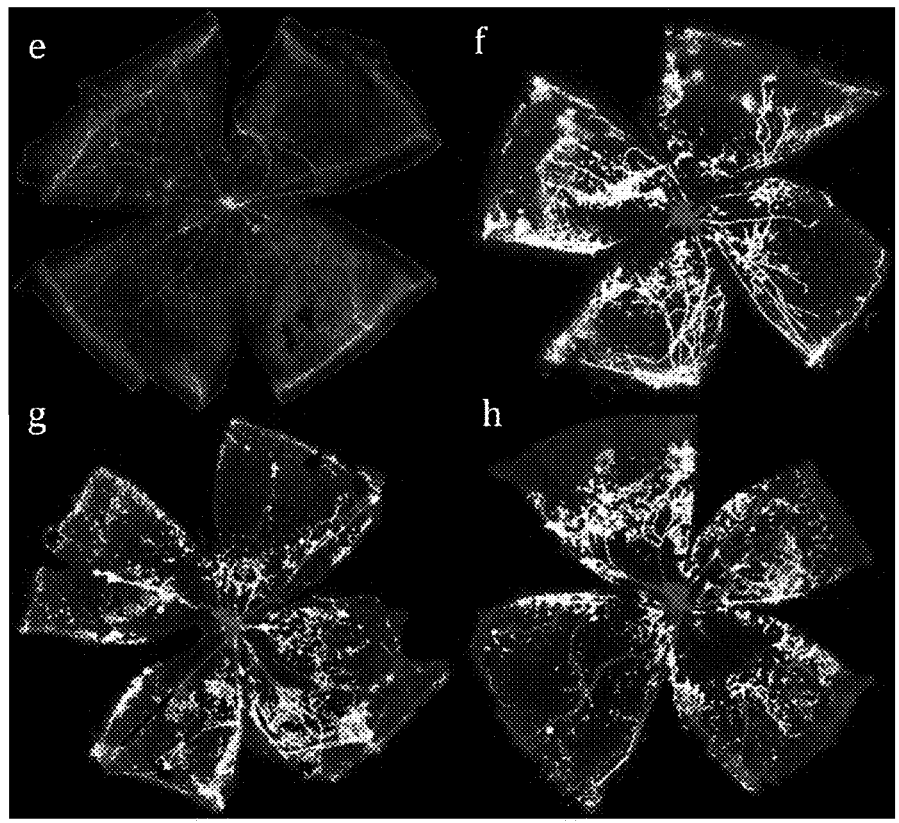
Figure 10B:
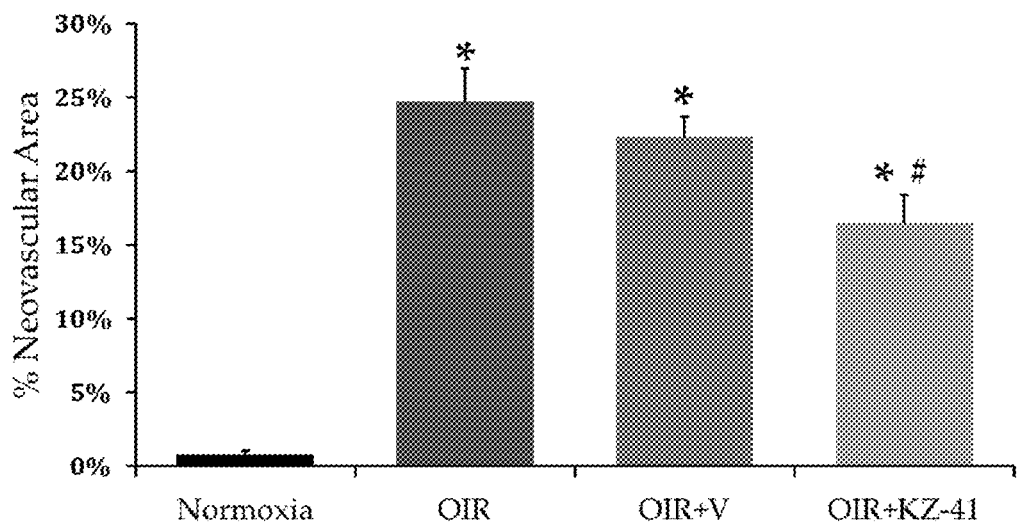

We herein further demonstrated that KZ-41 could pathological neovascularization and avascular areas in an oxygen-induced retinopathy mouse model. KZ-41 was delivered to mouse retinal cells through a drug-delivery system that we formulated so that the drug could be applied topically as an eye-drop. To confirm that efficacy of this method for delivering effective treatments to the back of eye, we performed a pilot ocular-PK study using C57BL/6J adult male mice (n=3 mice/time-point; FIG. 9). As shown in FIG. 8, nanoemulsion had a viscosity of 17 mPa·s, average particle size of 60 nm which would increase to 75 nm after being placed at room temperature for 60 days, and pH of 6.5. As shown in FIG. 9, ocular pharmacokinetic analysis confirmed that KZ-41 penetrated through the cornea tissue within 5 minutes and produced a mean peak vitreous humor concentration of 130.1±4.6 mg/mL at 15 minutes. KZ-41 concentration in the vitreous humor dropped exponentially with a half-life of 2.2±0.4 h. The volume of distribution was 1.8±0.4 L/kg, clearance was 0.57±0.07 L/h/kg (FIG. 9). Systemic circulation was achieved 30 minutes after ocular administration, correlating precisely with the apparent distribution of KZ-41 out of the eye.

The murine oxygen-induced retinopathy (OIR) model is the well-known and industry-recognized in vivo model for studying the effect of genomic or pharmacologic manipulation of key signaling proteins on the natural history of VEGF-induced proliferative retinopathies (e.g., RR, retinopathy of prematurity, and proliferative diabetic retinopathy) (Connor et al., 2009; Smith et al., 1994). We used this model to evaluate the effects of KZ-41 on preventing VEGF-induced pathological retinal neovascularization (RNV) driven by oxidative stress and ischemic injury. Specifically, mouse pups were exposed to 75% oxygen at post-natal day 7 (P7) for 5 days and then returned to normal oxygen at P12. Mice received daily ocular administration of either KZ-41 (100 mg/kg) or vehicle (ophthalmic NE) from P12 to P17 using the above delivery method. Eyes were enucleated at P17 and retinal whole-mounts stained for endothelial cells. Avascular area and vascular tufts were quantified as a percentage of total retinal vasculature using confocal microscopy (Connor et al., 2009).

As shown in FIGS. 10A, 10B, 10C, and 10D, we examined the flat-mounted retinas at P17 for each experimental group (A-D; Normoxia-N17, OIR17-untreated, OIR17+Vehicle, and OIR17+KZ-41.) Both OIR17 and OIR17+V mice showed larger avascular area (AV area) surrounding the optic disc as compared to N17 control mice (FIG. 10A, 20.5±1.8, 18.6±3.1 vs. 4.4±1.1 AV area, P<0.005) and extensive neovascularization area (NV area) compared to normoxia controls (FIG. 10B, 24.7±2.3, 22.3±1.4 vs. 0.76±0.28 percent NV area, P<0.005). There was no significant difference in total AV or NV area between OIR17 and OIR17+V mice (FIGS. 10A and 10B; P>0.05). OIR17+KZ-41 mice showed extensive physiological revascularization towards the optic disc with significant decreases in neovascular tuft formation as well as a two-fold reduction in avascular area as compared to OIR+V mice (OIR+KZ-41 vs. OIR+V 8.6 vs. 18.6 AV % area, 16.5 vs. 22.3 NV % area; #P<0.001, P<0.01 respectively).

While OIR+KZ-41 mice still showed significant increases in NV area compared to normoxia controls, AV area quantification was statistically indistinguishable from normoxia mice (P>0.05). We show that DNA damaging radiation triggers the accumulation of phosphorylated p38 and p53 to promote transcription and expression of inflammatory genes and proteins. Our quinic-acid derivative, KZ-41 has shown to inhibit p38-p53 signaling mechanisms to attenuate the expression of ICAM-1 and reduce apoptotic signaling in IR-RECs.

Therefore, in this Example 1, we demonstrated that KZ-41 could help preserve the integrity and functionality of the RECs, and prevent or decrease the risk of monocyte adhesion, subsequent endothelial cell dysfunction, neovascularization, and/or blindness. These effects were seen in both in vitro and in vivo pre-clinical models radiation retinopathy.

Example 2

KZ-41 could Regulate Retinal Endothelial Cell Viability in Connection with Diabetic Retinopathy In this Example 2, we demonstrated that KZ-41 could protect hRECs from glucose-induced apoptosis. We showed that IGF-1R activity and the cascade PI3/Akt pathway were stimulated by KZ-41 in RECs. Therefore, KZ-41 could be a novel therapeutic agent for diabetic retinopathy.

The materials and methods used in this Example 2 are as follows.

Reagents.

KZ-41 was synthesized in Dr. Duane Miller's laboratory and verified to be >96% pure by nuclear magnetic resonance spectroscopy (Zeng et al., 2009). Total IGF-R1, IRS-1, p-85, and Akt and phosphorylated (Tyr1135/1136) IGF-R1, (Ser473) Akt and (Tyr458) p85 primary, and GAPDH antibody (rabbit) primary antibodies were obtained from Cell Signaling (Danvers, Mass.). Secondary goat anti-rabbit IgG antibodies (IRDye 800CW) were purchased from LI-COR Biotechnology (Lincoln, Nebr.). The Class IA PI3 kinase inhibitor, LY294002, was kindly provided by Dr. Ramesh Ray (UT). D-Mannitol and Glucose were perched from Sigma.

Cell Culture.

Primary human retinal microvascular endothelial cells (REC, Lot 181) were acquired from Cell Systems Corporation (CSC, Kirkland, Wash.). Cells were grown in M131 medium containing microvascular growth supplements (Invitrogen, Carlsbad, Calif.), 10 µg/mL gentamicin, and 0.25 µg/mL amphotericin B. Prior to each experiment, cells were transferred to high (25 mM) or normal (5 mM) glucose, or mannitol (25 mM) medium for three days. Only primary cells within passage six were used. Cells were quiesced by incubating in high or normal glucose medium without fetal bovine serum for 24 hours and used to perform the experiments unless otherwise indicated. To investigate cell-signaling through PI3 kinase, LY294002 was added to culture medium for 3 hr prior to treatment with or without KZ41 (10 µM) for 2 hr.

Caspase-3 Activity.

The Pathscan Cleaved Caspase-3 sandwich ELISA kit (Cell Signaling) was used to evaluate endogenous cleaved caspase-3 levels in RECs according to the manufacturer's instructions. Cleaved caspase 3 level in normal glucose (5 mM), high osmolar (25 mM mannitol) or high glucose (25 mm) was detected following treatment with or without KZ-41 (10 µM) for 2 h. For all ELISA analyses, equal protein amounts were loaded into each well, allowing for comparisons using optical density (O. D.)

Western Blotting Analysis.

Cellular proteins were analyzed by Western blot after SDS-PAGE using rabbit anti-human specific primary antibodies. Retinal endothelial cells were ringed with cold phosphate-buffered saline after 2 hr KZ-41 treatment. REC lysates were collected in modified RIPA lysis buffer (20 mM Tris, 2.5 mM EDTA, 1% Triton X-100, 1% deoxycholate, 0.1% SDS, 40 mM NaF, 10 mM Na4P2O7, and 1 mM PMSF) with protease/phosphatase inhibitor (1×) cocktail (Roche; Indianapolis, Ind.). Lysates were kept on ice for 30 minutes followed by centrifugation to remove insoluble materials (12,000 g at 4° C. for 30 minutes). Total protein was measured using BCA assay (Pierce, Rockford, Ill.). Protein samples (10~50 µg) mixed with 4×LDS loading buffer with 2.5% 2-mercaptoethanol (Sigma), heated to 70° C. for 10 minutes, and loaded on NuPAGE 4-12% Bis-Tris gel (Invitrogen, Carlsbad, Calif.). Immunoblotting was performed with nitrocellulose membranes (Bio-Rad) at 170-mA start and 110-mA end at 25 V for 2 h in NuPAGE transfer buffer (Invitrogen) containing 20% methanol. Membranes were blocked using Odyssey blocking buffer (LI-COR) for one hour at room temperature with gentle shaking Membranes were then incubated at 4° C. with specific primary antibodies (1:1000) overnight. Cellular protein was normalized using GAPDH [1:10,000] (Cell Signaling). The secondary antibody (IRDye 800CW goat anti-rabbit) [1:10,000] was incubated in the dark at room temperature for 45 minutes. Dual-channel infrared scan and quantitation of immunoblots were conducted using the Odyssey® Sa infrared imaging system with Image Studio (Ver. 3.1.4) (LI-COR, Lincoln, Nebr.).

Statistical Analysis.

All data in the different experimental groups are expressed as mean±S.D. and obtained from at least three independent experiments. Analysis of variance (ANOVA) was used to assess the statistical significance of the differences between groups, followed by Duncan's multiple-range test or Student's t-test, where appropriate. A P value of <0.05 was considered significant.

Figure 11:
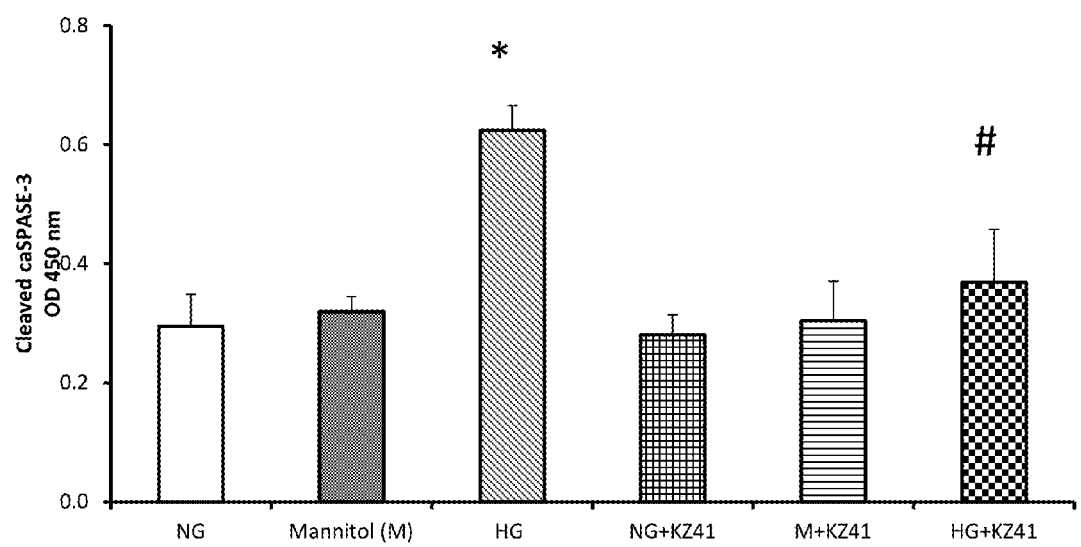
FIG. 11 shows a graph depicting the expression of cleaved caspase-3 in different group of human RECs: NG referring to RECs cultured in normal glucose levels at a concentration of 5 mM and treated with normal saline for two hours; Mannitol referring to RECs cultured 25 mM mannitol and treated with normal saline for two hours; HG referring to RECs cultured in high glucose levels at a concentration of 25 mM and treated with normal saline for two hours; NG+KZ41 referring to RECs cultured in normal glucose levels (5 mM) and treated with KZ-41 at 10 μM for two hours; M+KZ-41 referring to RECs cultured in mannitol (25 mM) and treated with KZ-41 at 10 μM for two hours; and HG+KZ41 referring to RECs cultured in high glucose levels (25 mM) and treated with KZ-41 at 10 μM for two hours. The amounts of cleaved capase-3 are represented in optical density (O.D. at 450 nm) with mean value±standard deviation. In each group, 6 independent assays were conducted. The symbol * means $P<0.05$ versus NG. The symbol # means $P<0.05$ versus HG (Student's t-test). Cleaved caspase-3 levels were measured by PathScan ELISA using an antibody specific for cleaved caspase-3 (Asp175) Rabbit mAb.

We herein demonstrated that KZ-41 could reduce glucose-induced apoptosis in RECs. Apoptotic cell death is triggered in RECs continuously exposed to high glucose concentrations (Costa et al., 2012; el-Remessy et al., 2005; Ho et al., 2000; Zhang et al., 2013). Activated (cleaved) caspase-3, a crucial effector of the terminal or execution phase of the apoptotic pathway, has been recognized as a reliable phenotypic marker of apoptosis (Zhang et al., 2005). Here, we evaluated the effect of KZ-41 (10 µM) on caspase-3 activation in RECs cultured in either normal glucose (5 mM), high glucose (25 mM), or mannitol (25 mM) for three days. As shown in FIG. 11, caspase-3 levels in RECs exposed to high glucose were significantly higher when compared to RECs cultured in normal glucose (0.62±0.04 vs. 0.29±0.05; P<0.01). RECs cultured in mannitol (25 mM), as an osmotic control, showed no increase in cleaved caspase-3 activity when compared to RECs cultured in normal glucose (0.32±0.03 vs. 0.29±0.05; P>0.05). KZ-41 significantly reduced cleaved caspase-3 levels RECs exposed to high glucose (0.37±0.09 vs. 0.62±0.04; P<0.01). Cleaved caspase-3 levels were unaltered by KZ-41 in RECs cultured in either normal glucose or mannitol. Together, these results indicated that KZ-41 reversed glucose-induced caspase-3 activation without affecting constitutive caspase-3 levels in RECs.

Figure 12A:
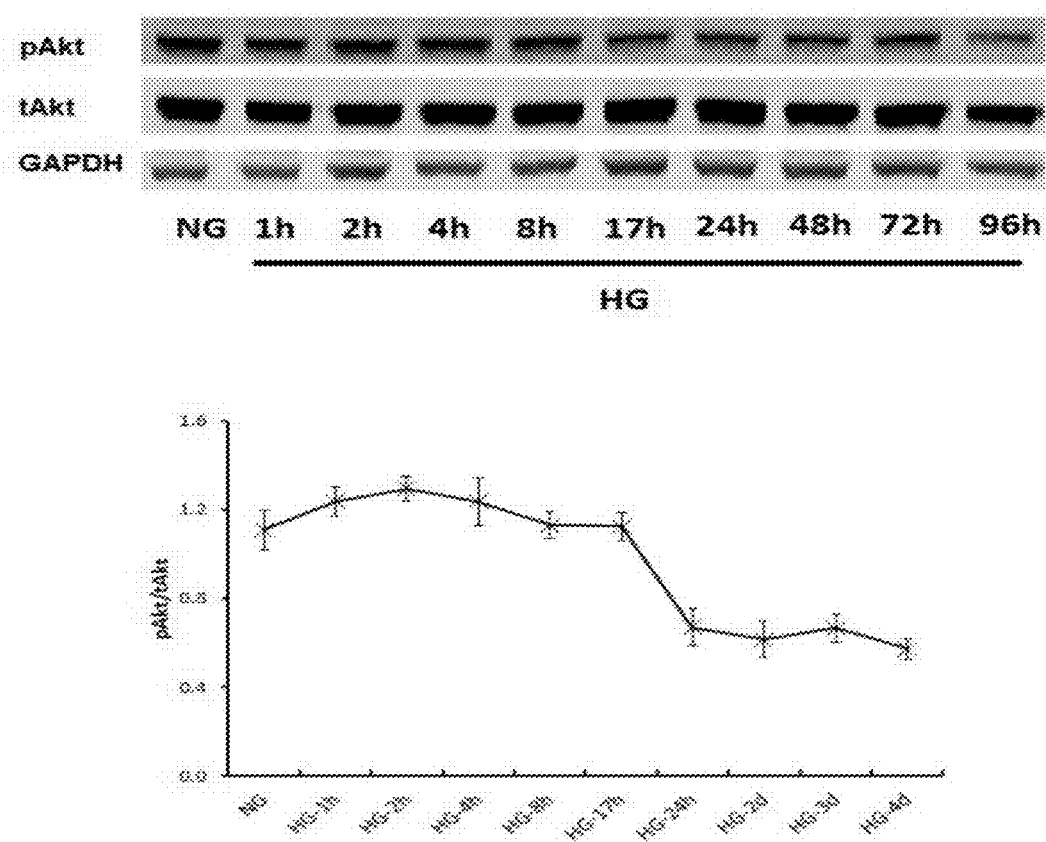
FIGS. 12A and 12B show images and graphs depicting the expression of phosphorylated Akt protein in different treatment groups.

We further demonstrated that Akt activity could be increased by KZ-41. Prolonged high glucose exposure inactivates the PI3-kinase/AKT pro-survival signaling pathway leading to reduced REC cell viability within three days (Costa et al., 2012; Jiang et al., 2012; Zhang et al., 2013). In this series of experiments, we evaluated total and phosphorylated (Ser473) Akt levels, as a readout of pro-survival signaling, over four days in RECs exposed to high glucose (25 mM). Phosphorylated Akt levels modestly increased over the first 18 hours after glucose exposure, but were significantly attenuated at 24-96 hours (FIG. 12A). Total Akt levels were unchanged over the four day period of high glucose exposure. Consequently, the ratio of phosphorylated Akt to total Akt protein expression was significantly decreased between 24-96 hours.

Figure 12B:
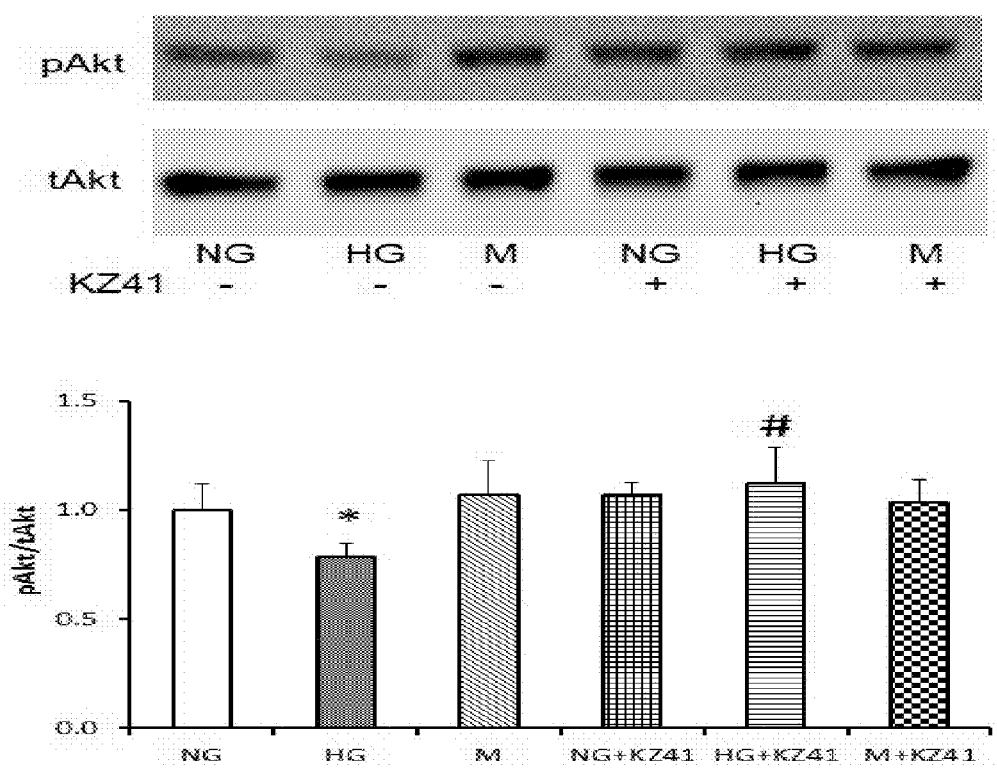

In addition, we measured the effect of KZ-41 on total and phosphorylated (Ser473) Akt expression in RECs cultured in high glucose for 72 hours (FIG. 12B). Following 2 hours incubation, KZ-41 (10 µM) reversed the effect of high glucose on phosphorylated Akt expression (1.13±0.16 vs. 0.79±0.06; P<0.05) without altering total Akt expression. The net effect of KZ-41 treatment was restoration of the ratio of phosphorylated to total Akt expression found in RECs cultured in normal glucose. The ratio of phosphorylated to total Akt expression was not significantly affected by KZ-41 in RECs cultured in either normal glucose or mannitol.

Figure 13A:
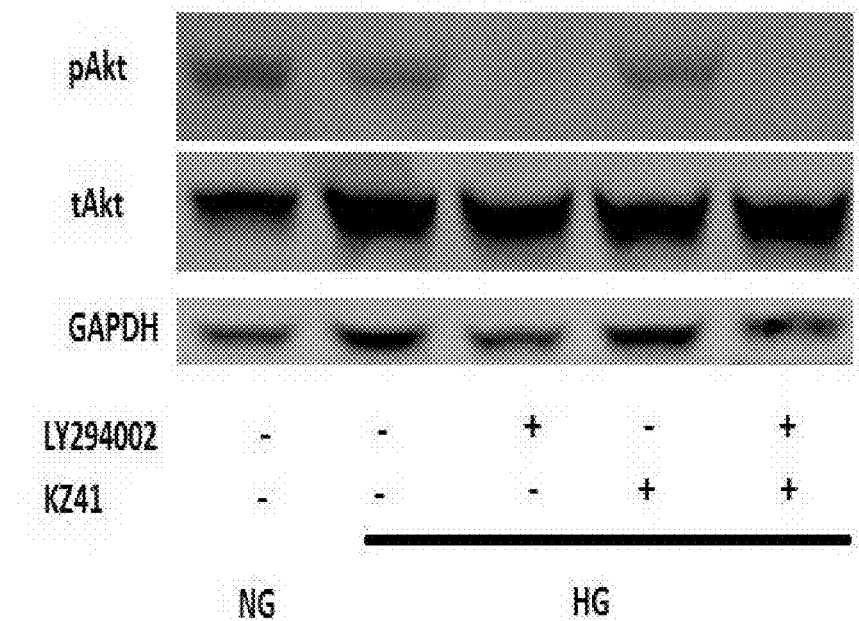
FIGS. 13A and 13B show Western Blotting images and graphs depicting the expression of phosphorylated Akt/total Akt and phosphorylated p85/total p85 in different treatment groups of RECs.
Figure 13B:
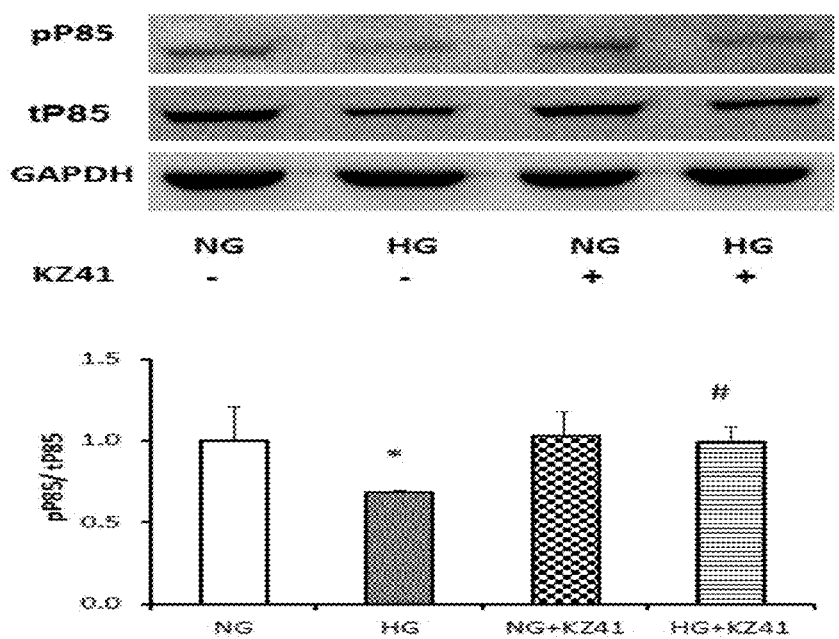

We further demonstrated that KZ-41 could enhance PI3K activity. Phosphatidylinositide 3-kinase (PI3K) promotes pro-survival signal transduction by phosphorylating Akt (Alessi et al., 1996). We used the PI3K inhibitor LY294002 to examine the requirement for PI3K in KZ-41's pro-survival signal transduction mechanism. Pretreatment of RECs with LY294002 resulted in a complete block of KZ-41-induced Akt phosphorylation suggesting KZ-41 signaling required PI3K (FIG. 13A). LY294002 inhibits class IA, class IB, and class III PI3Ks with equal potency (Vanhaesebroeck et al., 2001). PI3K class IA comprises an 85 kDa regulatory subunit (p85) and a 110 kDa catalytic subunit (p110) (Carpenter et al., 1990). High glucose suppresses p85 phosphorylation and PI3K activity in RECs (references). Thus, we next examined the effect of KZ-41 on glucose-induced alterations in p85 phosphorylation (Tyr458) (FIG. 13B). Following two hours incubation, KZ-41 (10 µM) reversed the effect of high glucose on phosphorylated p85 expression (0.995±0.086 vs. 0.687±0.008; P<0.01) without altering total p85 expression. The net effect of KZ-41 treatment was restoration of the ratio of phosphorylated to total p85 expression found in RECs cultured in normal glucose. These data suggest that KZ-41 exerted its pro-survival effects through PI3K class IA proteins.

Figure 14:
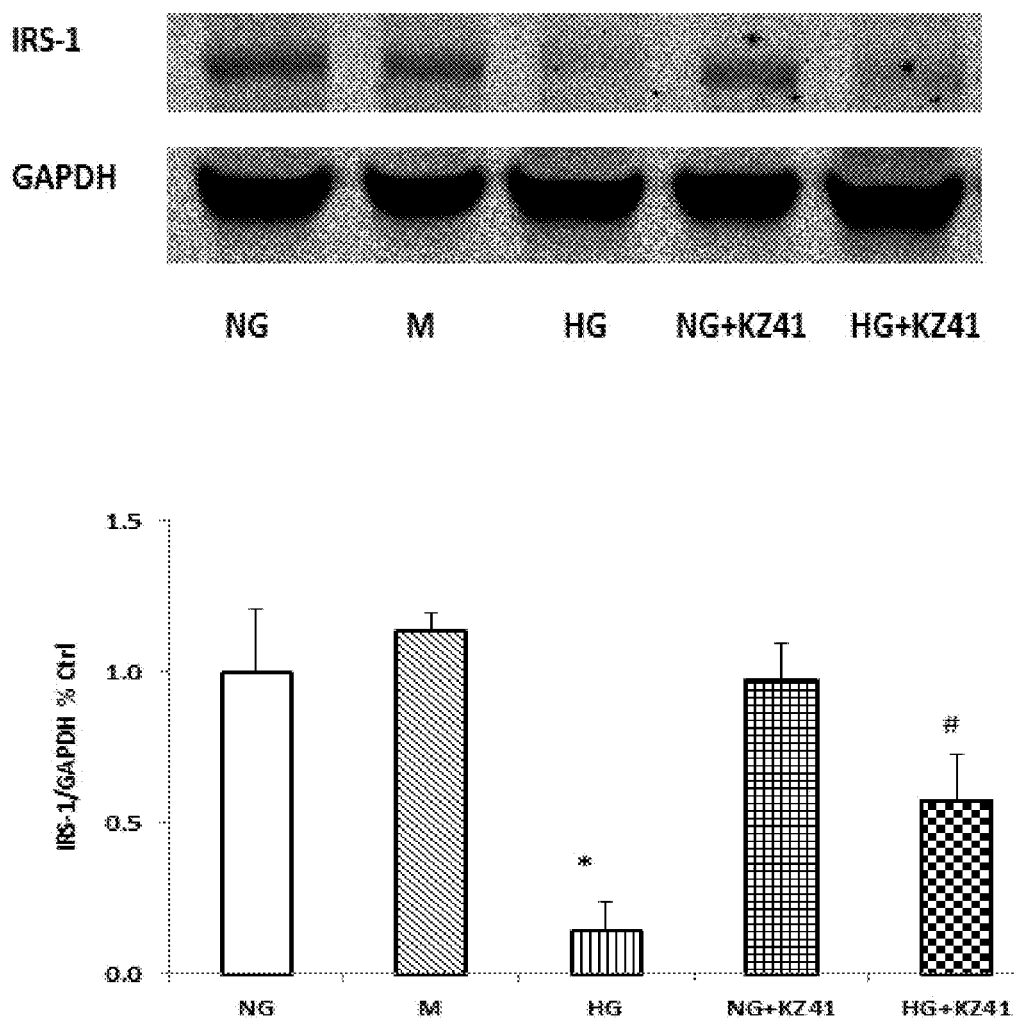
FIG. 14 shows a Western Blotting image depicting the expression of IRS-1 and GAPDH proteins in five groups of REC cells (upper panel) and a graph depicting the results in the Western Blotting image (lower panel). The five groups of RECs are RECs cultured in normal glucose (5 mM, NG), high glucose (25 mM, HG), Mannitol (25 mM, M), normal glucose with KZ-41 treatment (10 μM for 2 hr) and high glucose with KZ-41 treatment (10 μM for 2 hr). The symbol * means $P<0.05$ versus NG. The symbol # means $P<0.05$ versus HG. In each group, 3 cell cultures were performed and assayed. All data are represented as mean values±standard deviations.

We further demonstrated that KZ-41 could enhance IRS-1 expression. We measured IRS-1 expression in RECs cultured in high glucose for 72 hours (FIG. 14). High glucose dramatically decreased IRS-1 expression (0.14±0.1 vs. 1.00±0.21; P<0.01). However, KZ-41 was able to partially reverse the impact of high glucose on IRS-1 expression (0.58±0.15 vs. 0.14±0.1; P<0.05). These data suggest that the effect of KZ-41 is mediated, in part, through IRS-1.

Figure 15A:
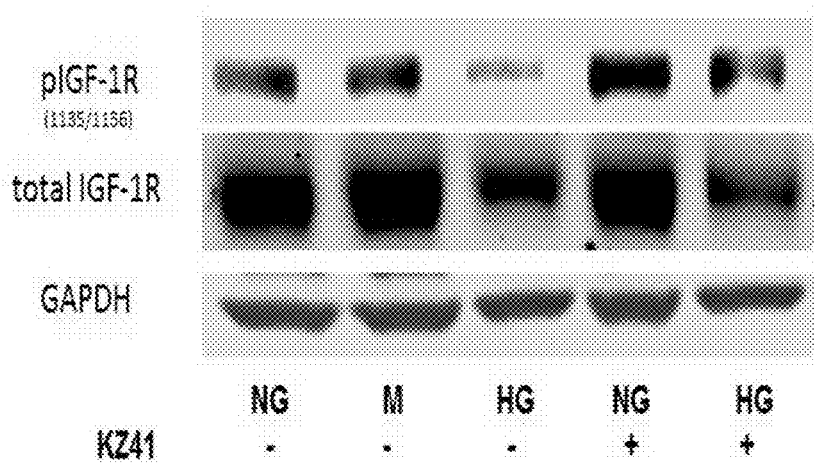
FIG. 15A shows a Western blotting image depicting the expression of phosphorylated IGF-1R$^{1135/1136}$, total IGF-1R, and GAPDH proteins in different REC groups. REC cells cultures in normal glucose (5 mM, NG), high glucose (25 mM, HG), Mannitol (25 mM, M), normal glucose with KZ-41 treatment (10 μM for 2 hr), and high glucose with KZ-41 treatment (10 μM for 2 hr).
Figure 15B:
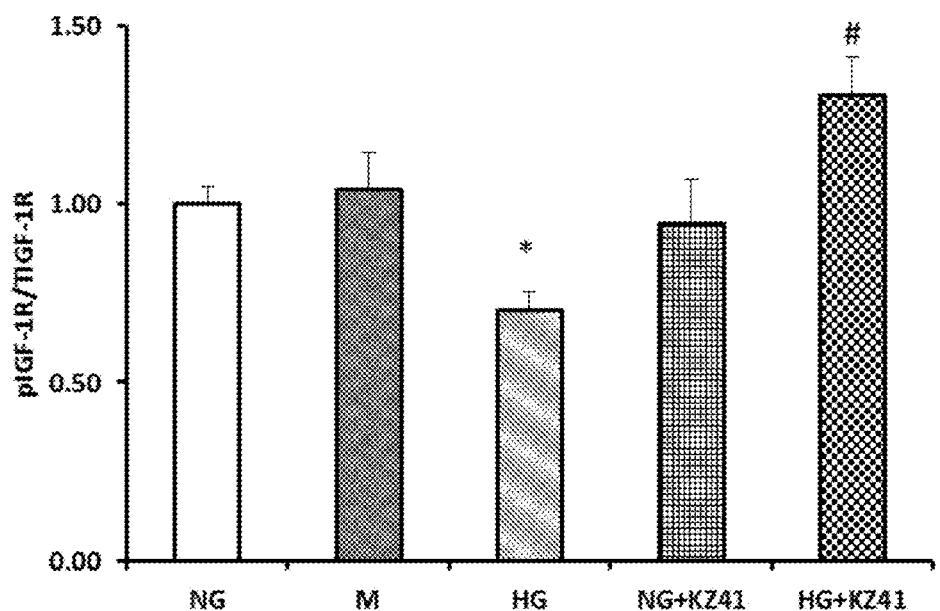
FIG. 15B shows a graph depicting the ratio of phosphorylated IGF-1R$^{1135/1136}$ to total IGF-1R in each of the five groups.
Figure 15C:
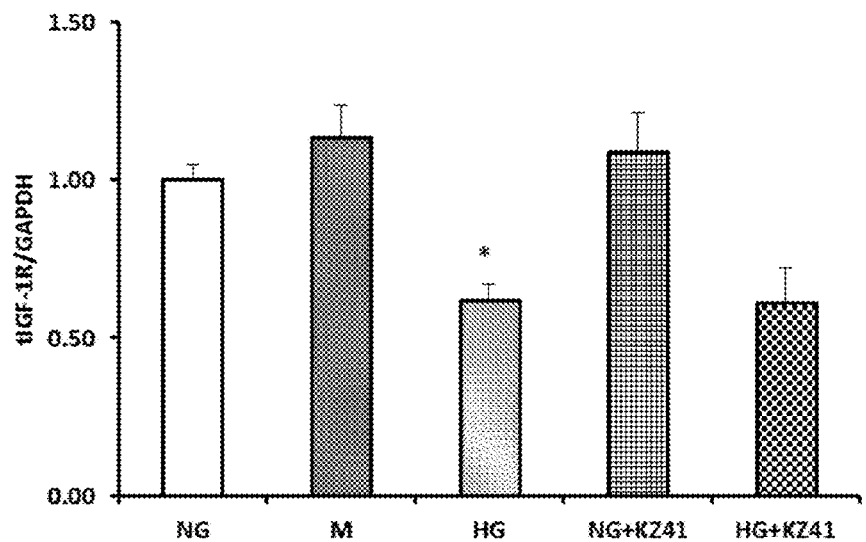
FIG. 15C shows a graph depicting the ratio of total IGF-1R to GAPDH in each of the five groups.
Figure 15D:
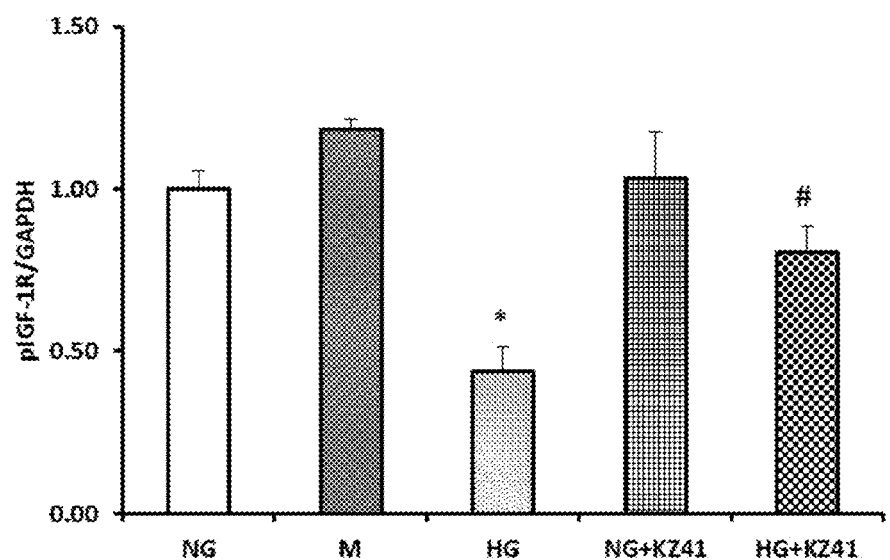
FIG. 15D shows a graph depicting the ratio of phosphorylated IGF-1R$^{1135/1136}$ to GAPDH in each of the five groups. The symbol * means P<0.05 versus NG. The symbol # means P<0.05 versus HG. In each group, 3 cell cultures were performed and assayed. All data are represented as mean values±standard deviations.

We further demonstrated that KZ-41 treatment could activate IGF-1R-mediated survival signaling pathways in response to HG in REC cells. KZ-41 could enhance IGF-R1 activation and lead to increased IRS-1/PI3K/Akt signaling. We measured the expression of phosphorylated IGF-R1, total IGF-R1, and GAPDH proteins in REC cells cultured in normal glucose, mannitol, and high glucose medium with or without KZ-41 treatment (FIG. 15A). High glucose inhibited phosphorylated (Tyr1135/1136) IGF-R1 (FIG. 15D) and total IGF-R1 expression (FIG. 15C) as well as the ratio of phosphorylated (Tyr1135/1136) to total IGF-R1 (FIG. 15B). Whereas, the ratio of phosphorylated (Tyr1135/1136) to total IGF-R1 in KZ-41-treated (10 µM, two hours) RECs was higher than that found in RECs cultured in normal glucose (1.31±0.10 vs. 1.00±0.05; P<0.05) or high glucose alone (1.31±0.10 vs. 0.70±0.05; P<0.01) (FIG. 15B). Altogether, these data showed that KZ-41 could induce IGF-1R-mediated pro-survival signaling in RECs cultured in conditions designed to mimic the diabetic milieu.

In summary, in the Example 2, we showed that KZ-41 could be a protective agent against high-glucose induced apoptosis in REC cells. We observed that high glucose induced REC cells apoptosis. Apoptosis is defined as the process of cell death associated with caspase activation or caspase-mediated cell death. It is a necessary component of development and characteristic of all self-renewing tissues. Here, we demonstrated that treatment with KZ-41 inhibited high glucose induced apoptosis of REC cells, indicating an anti-apoptotic role for KZ-41 in REC cells. Therefore, KZ-41 could be used as a novel therapeutic candidate for diabetic retinopathy.

Example 3

KZ-41 could Regulate Retinal Endothelial Cell Viability in Connection with Chemotherapy for Retinoblastoma We previously found that exposure to a retinoblastoma cell cidal melphalan dose (4 µg/mL) (Steinle et al., 2012) produced a greater than 6-fold increase in REC death. In this Example 3, we further demonstrated that KZ-41 could inhibit REC apoptosis by regulating the NF-κB pathway.

The materials and methods used in this Example 3 are as follows.

Reagents.

Melphalan was bought from Bioniche Pharma (Lake Forest, Ill.). KZ-41 was supplied by Dr. C. Ryan Yates. ICAM-1 ELISA kit was purchased from Millipore (Bilerica, Mass.). Cell death ELISA kit was purchased from Roche Applied Science (Indianapolis, Ind.). NF-κB, phospho-NF-κB (S536), p38 MAPK, phospho-p38 MAPK (T180/Y182) antibodies and SB202190 (p38 MAPK inhibitor, blocks P38α and P38β) were purchased from Cell Signaling (Lake Placid, N.Y.). Actin antibodies were purchased from Santa Cruz Biotechnology (Santa Cruz, Calif.). Lipofectamine™ RNAiMAX Transfection Reagent was purchased from Invitrogen (Carlsbad, Calif.). Human Sc siRNA (ON-TARGET plus nontargeting Pool D-001810-10), human ICAM-1 siRNA (ON-TARGET plus SMARTpool L-003502-00-0005), human TNF-α siRNA (ON-TARGET plus SMARTpool L-010546-00-0005), and human NF-κB siRNA (ON-TARGET plus SMARTpool L-003520-00-0005) were purchased from Dharmacon RNAi Technologies (Chicago, Ill.). Etanercept was obtained from Dr. Arnold Postlewaite. Secondary anti-mouse and anti-rabbit antibodies conjugated with horseradish peroxidase were purchased from Promega (Madison, Wis.). ECL for immunoblot development and signal detection was purchased from Amersham Biosciences (Piscataway, N.J., USA).

Cell Culture.

REC were provided by Cell System Corporation (CSC, Kirkland, Wash.) and grown in Medium 131 containing microvascular growth supplements (MVGS), 10 µg/mL gentamycin, and 0.25 µg/mL amphotericin B. Cultures were maintained at 37° C. in a humidified 95% air and 5% $CO_2$ atmosphere. Only primary cells within passages 6 were used. RECs were growth-arrested by incubating in Medium 131 for 24 hours and used to perform the experiments unless otherwise indicated. Y79 retinoblastoma cells were purchased from ATCC. Cells were grown in suspension in RPMI medium with antibiotics and 20% fetal bovine serum. Cells were starved overnight before any treatments.

Cell Death Assay.

Equal number of RECs were placed into the 96-well plates and cultured to 90% confluence. Cells were starved without growth factor overnight and treated with the drug for 24 hours. Cells were washed with PBS twice and resuspended in 200 µL lysis buffer, incubated for 30 minutes at room temperature. Lysates were centrifuged at 200×g for 10 minutes, and 20 µL of cell lysates were transferred into the streptavidin-coated MP under gentle shaking for 2 hours at 20° C. Supernatants were removed and the wells were washed with incubation buffer. ABTS solution was added to develop color detected at 405 nm (vs. 490 nm reference).

ICAM-1 ELISA.

An ELISA for ICAM-1 level was performed using an ICAM-1 ELISA assay kit according to the manufacturer's instructions to evaluate the ICAM-1 level following treatment with melphalan and KZ-41, ICAM-1 siRNA, TNF-α siRNA, NF-κB siRNA, or Enbrel (10 uM). For all ELISA analyses, equal protein amounts were loaded into each well, allowing for comparisons using optical density (O. D.).

Western Blotting.

After appropriate treatments and rinsing with cold phosphate-buffered saline, REC were lysed in the lysis buffer containing the protease and phosphatase inhibitors and scraped into the tubes. Equal amounts of protein from the cell or tissue extracts were separated on the pre-cast trisglycine gel (Invitrogen, Carlsbad, Calif.), blotted onto a nitrocellulose membrane. After blocking in TBST (10 mM Tris-HCl buffer, pH 8.0, 150 mM NaCl, 0.1% Tween 20) and 5% (w/v) BSA, the membrane was treated with NF-κB, Phospho-NF-κB, p38$^{MAPK}$, Phospho-p38$^{MAPK}$ antibodies (1:500) followed by incubation with horseradish peroxidase labeled secondary antibodies. The antigen-antibody complexes were detected using chemilluminescence reagent kit (Thermo Scientific).

Transfections.

REC were transfected with ICAM-1 siRNA, TNF-α siRNA, or NF-κB siRNA at a final concentration of 20 nM using Lipofectamine™ RNAiMAX Transfection Reagent according to the manufacturer's instructions. After transfection, cells were starved in MVGS-free Medium 131 for 24 hours and used as required.

Statistics.

All the experiments were repeated in triplicate, and the data are presented as mean±SEM. Data was analyzed by Kruskal-Wallis non-parametric test followed by Dunn's test with p-values <0.05 considered statistically significant. In the case of Western blotting, one representative blot is shown.

Figure 16A:
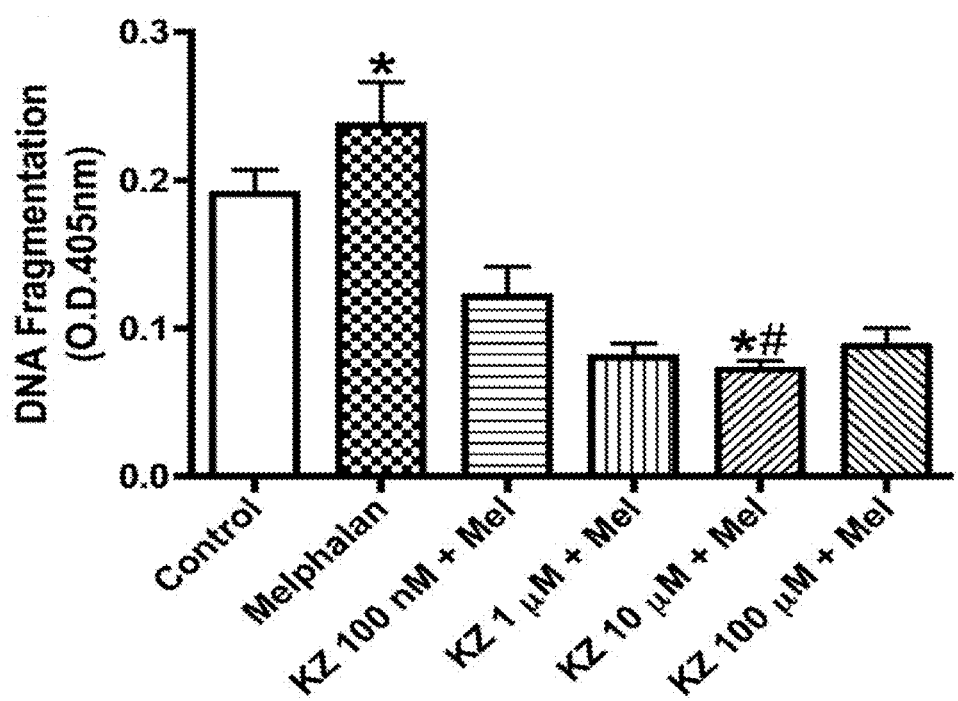
FIG. 16A shows a graph depicting cell death ELISA (Roche) results of RECs treated with nothing (control), melphalan (4 μg/mL) and melphalan+various doses of KZ-41. The symbol * means P<0.05 vs. control. The symbol # means P<0.05 vs. melphalan only. In each group, 4 cell cultures were performed and assayed.

We demonstrated that KZ-41 could inhibit melphalan-induced REC apoptosis. We have previously found that 4 μg/ml melphalan increases REC cell death (Steinle et al., 2012). We herein verified that 4 μg/mL did increase DNA fragmentation (FIG. 16A). To our surprise, KZ-41 treatment could counter the pro-apoptotic effects of melphalan. As shown in FIG. 16A, the effect of KZ-41 on inhibiting melphalan-induced REC apoptosis was dose-dependent. A significant decrease of apoptosis in comparison to that in RECs treated with melphalan alone was seen when KZ-41 was used to treat RECs at a concentration of 10 μM (see the bar over the group "KZ 10 μM+Mel" and the bar over the group "Melphalan" in FIG. 16A).

Figure 16B:
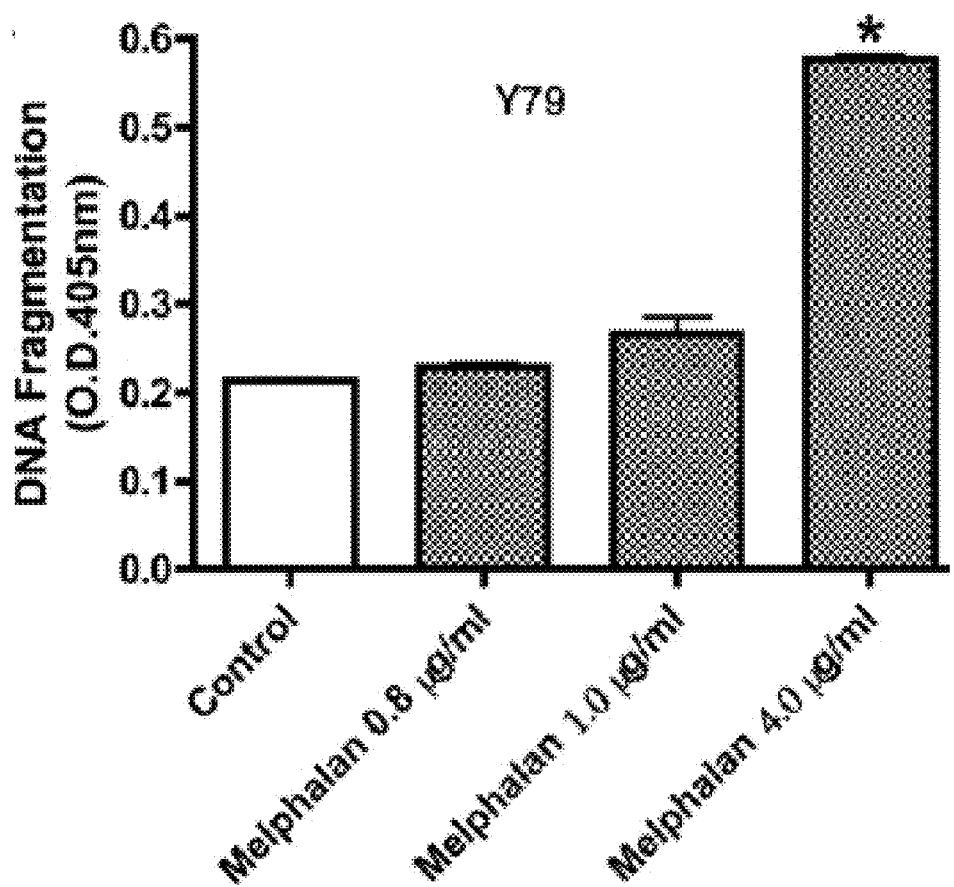
FIG. 16B shows a graph depicting cell death ELISA (Roche) result of Y79 retinoblastoma cells with no treatment (control), 0.8 μg/mL, 1 μg/mL or 4 μg/mL melphalan to demonstrate that melphalan best induces apoptosis at 4 μg/mL.
Figure 16C:
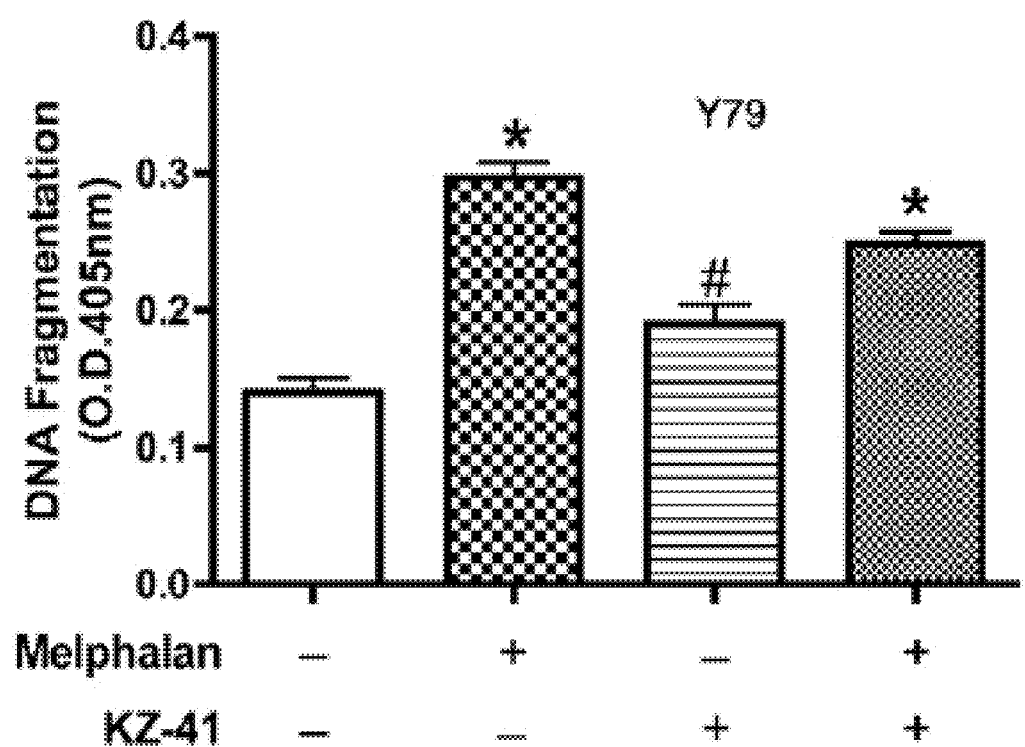
FIG. 16C shows a graph depicting cell death ELISA (Roche) results of Y79 retinoblastoma cells treated with melphalan at 4 μg/mL alone or in combination with KZ-41. KZ-41 did not inhibit melphalan-induced apoptosis of Y79 cells. The symbol * means P<0.05 vs. control. The symbol # means P<0.05 vs. melphalan only. In each group, 4 cell cultures were performed and assayed. All data are represented as mean values±standard error of the mean.

We further demonstrated that KZ-41 did not affect apoptosis of Y79 retinoblastoma cells. While KZ-41 could inhibit melphalan-induced REC apoptosis, KZ-41 did not inhibit the death of retinoblastoma cells. We tested various doses of melphalan on Y79 retinoblastoma cells and found 4 μg/mL produced maximal apoptosis (FIG. 16B). KZ-41 did not affect apoptosis of the Y79 cells because there was no significant difference of apoptosis of Y79 cells between the group treated with melphalan alone and the group treated with both melphalan and KZ-41 (FIG. 16C) (P>0.05).

Figure 17A:
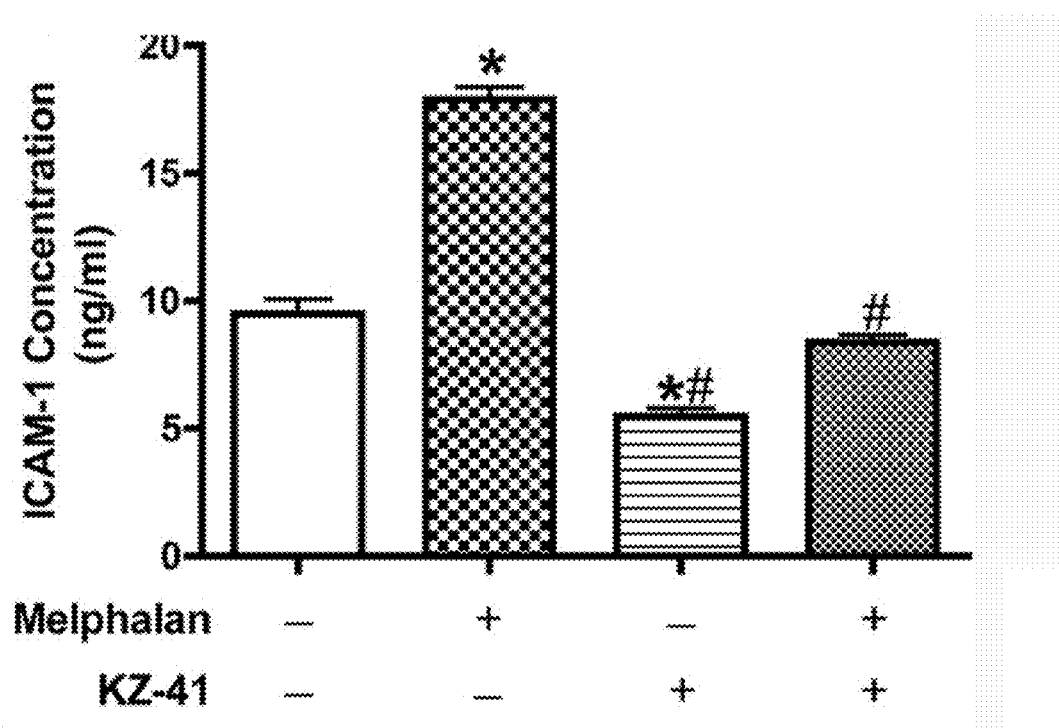
FIG. 17A shows a graph depicting the ICAM-1 ELISA results for RECs treated with nothing, melphalan only, or melphalan+KZ-41 (10 uM). The y-axis shows ICAM-1 concentration in ng/mL.
Figure 17B:
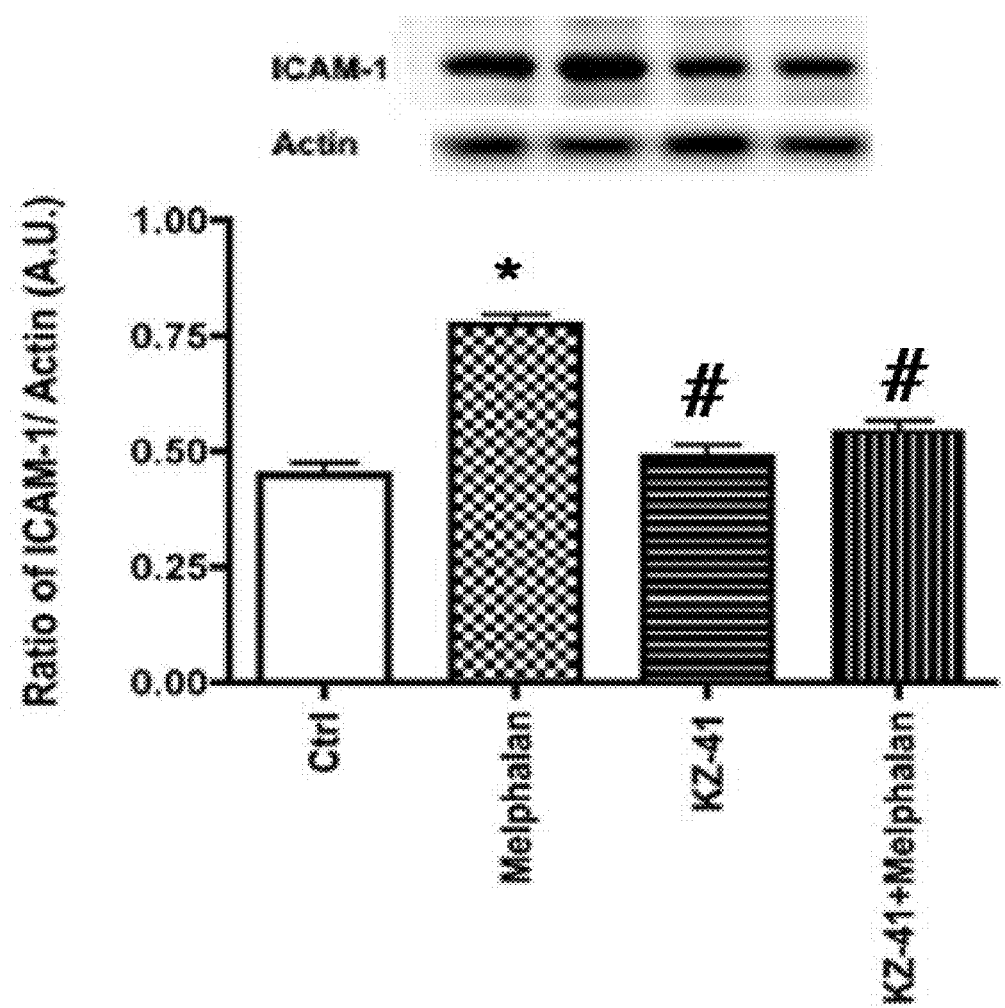
FIG. 17B shows a graph depicting the ICAM-1 Western blot results of RECs untreated, melphalan only, KZ-41 or Melphalan+KZ-41. The y-axis shows the intensity ratio of ICAM-1 to Actin. In both ELISA and Western blot results, KZ-41 reduced melphalan-induced ICAM-1 levels in RECs. The symbol * means P<0.05 vs. control. The symbol # means P<0.05 vs. melphalan only. In each group, 4 cell cultures were performed and assayed. All data are represented as mean values±standard error of the mean.

We further demonstrated that KZ-41 could inhibit melphalan-induced ICAM-1 expression levels in RECs. We have previously reported that melphalan increases ICAM-1 mRNA and protein levels (Steinle et al., 2012). We performed an ICAM-1 ELISA after KZ-41+melphalan treatment in RECs. As shown in FIGS. 17A and 17B, when 10 μM KZ-41 was added 30 minutes before melphalan treatment, we saw significantly decreased ICAM-1 levels in RECs. Therefore, KZ-41 could block melphalan-induced ICAM-1 levels in RECs.

Figure 18A:
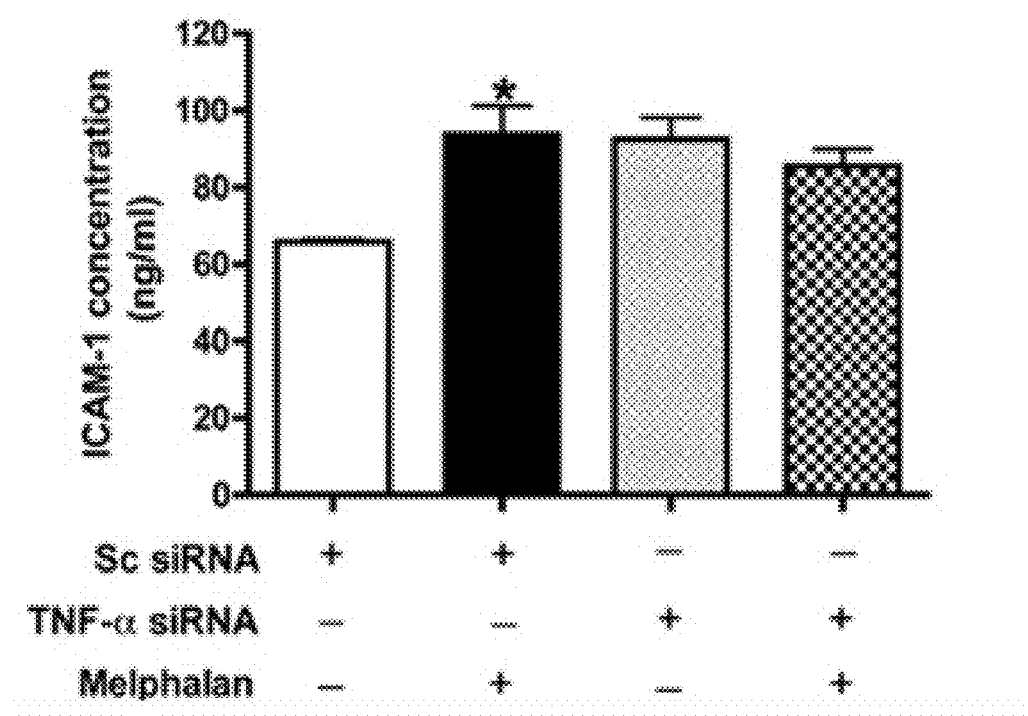
FIGS. 18A and 18B show graphs depicting the ICAM-1 ELISA results of RECs treated with (from left to right) sc siRNA, TNFα siRNA (FIG. 18A) or etanercept (FIG. 18B) and melphalan. Neither TNFα siRNA nor etanercept reduced ICAM-1 levels after melphalan treatment. The y-axis shows ICAM-1 concentration in ng/mL.
Figure 18B:
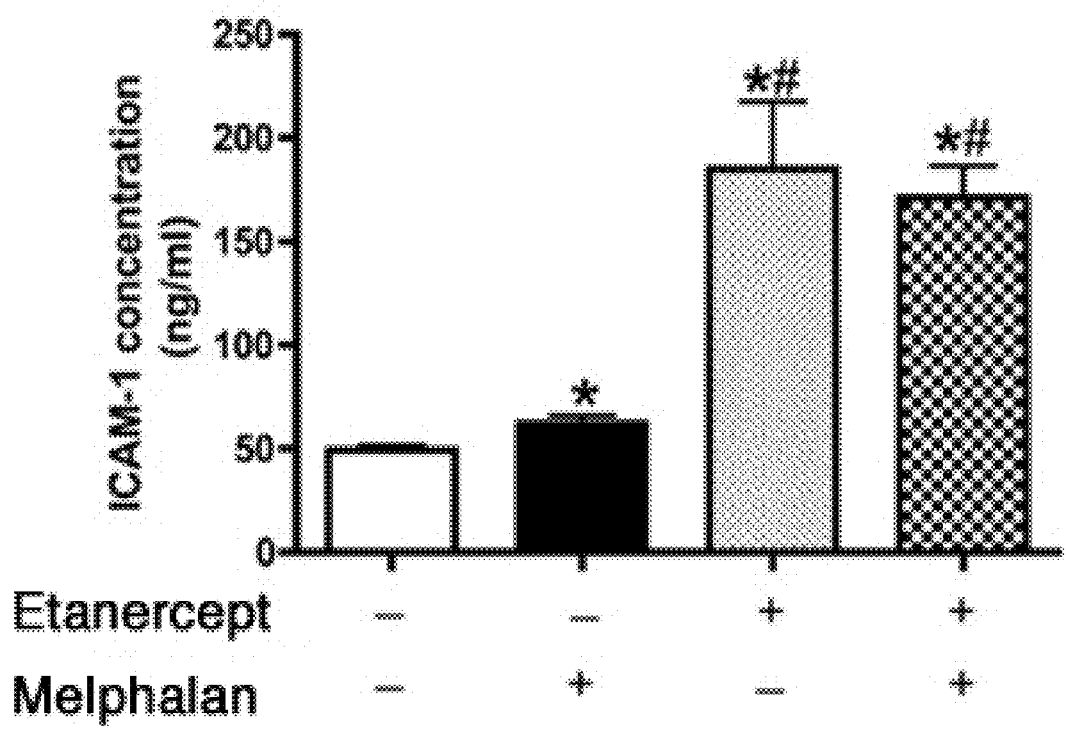
Figure 18C:
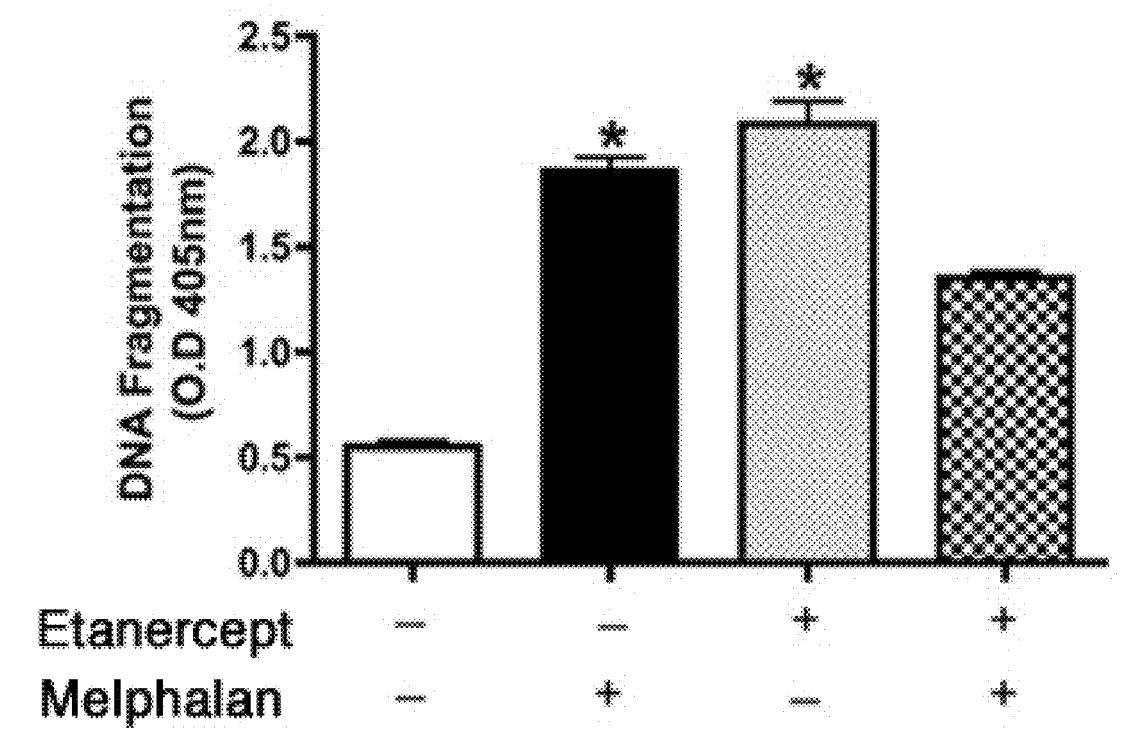
FIG. 18C shows a graph depicting cell death ELISA (Roche) results of RECs treated with etanercept and/or melphalan. The y-axis shows DNA fragmentation in O.D. 405 nm. While etanercept did reduce melphalan-induced REC apoptosis, it did not reach statistical significance. The symbol * means P<0.05 vs. control. The symbol # means P<0.05 vs. melphalan only. In each group, 4 cell cultures were performed and assayed. All data are represented as mean values±standard error of the mean.

We further demonstrated that TNF-α did not decrease ICAM-1 levels in RECs. We examined whether inhibition of TNF-α with TNF-α siRNA or etanercept, a TNFα receptor antagonist, could reduce melphalan-induced increased ICAM-1 levels in RECs. As result, neither TNF-α siRNA nor etanercept could reduce ICAM-1 levels (FIGS. 18A and 18B). While etanercept did reduce REC apoptosis after melphalan treatment, it did not reach statistical significance (FIG. 18C).

Figure 19A:
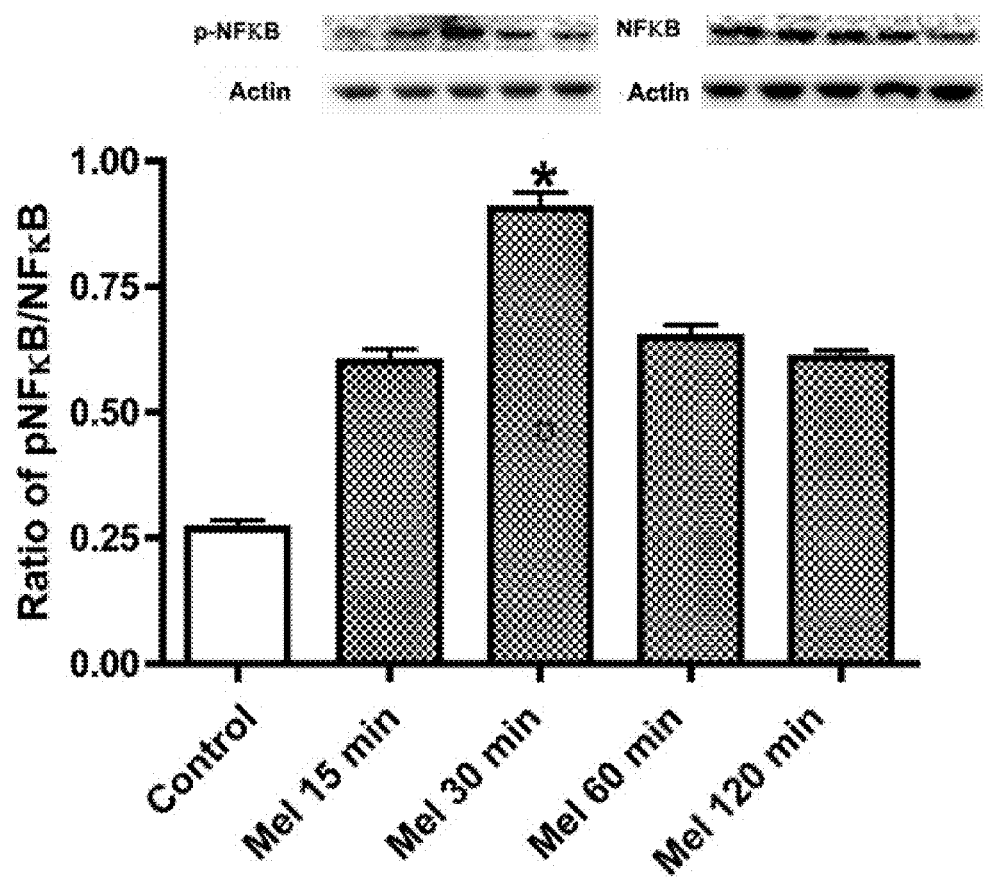
FIG. 19A shows images and a graph depicting Western Blot results for the ratio of Phospho-NF-κB to total NF-κB after melphalan treatment.
Figure 19B:
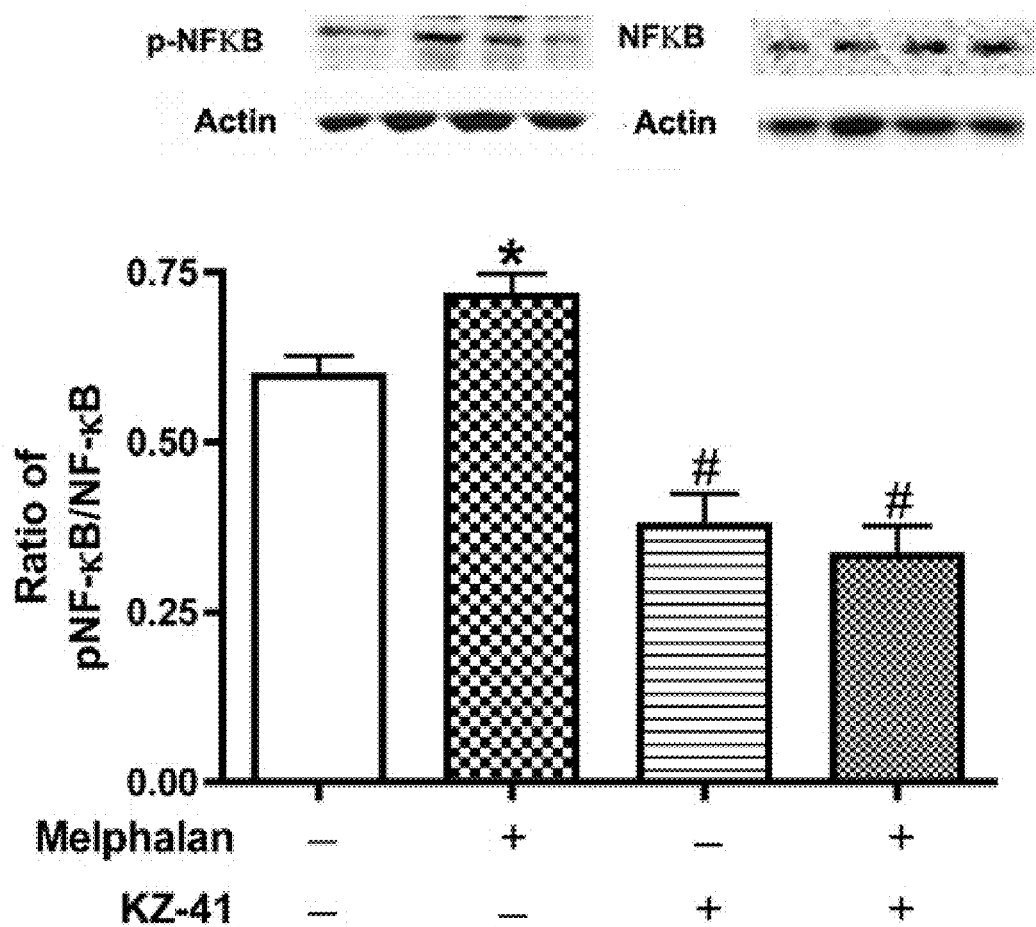
FIG. 19B shows images and a graph depicting Western blot results for ratio of Phospho-NF-κB to total NF-κB after melphalan and KZ-41 treatments.
Figure 19C:
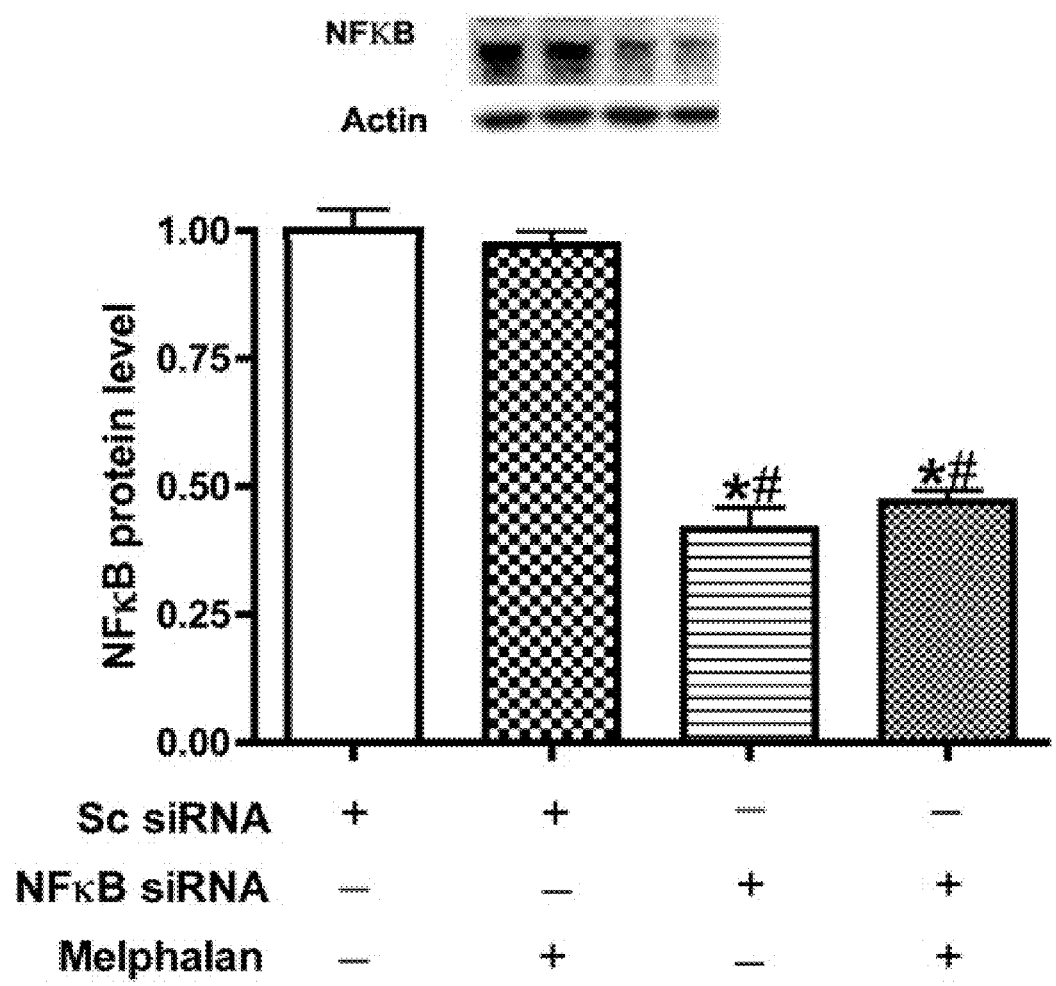
FIG. 19C shows images and a graph depicting a control experiment to demonstrate that NF-κB siRNA was able to significantly reduce NF-κB protein levels.
Figure 19D:
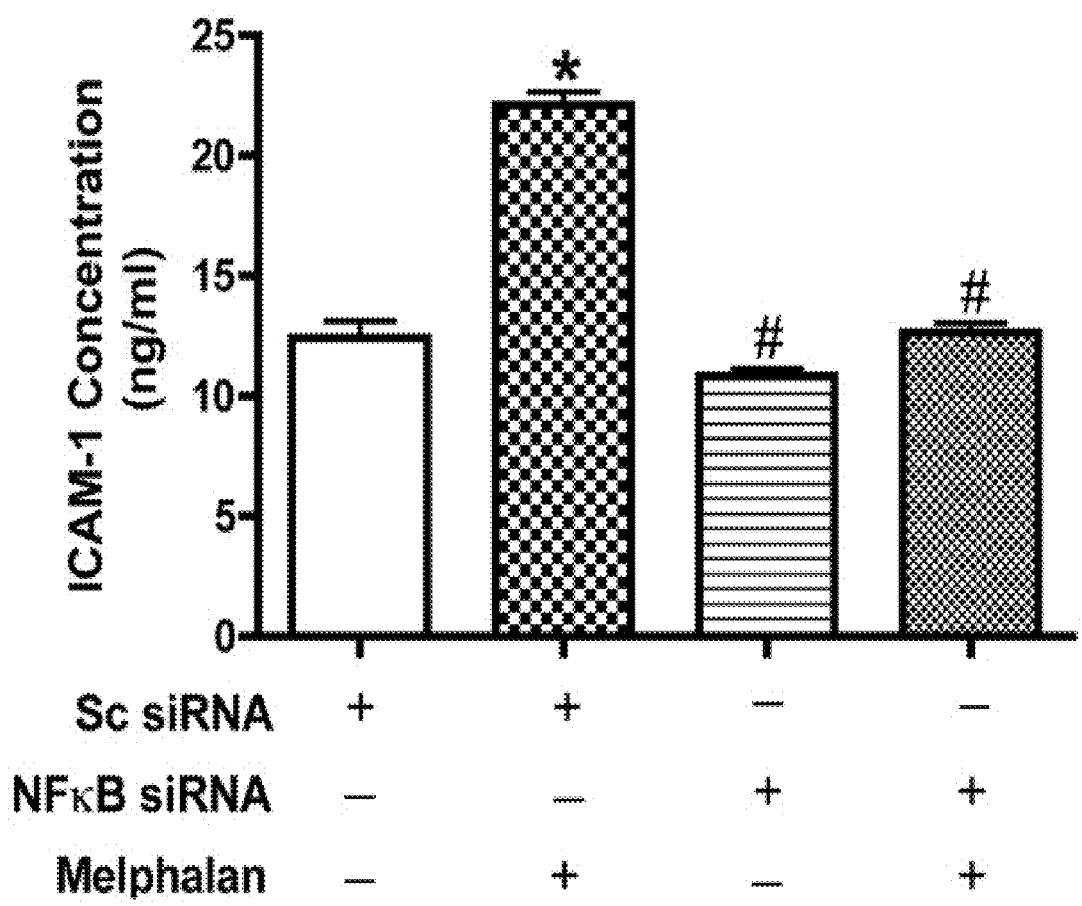
FIG. 19D shows images and a graph depicting ICAM-1 ELISA results after melphalan and NF-κB siRNA treatment. The symbol * means P<0.05 vs. control. The symbol # means P<0.05 vs. melphalan only. In each group, 4 cell cultures were performed and assayed. All data are represented as mean values±standard error of the mean.

We further demonstrated that KZ-41 could inhibit melphalan-induced ICAM-1 activation through NF-κB. We found that Melphalan (4 μg/mL) could induce NF-κB phosphorylation in a time-dependent manner in RECs (FIG. 19A). Maximum increases in NF-κB$^{Ser536}$ phosphorylation occurred at 30 minutes, with increased NF-κB levels for at least 2 hours (FIG. 19A). In addition, melphalan-induced ICAM-1 upregulation was blocked by either KZ-41 (FIG. 19B, comparing the bar in the group treated with both melphalan and KZ-41 with the bar in the group treated with melphalan alone) or NF-κB siRNA (FIG. 19D, comparing the bar in the group treated with both melphalan and NF-κB siRNA with the bar in the group treated with melphalan and Sc siRNA). As shown in FIG. 19C, demonstrates the NF-κB siRNA significantly reduce NF-κB levels.

Figure 20A:
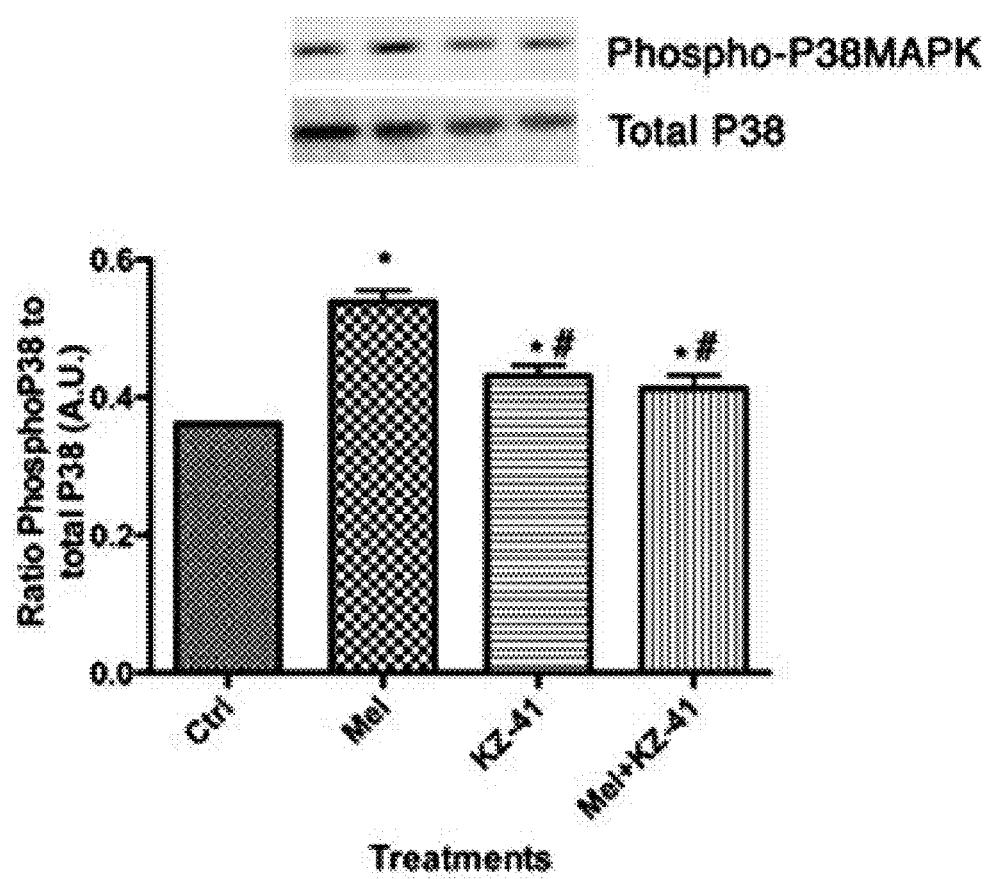
FIG. 20A shows images and a graph depicting the expression of Phospho-P38$^{MAPK}$ and total P38$^{MAPK}$ in RECs with or without treatment with KZ-41.
Figure 20B:
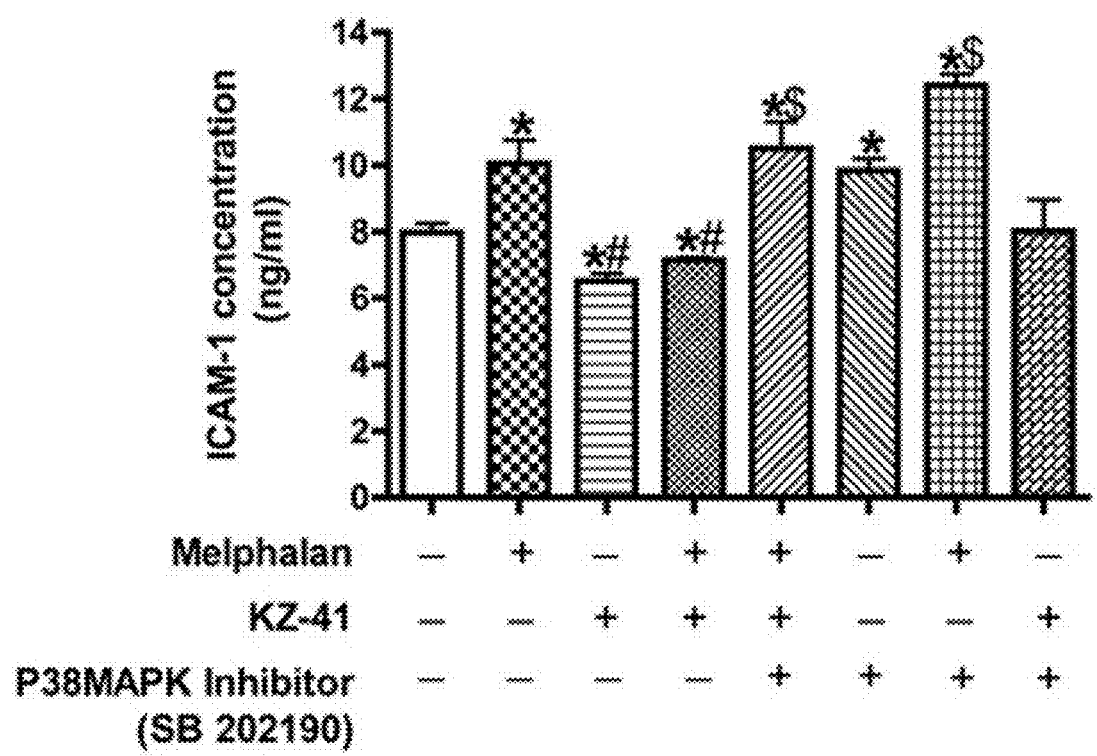
FIG. 20B shows a graph depicting the ICAM-1 ELISA results in RECs treated with various combinations of melphalan, KZ-41, the P38$^{MAPK}$ inhibitor SB202190. The symbol * means P<0.05 vs. control. The symbol # means P<0.05 vs. Melphalan. The symbol $ means P<0.05 vs. KZ-41. The symbol & means P<0.05 vs. KZ-41+Melphalan. In each group, 4 cell cultures were performed and assayed. All data are represented as mean values±standard error of the mean.

We further demonstrated that KZ-41 could inhibit melphalan-induced ICAM-1 activation through p38$^{MAPK}$ in RECs. We first found that KZ-41 could restore the phosphorylation level of P38$^{MAPK}$ that was induced by melphalan in RECs. See FIG. 20A, comparing the bar over the group of Mel+KZ-41 with the bar over the group of Mel. We then tested whether KZ-41 could still inhibit melphalan-induced up-regulation of ICAM-1 levels if p38$^{MAPK}$ was blocked by SB202190 (a p38$^{MAPK}$ inhibitor), and found that KZ-41 could not inhibit melphalan-induced up-regulation of ICAM-1 levels if p38$^{MAPK}$ was blocked by SB202190 (FIG. 20B), suggesting that KZ-41's inhibitory effects on melphalan-induced ICAM-1 activation depended on p38$^{MAPK}$ in RECs.

Figure 21A:
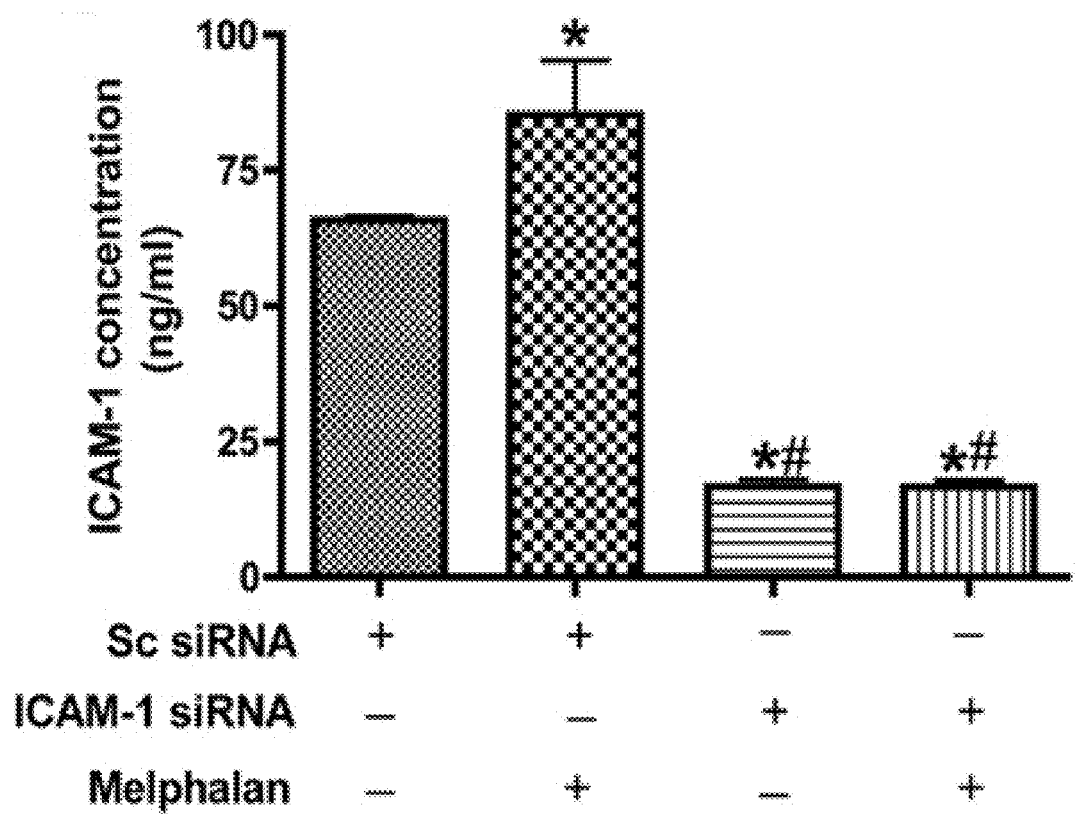
FIG. 21A shows a graph depicting ICAM-1 levels in RECs treated with ICAM-1 siRNA and/or melphalan. The Y-axis shows the ICAM-1 concentrations at ng/ml.
Figure 21B:
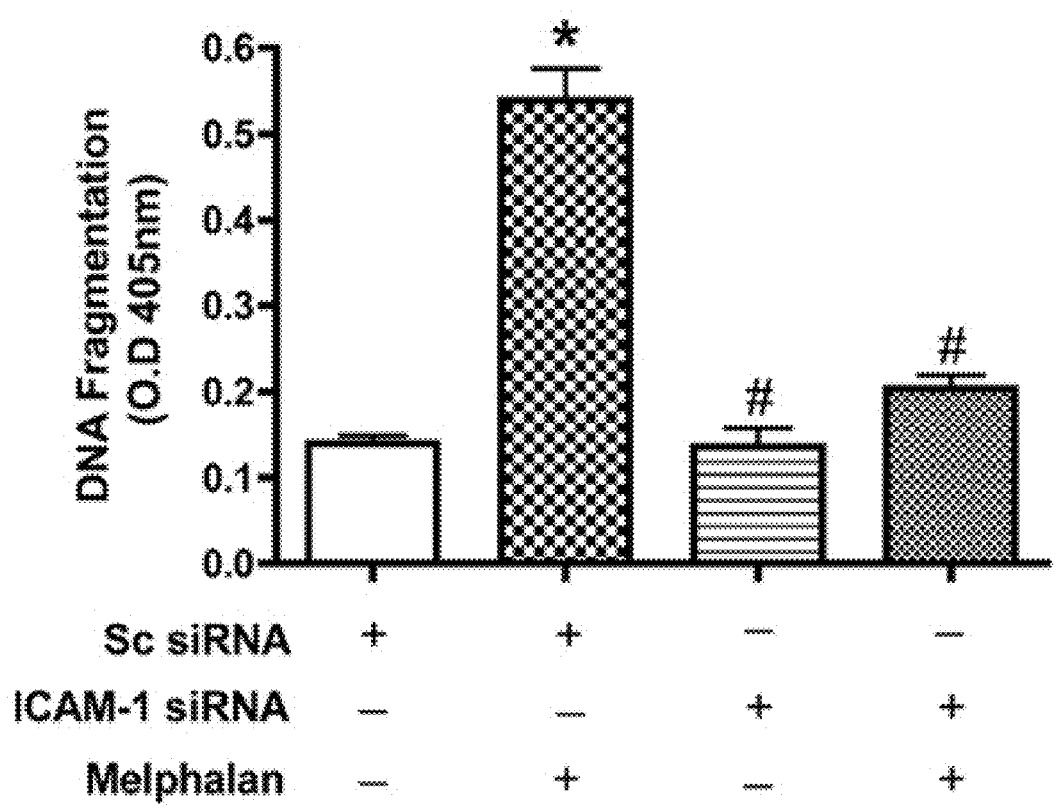
FIG. 21B shows a graph depicting cell death ELISA results of RECs treated with ICAM-1 siRNA and/or melphalan.
Figure 21C:
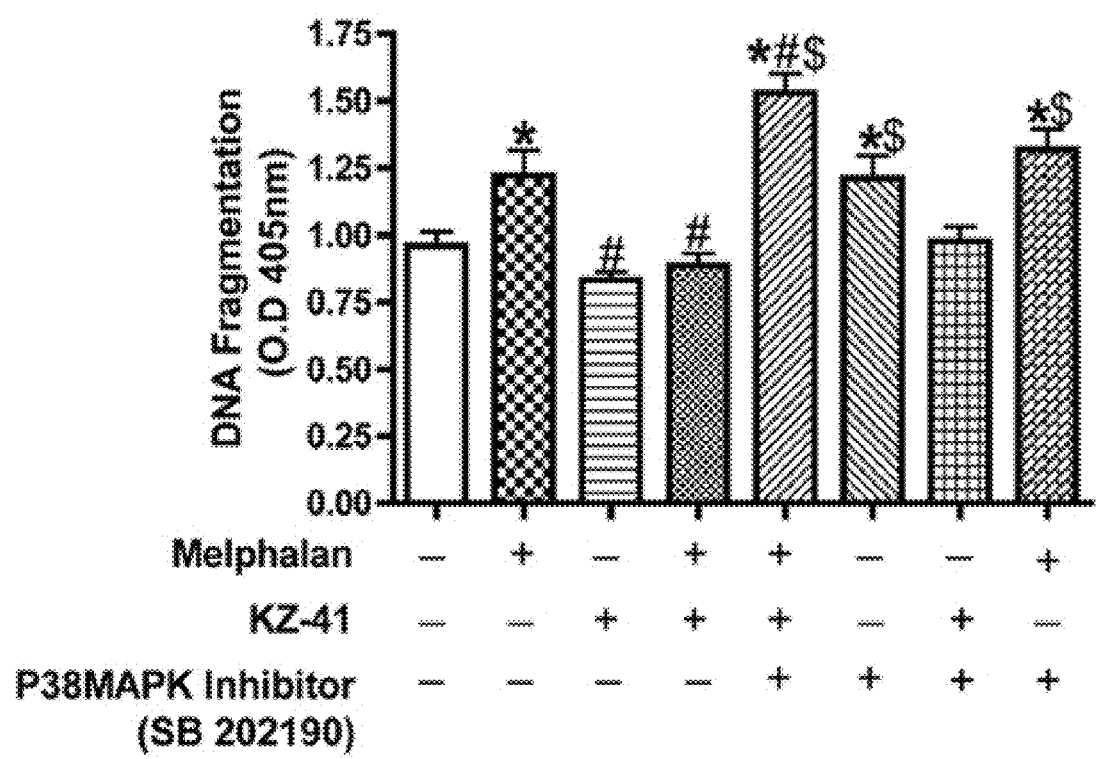
FIG. 21C shows a graph depicting cell death ELISA results of RECs treated with various combinations of melphalan, KZ-41, and SB 202190.
Figure 21D:
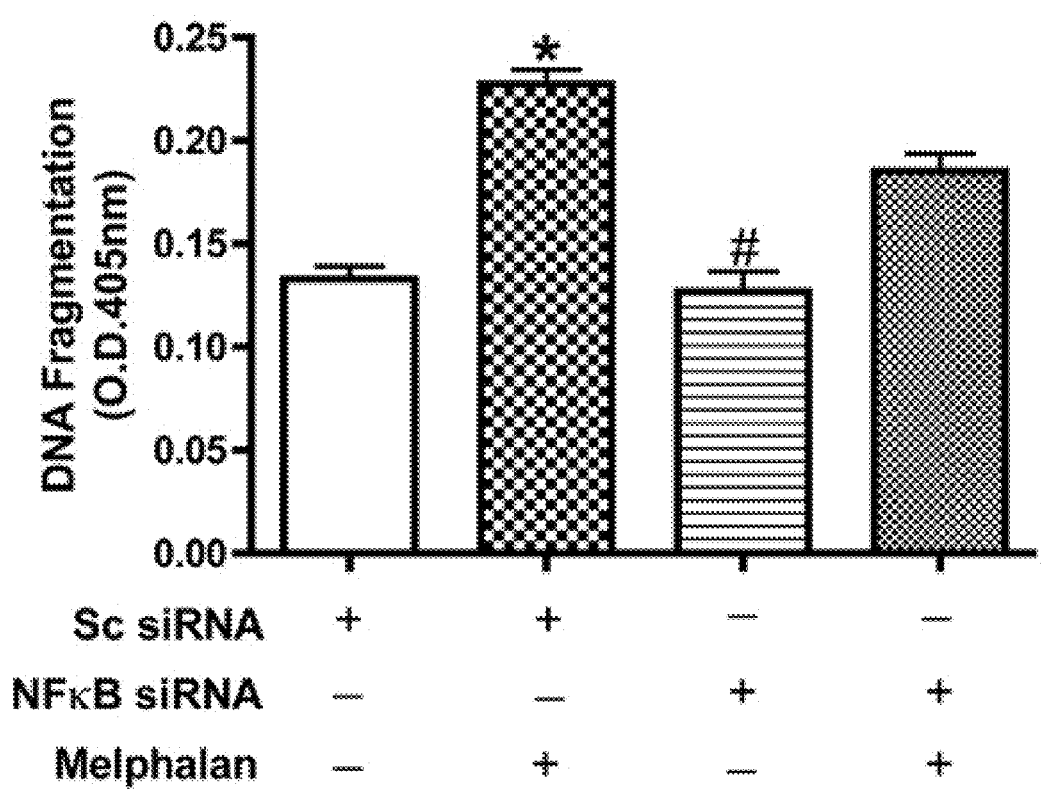
FIG. 21D shows a graph depicting cell death ELISA results of RECs treated with NF-κB siRNA and or melphalan. The symbol * means P<0.05 vs. control. The symbol # means P<0.05 vs. Melphalan. The symbol $ means P<0.05 vs. KZ-41. The symbol & means P<0.05 vs. KZ-41+Melphalan. In each group, 4 cell cultures were performed and assayed. All data are represented as mean values±standard error of the mean.

We further demonstrated that KZ-41 could inhibit melphalan-induced REC apoptosis through p38$^{MAPK}$. We used NF-κB siRNA, the p38$^{MAPK}$ inhibitor SB202190, and ICAM-1 siRNA to in REC apoptosis analysis. We demonstrated that ICAM-1 siRNA had inhibitory effects on ICAM-1 expression (FIG. 21A), that ICAM-1 siRNA could counter melphalan's proapoptotic effects in RECs (FIG. 21B), and that ICAM-1 siRNA could not inhibit melphalan-induced REC apoptosis if p38$^{MAPK}$ was blocked by SB202190, suggesting that KZ-41's inhibitory effects on melphalan-induced apoptosis depended on p38 in RECs (FIG. 21C).

In summary, we demonstrated that KZ-41 could protect the REC from melphalan-induced REC toxicity. Super selective intra-ophthalmic artery chemotherapy (SSIOAC) using melphalan continues to be used for the treatment of retinoblastoma (Abramson et al., 2008; Gobin et al., 2011), despite the reports of deleterious changes to the retina and choroid of children (Ditta et al., 2012; Shields et al., 2011; Wilson et al., 2011). One option to improve this therapy is to mitigate the direct melphalan-induced REC toxicity. Here we demonstrated that KZ-41 could protect the REC, while not preventing melphalan-induced apoptosis in Y79 retinoblastoma cells. Indeed, KZ-41 was effective in preventing melphalan-induced apoptosis in REC, without altering melphalan's actions on retinoblastoma cells and could serve as an agent for preventing, mitigating, or cure the rental toxicity seen in SSIOAC.

While the present invention has been disclosed with reference to certain embodiments, numerous modifications, alterations, and changes to the described embodiments are possible without departing from the full scope of the invention, as described in the specification and claims.

REFERENCES

Abramson, D. H., I. J. Dunkel, S. E. Brodie, J. W. Kim, and Y. P. Gobin. 2008. A phase I/II study of direct intraarterial (ophthalmic artery) chemotherapy with melphalan for intraocular retinoblastoma initial results. *Ophthalmology.* 115:1398-1404, 1404 e1391.

Aiello, L. P., E. A. Pierce, E. D. Foley, H. Takagi, H. Chen, L. Riddle, N. Ferrara, G. L. King, and L. E. Smith. 1995. Suppression of retinal neovascularization in vivo by inhibition of vascular endothelial growth factor (VEGF) using soluble VEGF-receptor chimeric proteins. *Proceedings of the National Academy of Sciences of the United States of America.* 92:10457-10461.

Akesson, C., H. Lindgren, R. W. Pero, T. Leanderson, and F. Ivars. 2005. Quinic acid is a biologically active component of the *Uncaria tomentosa* extract C-Med 100. *International immunopharmacology.* 5:219-229.

Alessi, D. R., M. Andjelkovic, B. Caudwell, P. Cron, N. Morrice, P. Cohen, and B. A. Hemmings. 1996. Mechanism of activation of protein kinase B by insulin and IGF-1. *The EMBO journal.* 15:6541-6551.

Alon, R., R. C. Fuhlbrigge, E. B. Finger, and T. A. Springer. 1996. Interactions through L-selectin between leukocytes and adherent leukocytes nucleate rolling adhesions on selectins and VCAM-1 in shear flow. *The Journal of cell biology.* 135:849-865.

Ammar, H. O., H. A. Salama, M. Ghorab, and A. A. Mahmoud. 2009. Nanoemulsion as a potential ophthalmic delivery system for dorzolamide hydrochloride. *AAPS PharmSciTech.* 10:808-819.

Arnold, T. D., G. M. Ferrero, H. Qiu, I. T. Phan, R. J. Akhurst, E. J. Huang, and L. F. Reichardt. 2012. Defective retinal vascular endothelial cell development as a consequence of impaired integrin alphaVbeta8-mediated activation of transforming growth factor-beta. *The Journal of neuroscience: the official journal of the Society for Neuroscience.* 32:1197-1206.

Avery, R. B., M. Diener-West, S. M. Reynolds, H. E. Grossniklaus, W. R. Green, and D. M. Albert. 2008. Histopathologic characteristics of choroidal melanoma in eyes enucleated after iodine 125 brachytherapy in the collaborative ocular melanoma study. *Archives of ophthalmology.* 126:207-212.

Bassoli, B. K., P. Cassolla, G. R. Borba-Murad, J. Constantin, C. L. Salgueiro-Pagadigorria, R. B. Bazotte, R. S. da Silva, and H. M. de Souza. 2008. Chlorogenic acid reduces the plasma glucose peak in the oral glucose tolerance test: effects on hepatic glucose release and glycaemia. *Cell biochemistry and function.* 26:320-328.

Bianciotto, C., C. L. Shields, C. Pirondini, A. Mashayekhi, M. Furuta, and J. A. Shields. 2010. Proliferative radiation retinopathy after plaque radiotherapy for uveal melanoma. *Ophthalmology.* 117:1005-1012.

Brown, G. C., J. A. Shields, G. Sanborn, J. J. Augsburger, P. J. Savino, and N. J. Schatz. 1982. Radiation retinopathy. *Ophthalmology.* 89:1494-1501.

Burns, A. R., R. A. Bowden, Y. Abe, D. C. Walker, S. I. Simon, M. L. Entman, and C. W. Smith. 1999. P-selectin mediates neutrophil adhesion to endothelial cell borders. *Journal of leukocyte biology.* 65:299-306.

Cai, Y., Q. Luo, M. Sun, and H. Corke. 2004. Antioxidant activity and phenolic compounds of 112 traditional Chinese medicinal plants associated with anticancer. *Life sciences.* 74:2157-2184.

Carpenter, C. L., B. C. Duckworth, K. R. Auger, B. Cohen, B. S. Schaffhausen, and L. C. Cantley. 1990. Purification and characterization of phosphoinositide 3-kinase from rat liver. *The Journal of biological chemistry.* 265:19704-19711.

Chang, W. C., C. H. Chen, M. F. Lee, T. Chang, and Y. M. Yu. 2010. Chlorogenic acid attenuates adhesion molecules upregulation in IL-1beta-treated endothelial cells. *European journal of nutrition.* 49:267-275.

Connor, K. M., N. M. Krah, R. J. Dennison, C. M. Aderman, J. Chen, K. I. Guerin, P. Sapieha, A. Stahl, K. L. Willett, and L. E. Smith. 2009. Quantification of oxygen-induced retinopathy in the mouse: a model of vessel loss, vessel regrowth and pathological angiogenesis. *Nature protocols.* 4:1565-1573.

Conti, S. M., and P. J. Kertes. 2006. The use of intravitreal corticosteroids, evidence-based and otherwise. *Current opinion in ophthalmology.* 17:235-244.

Costa, G. N., J. Vindeirinho, C. Cavadas, A. F. Ambrosio, and P. F. Santos. 2012. Contribution of TNF receptor 1 to retinal neural cell death induced by elevated glucose. *Molecular and Cellular Neuroscience.* 50:113-123.

Diener-West, M., J. D. Earle, S. L. Fine, B. S. Hawkins, C. S. Moy, S. M. Reynolds, A. P. Schachat, and B. R. Straatsma. 2001. The COMS randomized trial of iodine 125 brachytherapy for choroidal melanoma, III: initial mortality findings. COMS Report No. 18. *Archives of ophthalmology.* 119:969-982.

Ditta, L. C., A. F. Choudhri, B. C. Tse, M. M. Landers, B. G. Haik, J. J. Steinle, J. S. Williams, and M. W. Wilson. 2012. Validating a Non-Human Primate Model of Super-Selective Intra-Ophthalmic Artery Chemotherapy: Comparing Ophthalmic Artery Diameters. *Invest Ophthalmol Vis Sci.*

Egger, E., A. Schalenbourg, L. Zografos, L. Bercher, T. Boehringer, L. Chamot, and G. Goitein. 2001. Maximizing local tumor control and survival after proton beam radiotherapy of uveal melanoma. *International journal of radiation oncology, biology, physics.* 51:138-147.

el-Remessy, A. B., M. Bartoli, D. H. Platt, D. Fulton, and R. B. Caldwell. 2005. Oxidative stress inactivates VEGF survival signaling in retinal endothelial cells via PI 3-kinase tyrosine nitration. *Journal of cell science.* 118:243-252.

Engerman, R. L. 1989. Pathogenesis of diabetic retinopathy. *Diabetes.* 38:1203-1206.

Espinoza-Fonseca, L. M. 2005. Targeting MDM2 by the small molecule RITA: towards the development of new multi-target drugs against cancer. *Theoretical biology & medical modelling.* 2:38.

Finger, P. T., K. J. Chin, and G. Duvall. 2009. Palladium-103 ophthalmic plaque radiation therapy for choroidal melanoma: 400 treated patients. *Ophthalmology.* 116:790-796, 796 e791.

Frangos, J. A., L. V. McIntire, and S. G. Eskin. 1988. Shear stress induced stimulation of mammalian cell metabolism. *Biotechnol Bioeng.* 32:1053-1060.

Gaber, M. W., O. M. Sabek, K. Fukatsu, H. G. Wilcox, M. F. Kiani, and T. E. Merchant. 2003. Differences in ICAM-1 and TNF-alpha expression between large single fraction and fractionated irradiation in mouse brain. *International journal of radiation biology.* 79:359-366.

Geraldes, P., J. Hiraoka-Yamamoto, M. Matsumoto, A. Clermont, M. Leitges, A. Marette, L. P. Aiello, T. S. Kern, and G. L. King. 2009. Activation of PKC-delta and SHP-1 by hyperglycemia causes vascular cell apoptosis and diabetic retinopathy. *Nature medicine.* 15:1298-1306.

Gillies, M. C., F. K. Sutter, J. M. Simpson, J. Larsson, H. Ali, and M. Zhu. 2006. Intravitreal triamcinolone for refractory diabetic macular edema: two-year results of a double-masked, placebo-controlled, randomized clinical trial. *Ophthalmology.* 113:1533-1538.

Giuliari, G. P., A. Sadaka, D. M. Hinkle, and E. R. Simpson. 2011. Current treatments for radiation retinopathy. *Acta Oncologica.* 50:6-13.

Gobin, Y. P., I. J. Dunkel, B. P. Man, S. E. Brodie, and D. H. Abramson. 2011. Intra-arterial Chemotherapy for the Management of Retinoblastoma: Four-Year Experience. *Archives of ophthalmology.* 129:732-737.

Googe, J., A. J. Brucker, N. M. Bressler, H. Qin, L. P. Aiello, A. Antoszyk, R. W. Beck, S. B. Bressler, F. L. Ferris, 3rd, A. R. Glassman, D. Marcus, and C. R. Stockdale. 2011. Randomized trial evaluating short-term effects of intravitreal ranibizumab or triamcinolone acetonide on macular edema after focal/grid laser for diabetic macular edema in eyes also receiving panretinal photocoagulation. *Retina.* 31:1009-1027.

Gunduz, K., C. L. Shields, J. A. Shields, J. Cater, J. E. Freire, and L. W. Brady. 1999. Radiation complications and tumor control after plaque radiotherapy of choroidal melanoma with macular involvement. *American journal of ophthalmology.* 127:579-589.

Haas, A., O. Pinter, G. Papaefthymiou, M. Weger, A. Berghold, O, Schrottner, K. Mullner, G. Pendl, and G. Langmann. 2002. Incidence of radiation retinopathy after high-dosage single-fraction gamma knife radiosurgery for choroidal melanoma. *Ophthalmology.* 109:909-913.

Ho, F. M., S. H. Liu, C. S. Liau, P. J. Huang, and S. Y. Lin-Shiau. 2000. High glucose-induced apoptosis in human endothelial cells is mediated by sequential activations of c-Jun NH(2)-terminal kinase and caspase-3. *Circulation.* 101:2618-2624.

Jampol, L. M., C. S. Moy, T. G. Murray, S. M. Reynolds, D. M. Albert, A. P. Schachat, K. R. Diddie, R. E. Engstrom, Jr., P. T. Finger, K. R. Hovland, L. Joffe, K. R. Olsen, and C. G. Wells. 2002. The COMS randomized trial of iodine 125 brachytherapy for choroidal melanoma: IV. Local treatment failure and enucleation in the first 5 years after brachytherapy. COMS report no. 19. *Ophthalmology.* 109:2197-2206.

Jiang, Y., Q. Zhang, C. Soderland, and J. J. Steinle. 2012. TNFalpha and SOCS3 regulate IRS-1 to increase retinal endothelial cell apoptosis. *Cellular signalling.* 24:1086-1092.

Johnston, K. L., M. N. Clifford, and L. M. Morgan. 2003. Coffee acutely modifies gastrointestinal hormone secretion and glucose tolerance in humans: glycemic effects of chlorogenic acid and caffeine. *The American journal of clinical nutrition.* 78:728-733.

Kinashi, T. 2005. Intracellular signalling controlling integrin activation in lymphocytes. *Nature reviews. Immunology.* 5:546-559.

Krema, H., S. Somani, A. Sahgal, W. Xu, M. Heydarian, D. Payne, H. McGowan, H. Michaels, E. R. Simpson, and N. Laperriere. 2009. Stereotactic radiotherapy for treatment of juxtapapillary choroidal melanoma: 3-year follow-up. *The British journal of ophthalmology.* 93:1172-1176.

Lawrence, M. B., L. V. McIntire, and S. G. Eskin. 1987. Effect of flow on polymorphonuclear leukocyte/endothelial cell adhesion. *Blood.* 70:1284-1290.

Ley, K., C. Laudanna, M. I. Cybulsky, and S. Nourshargh. 2007. Getting to the site of inflammation: the leukocyte adhesion cascade updated. *Nature reviews. Immunology.* 7:678-689.

Marshall, S. M., and A. Flyvbjerg. 2006. Prevention and early detection of vascular complications of diabetes. *BMJ.* 333:475-480.

McCarty, O. J., S. A. Mousa, P. F. Bray, and K. Konstantopoulos. 2000. Immobilized platelets support human colon carcinoma cell tethering, rolling, and firm adhesion under dynamic flow conditions. *Blood.* 96:1789-1797.

Miyamoto, K., S. Khosrof, S. E. Bursell, R. Rohan, T. Murata, A. C. Clermont, L. P. Aiello, Y. Ogura, and A. P. Adamis. 1999. Prevention of leukostasis and vascular leakage in streptozotocin-induced diabetic retinopathy via intercellular adhesion molecule-1 inhibition. *Proceedings of the National Academy of Sciences of the United States of America.* 96:10836-10841.

Munier, F. L., M. Beck-Popovic, A. Balmer, M. C. Gaillard, E. Bovey, and S. Binaghi. 2011. Occurrence of sectoral choroidal occlusive vasculopathy and retinal arteriolar embolization after superselective ophthalmic artery chemotherapy for advanced intraocular retinoblastoma. *Retina.* 31:566-573.

Olthof, M. R., P. C. Hollman, and M. B. Katan. 2001. Chlorogenic acid and caffeic acid are absorbed in humans. *The Journal of nutrition.* 131:66-71.

Parks, D. J., L. V. Lafrance, R. R. Calvo, K. L. Milkiewicz, V. Gupta, J. Lattanze, K. Ramachandren, T. E. Carver, E. C. Petrella, M. D. Cummings, D. Maguire, B. L. Grasberger, and T. Lu. 2005. 1,4-Benzodiazepine-2,5-diones as small molecule antagonists of the HDM2-p53 interaction: discovery and SAR. *Bioorganic & medicinal chemistry letters.* 15:765-770.

Pham, C. T., R. Blanc, L. Lumbroso-Le Rouic, S. Pistocchi, B. Bartolini, and M. Piotin. 2012. Access to the ophthalmic artery by retrograde approach through the posterior communicating artery for intra-arterial chemotherapy of retinoblastoma. *Neuroradiology.* 54:845-848.

Phillpotts, B. A., R. J. Sanders, J. A. Shields, J. D. Griffiths, J. A. Augsburger, and C. L. Shields. 1995. Uveal melanomas in black patients: a case series and comparative review. *Journal of the National Medical Association.* 87:709-714.

Ramagiri, S., F. Ma, H. Kosanam, X. Wang, R. Patil, D. D. Miller, E. Geisert, and C. R. Yates. 2009. Fast and sensitive liquid chromatography/electrospray mass spectrometry method to study ocular penetration of EDL-155, a novel antitumor agent for retinoblastoma in rats. *Journal of mass spectrometry: JMS.* 44:786-793.

Shafiq-un-Nabi, S., F. Shakeel, S. Talegaonkar, J. Ali, S. Baboota, A. Ahuja, R. K. Khar, and M. Ali. 2007. Formulation development and optimization using nanoemulsion technique: a technical note. *AAPS PharmSciTech.* 8:Article 28.

Sheng, Y., C. Akesson, K. Holmgren, C. Bryngelsson, V. Giamapa, and R. W. Pero. 2005. An active ingredient of Cat's Claw water extracts identification and efficacy of quinic acid. *Journal of ethnopharmacology.* 96:577-584.

Shields, C. L., C. G. Bianciotto, P. Jabbour, G. C. Griffin, A. Ramasubramanian, R. Rosenwasser, and J. A. Shields. 2011. Intra-arterial Chemotherapy for Retinoblastoma: Report No. 2, Treatment Complications. *Archives of ophthalmology.*

Shimura, M., K. Yasuda, T. Nakazawa, T. Kano, S. Ohta, and M. Tamai. 2003. Quantifying alterations of macular thickness before and after panretinal photocoagulation in patients with severe diabetic retinopathy and good vision. *Ophthalmology.* 110:2386-2394.

Smith, L. E., E. Wesolowski, A. McLellan, S. K. Kostyk, R. D'Amato, R. Sullivan, and P. A. D'Amore. 1994. Oxygen-induced retinopathy in the mouse. *Invest Ophthalmol Vis Sci.* 35:101-111.

Springer, T. A. 1995. Traffic signals on endothelium for lymphocyte recirculation and leukocyte emigration. *Annual review of physiology.* 57:827-872.

Stahl, A., K. M. Connor, P. Sapieha, J. Chen, R. J. Dennison, N. M. Krah, M. R. Seaward, K. L. Willett, C. M. Aderman, K. I. Guerin, J. Hua, C. Lofqvist, A. Hellstrom, and L. E. Smith. 2010. The mouse retina as an angiogenesis model. *Invest Ophthalmol Vis Sci.* 51:2813-2826.

Steinle, J. J., Q. Zhang, K. E. Thompson, J. Toutounchian, C. R. Yates, C. Soderland, F. Wang, C. Stewart, B. G. Haik, J. S. Williams, J. S. Jackson, T. D. Mandrell, D. A. Johnson, and M. W. Wilson. 2012. Intra-ophthalmic artery chemotherapy triggers vascular toxicity through endothelial cell inflammation and leukostasis. *Invest Ophthalmol Vis Sci.*

Vanhaesebroeck, B., S. J. Leevers, K. Ahmadi, J. Timms, R. Katso, P. C. Driscoll, R. Woscholski, P. J. Parker, and M. D. Waterfield. 2001. Synthesis and function of 3-phosphorylated inositol lipids. *Annual review of biochemistry.* 70:535-602.

Vassilev, L. T., B. T. Vu, B. Graves, D. Carvajal, F. Podlaski, Z. Filipovic, N. Kong, U. Kammlott, C. Lukacs, C. Klein, N. Fotouhi, and E. A. Liu. 2004. In vivo activation of the p53 pathway by small-molecule antagonists of MDM2. *Science.* 303:844-848.

Viebahn, M., M. E. Barricks, and M. D. Osterloh. 1991. Synergism between diabetic and radiation retinopathy: case report and review. *The British journal of ophthalmology.* 75:629-632.

Wagers, A. J., C. M. Waters, L. M. Stoolman, and G. S. Kansas. 1998. Interleukin 12 and interleukin 4 control T cell adhesion to endothelial selectins through opposite effects on alpha1,3-fucosyltransferase VII gene expression. *The Journal of experimental medicine.* 188:2225-2231.

Waisbourd, M., M. Goldstein, and A. Loewenstein. 2011. Treatment of diabetic retinopathy with anti-VEGF drugs. *Acta ophthalmologica.* 89:203-207.

Wilson, M. W., J. S. Jackson, B. X. Phillips, J. Buchanan, S. Frase, F. Wang, J. J. Steinle, C. F. Stewart, T. D. Mandrell, B. G. Haik, and J. S. Williams. 2011. Real-time ophthalmoscopic findings of superselective intraophthalmic artery chemotherapy in a nonhuman primate model. *Archives of ophthalmology.* 129:1458-1465.

Witt, T. C. 2003. Stereotactic radiosurgery for pituitary tumors. *Neurosurgical focus.* 14:e10.

Yamane, T., A. Kaneko, and M. Mohri. 2004. The technique of ophthalmic arterial infusion therapy for patients with intraocular retinoblastoma. *Int J Clin Oncol.* 9:69-73.

Yu, Y. M., Z. H. Wang, C. H. Liu, and C. S. Chen. 2007. Ellagic acid inhibits IL-1beta-induced cell adhesion molecule expression in human umbilical vein endothelial cells. *The British journal of nutrition.* 97:692-698.

Yuan, H., M. W. Gaber, T. McColgan, M. D. Naimark, M. F. Kiani, and T. E. Merchant. 2003. Radiation-induced permeability and leukocyte adhesion in the rat blood-brain barrier: modulation with anti-ICAM-1 antibodies. *Brain research.* 969:59-69.

Zamber, R. W., and J. L. Kinyoun. 1992. Radiation retinopathy. *The Western journal of medicine.* 157:530-533.

Zeng, K., K. E. Thompson, C. S. Presley, D. D. Miller, and C. R. Yates. 2011. Preclinical pharmacokinetics of the radiomitigator KZ-41 in rats. *Xenobiotica; the fate of foreign compounds in biological systems.* 41:1006-1012.

Zeng, K., K. E. Thompson, C. R. Yates, and D. D. Miller. 2009. Synthesis and biological evaluation of quinic acid derivatives as anti-inflammatory agents. *Bioorganic & medicinal chemistry letters.* 19:5458-5460.

Zhang, Q., C. Soderland, and J. J. Steinle. 2013. Regulation of retinal endothelial cell apoptosis through activation of the IGFBP-3 receptor. *Apoptosis: an international journal on programmed cell death.* 18:361-368.

Zhang, X., G. Barile, S. Chang, A. Hays, S. Pachydaki, W. Schiff, and J. Sparrow. 2005. Apoptosis and cell proliferation in proliferative retinal disorders: PCNA, Ki-67, caspase-3, and PARP expression. *Current eye research.* 30:395-403.

Zhong, H., and H. A. Carlson. 2005. Computational studies and peptidomimetic design for the human p53-MDM2 complex. *Proteins.* 58:222-234.

We claim:

1. A method for regulating retinal endothelial cell viability in treating radiation retinopathy in a mammal, comprising administering to the mammal a therapeutically effective amount of a quinic acid analog having a structure as in

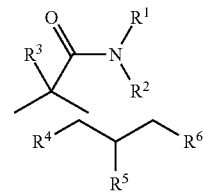

Formula I where
the ring may be singly, doubly, or completely saturated;
$R^1$ and $R^2$ are each independently H, straight or branched alkyl, aryl, benzyl, arylalkyl, or heterocyclic amine;
$R^3$ may be present or absent and, if present, may be H, hydroxyl, ether, alkoxy, or aryloxy; and
$R^4$, $R^5$, and $R^6$ are each independently H, hydroxyl, and alkoxy.

2. The method of claim 1 wherein $R^1$ and $R^2$ of Formula I form a piperidine ring with Nitrogen.

3. The method of claim 1 wherein when one of $R^1$ or $R^2$ of Formula I is hydrogen, the other of $R^1$ or $R^2$ is alkyl.

4. The method of claim 3 wherein the alkyl is —C3H7 and each of $R^3$-$R^6$ is hydroxyl.

5. The method of claim 1, wherein one or more of $R^3$, $R^4$, $R^5$ or $R^6$ are each independently connected to an antioxidant through an ester bond.

6. The method of claim 5, wherein the antioxidant is selected from the group consisting of caffeic acid, ferulic acid, and sinapic acid.

7. The method of claim 1, wherein the radiation retinopathy is due to exposure of the mammal's retinal endothelial cells to radiation.

8. The method of claim 7, wherein the radiation is used to treat an intraocular tumor.

9. The method of claim 7, wherein the radiation is gray.

10. The method of claim 1, wherein the mammal is a human.

11. The method of claim 1, wherein the regulation of retinal endothelial cell viability is to promote or maintain retinal endothelial cell viability.

12. The method of claim 1, wherein the regulation of the retinal endothelial cell viability is to reduce retinal endothelial cell death.

13. The method of claim 1, wherein the regulation of retinal endothelial cell viability is to prevent or reduce retinal neovascularization.

14. The method of claim 1, wherein the method is used in combination with one or more existing treatment method for radiation retinopathy, diabetic retinopathy, or mitigating side effects on retinal endothelial cells in treating retinoblastoma.

15. The method of claim 1, wherein the quinic acid analog is formulated in nanoemulsion.

16. The method of claim 15, wherein the quinic acid analog is delivered as an eye-drop.

\* \* \* \* \*